United States Patent
Barnicki et al.

(10) Patent No.: US 7,538,060 B2
(45) Date of Patent: May 26, 2009

(54) PALLADIUM-COPPER CHROMITE HYDROGENATION CATALYSTS

(75) Inventors: Scott Donald Barnicki, Kingsport, TN (US); Bruce LeRoy Gustafson, Kingsport, TN (US); Zhufang Liu, Kingsport, TN (US); Steven Thomas Perri, Kingsport, TN (US); Paul Randolph Worsham, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 142 days.

(21) Appl. No.: 11/674,831

(22) Filed: Feb. 14, 2007

(65) Prior Publication Data

US 2008/0194397 A1  Aug. 14, 2008

(51) Int. Cl.
*B01J 35/00* (2006.01)
*B01J 37/00* (2006.01)
*C07C 29/132* (2006.01)
*C07C 29/149* (2006.01)

(52) U.S. Cl. .................. 502/104; 502/110; 502/117; 568/885; 568/833

(58) Field of Classification Search .............. 502/104, 502/110, 117; 568/885, 833
See application file for complete search history.

(56) References Cited

U.S. PATENT DOCUMENTS

| | | | |
|---|---|---|---|
| 3,218,268 A | 11/1965 | Arnold | |
| 3,334,149 A | 8/1967 | Akin et al. | |
| 3,699,054 A | 10/1972 | Organ et al. | |
| 3,872,213 A | 3/1975 | Haseba | |
| 3,873,469 A | 3/1975 | Foster et al. | |
| 3,948,805 A | 4/1976 | Michalczyk et al. | |
| 4,072,471 A | 2/1978 | Morgan, Jr. et al. | |
| 4,086,262 A | 4/1978 | Chang et al. | |
| 4,091,041 A | 5/1978 | Smith | |
| 4,131,616 A | 12/1978 | Stiles | |
| 4,298,354 A | 11/1981 | Hardman et al. | |
| 4,482,647 A | 11/1984 | Smith | |
| 4,514,521 A | 4/1985 | Smith | |
| 4,698,325 A | 10/1987 | Andrew et al. | |
| 4,754,090 A | 6/1988 | Vila Peris et al. | |
| 4,935,395 A | 6/1990 | Mahajan et al. | |
| 5,169,869 A | 12/1992 | Miller et al. | |
| 5,196,602 A | 3/1993 | Budge et al. | |
| 5,221,652 A | 6/1993 | Tierney et al. | |
| 5,384,335 A | 1/1995 | Tierney et al. | |
| 5,385,949 A | 1/1995 | Tierney et al. | |
| 5,395,987 A | 3/1995 | Rathmell et al. | |
| 5,840,981 A | 11/1998 | Fuchs et al. | |
| 6,028,119 A | 2/2000 | Kokubu et al. | |
| 6,054,627 A | 4/2000 | Thakur et al. | |
| 6,090,741 A | 7/2000 | Wu et al. | |
| 6,245,948 B1 | 6/2001 | Fischer et al. | |
| 6,333,431 B1 | 12/2001 | Hashimoto et al. | |
| 6,448,425 B1 | 9/2002 | Gedon et al. | |
| 6,475,951 B1 | 11/2002 | Domesle et al. | |
| 6,664,402 B2 | 12/2003 | Manzer | |
| 6,903,140 B2 | 6/2005 | Font Freide et al. | |
| 2002/0006374 A1 | 1/2002 | Kourtakis et al. | |
| 2004/0198596 A1 | 10/2004 | Schlitter et al. | |
| 2004/0225133 A1 | 11/2004 | Holladay | |
| 2005/0244312 A1 | 11/2005 | Suppes et al. | |
| 2005/0272941 A1 | 12/2005 | Zhang et al. | |
| 2006/0235091 A1 | 10/2006 | Olah et al. | |

FOREIGN PATENT DOCUMENTS

| | | |
|---|---|---|
| EP | 1 031 377 | 8/2000 |
| JP | 56077297 | 6/1981 |
| JP | 57080344 | 5/1982 |
| JP | 60144387 | 7/1985 |
| JP | 63227534 A | 9/1988 |
| JP | 01121228 A | 5/1989 |
| JP | 6192146 | 7/1994 |
| JP | 6321823 | 11/1994 |
| JP | 08291158 | 11/1996 |
| WO | WO 8600545 | 1/1986 |

OTHER PUBLICATIONS

Copending U.S. Appl. No. 11/674,808, filed on Feb. 14, 2007.
Adkins et al, "Catalytic Hydrogenation of Esters", *J. Am. Chem. Soc.*, 53, 1931, pp. 1095-1097.
Adkins et al, "Selective Hydrogenation of Esters Containing a Naphthalene Nucleus", *J. Am. Chem. Soc.*, vol. 71, pp. 3528-3531.

(Continued)

*Primary Examiner*—Elvis O Price
(74) *Attorney, Agent, or Firm*—Eric D. Middlemas; Bernard J. Graves, Jr.

(57) ABSTRACT

Disclosed are catalysts comprising copper chromite, palladium and lanthanum having hydrogenation activity. The combination of copper chromite with palladium and lanthanum enhances catalyst activity more than the presence of either palladium alone or palladium in combination with alkali or alkaline earth metals. The catalysts are useful for the preparation of methanol from carbon monoxide and hydrogen and for the hydrogenation of carbonyl compounds such as, for example, aldehydes, ketones, and esters, to their corresponding alcohols. The catalysts may be used for the preparation of cyclohexanedimethanols from dialkyl cyclohexanedicarboxylates or of ethylene glycol from alkyl glycolates.

51 Claims, No Drawings

OTHER PUBLICATIONS

Adkins et al, "The Catalytic Hydrogenation of Organic Compounds Over Copper Chromite", *J. Am. Chem. Soc.*, 53, (1931) pp. 1091-1095.

Apai et al, "Relationship between Stable Monovalent Copper in Copper-Chromia Catalysts and Activity for Methanol Formation", *J. Chem. Soc., Chem. Commun.*, (1984) pp. 212-213.

"A Catalyst for Low- Temperature Methanol Synthesis" [online] [retrieved on Nov. 2, 2006] Retrieved from http://criepi.denken.or.jp/en/e_publication/a1996/96seika47.html pp. 1-5.

Conner et al, *J. Am. Chem. Soc.*, 53, (1931) p. 1091.

Conner et al, "The Preparation of Copper-Chromium Oxide Catalysts for Hydrogenation", Department of Chemistry, University of Wisconsin, Madison, Wisconsin, vol. 53, (1931) p. 2012.

Josefina et al, "Characterization and reactivity of Ru/single oxides catalysts for the syngas reaction", *Applied Catalysis A: General*, 274 (2004) pp. 295-301.

Maitlis, "Metal catalysed CO hydrogenation: herero- or homo-, what is the difference?" *Journal of Molecular Catalysis A: Chemical* 204-205 (2003) pp. 55-62.

Mohan et al, "Design and development of novel copper chromite catalysts (unsupported/supported) with enhanced activity", *Elsevier Science B.V., Preparation of Catalysts VII*, (1998) pp. 557-566.

Monnier et al, "A Study of the Catalytically Active Copper Species in the Synthesis of Methanol over Cu—Cr Oxide", *J. Catal.*, 92, (1985) pp. 119-126.

Mori et al, "Effect of Alkaline Carbonate on the Dissociation of the C—O Bond in the Methanation over $Ru/Al_2O_3$ Catalyst", *Journal of Catalysis*, 102, (1986) pp. 199-206.

Robinson et al, "Support effects in methanol synthesis over copper-containing catalysts", *Applied Catalysis*, 76, (1991), pp. 117-129.

Yang et al, "Methanol synthesis from $CO_2$-rich syngas over a $ZrO_2$ doped CuZnO catalyst", *Catalysis Today*, 115 (2006), 222-227.

Zhang et al, "Pd-promoted Cr/ZnO catalyst for synthesis of methanol from syngas", *Applied Catalysis A: General*, 309 (2006) pp. 28-32.

Kummer, J.T. et al, "Honeycomb Auto Exhaust Catalysts Containing Copper Chromite and Palladium", *Society of Automotive Engineers*, Automotive Engineering Congress and Exposition, Detroit, Michigan, (1976) pp. 1-16.

PCT International Search Report and Written Opinion for International Application No. PCT/US2008/001450 dated Jun. 5, 2008.

English abstract of JP 60144387 dated Jul. 30, 1985 (Inui Satoyuki).

PALLADIUM-COPPER CHROMITE HYDROGENATION CATALYSTS

FIELD OF THE INVENTION

This invention pertains to hydrogenation catalysts comprising copper chromite having palladium and lanthanum deposited thereon. This invention further pertains to processes for the preparation of methanol by hydrogenation of carbon monoxide and of alcohols by the hydrogenation of carbonyl compounds using the above hydrogenation catalysts.

DETAILED DESCRIPTION

The synthesis of methanol from mixtures of carbon monoxide, carbon dioxide, and hydrogen (referred to herein as "syngas") is an equilibrium reaction that favors high conversion to methanol at low operating temperatures. An increase in conversion of methanol at low temperature reduces the production cost of methanol by lowering the requirement for recycle of unreacted syngas and the attendant compression and capital costs. Moreover, operation at lower temperatures extends the life of methanol catalysts by retarding the rate of sintering. Sintering leads to gradual catalyst deactivation by reducing active catalyst surface area. The syngas feedstock typically used for the production of methanol also can contain high levels of carbon dioxide, which can inhibit the activity of the methanol catalysts. Methanol catalysts are needed, therefore, which have high activity under mild operating conditions and which can tolerate carbon dioxide well.

The preparation of alcohols by hydrogenation of carbonyl compounds such as, for example, aldehydes, ketones, and carboxylic acid esters, is an important commercial process. For example, the hydrogenation of carboxylic acid esters is used for the production of detergent alcohols and polymer intermediates. Typically, the hydrogenation of esters requires aggressive process conditions and some catalysts used in these processes can present disposal problems. For example, when used in fixed bed reactors, the existing catalysts are used as shaped bodies which can have limited mechanical stability under the mechanical stresses occurring there. In addition, the hydrogenation activity of these catalysts such as, for example, in the production polyhydric alcohols by hydrogenation of polybasic acid esters, can be insufficient for the achievement of high space-time yields. New catalysts that exhibit high activities, long lifetimes, and good mechanical stabilities are needed.

We have discovered novel compositions that are useful as catalysts for the preparation of methanol by hydrogenation of carbon monoxide and for the preparation of alcohols by the hydrogenation of carbonyl compounds. One aspect of our invention, therefore, is a catalyst comprising copper chromite, palladium, and lanthanum, wherein the palladium and lanthanum are deposited on the copper chromite. Our novel catalysts exhibit high catalytic activities and selectivities for methanol by the hydrogenation of carbon monoxide and/or carbon dioxide using feedstocks that contain both low and high concentrations of carbon dioxide. Our catalysts can show significant enhancement in CO hydrogenation activity over traditional copper chromite catalysts.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the claims, the singular forms "a," "an" and "the" include their plural referents unless the context clearly dictates otherwise. For example, reference to a "promoter," or a "reactor" is intended to include the one or more promoters or reactors. References to a composition or process containing or including "an" ingredient or "a" step is intended to include other ingredients or other steps, respectively, in addition to the one named.

The terms "containing" or "including", are synonymous with the term "comprising", and is intended to mean that at least the named compound, element, particle, or method step, etc., is present in the composition or article or method, but does not exclude the presence of other compounds, catalysts, materials, particles, method steps, etc., even if the other such compounds, material, particles, method steps, etc., have the same function as what is named, unless expressly excluded in the claims.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and the recited lettering can be arranged in any sequence, unless otherwise indicated.

The catalysts of the invention are hydrogenation catalysts. The term "hydrogenation catalyst", as used herein, is intended to have its commonly accepted meaning as would be understood by persons having ordinary skill in the art, that is, a substance that increases the rate of a hydrogenation reaction, without itself being consumed. The term "hydrogenation", as used herein, is also intended to have its commonly accepted meaning, that is, the reaction of hydrogen with an organic compound. For the purposes of the present invention, hydrogenation is understood to mean the addition of hydrogen to the double bonds or triple bonds of an unsaturated molecule such as, for example, carbon monoxide or a carbonyl compound, to produce a molecule having a higher degree of saturation such as, for example, methanol or an alcohol corresponding to the carbonyl compound. Also for the present invention, the term "hydrogenation" is intended to include "hydrogenolysis" in which the addition of hydrogen causes the rupture of bonds with the subsequent reaction of hydrogen with the molecular fragments. For example, the hydrogenation of carboxylic acid esters can be occur by the rupture of a carbon oxygen bond to form alcohol and aldehyde fragments, followed by hydrogenation of the aldehyde fragment to form a second alcohol corresponding to the aldehyde fragment. Thus, according to the present invention, the phrase "hydrogenation of an aldehyde or ketone", is understood to mean addition of hydrogen to the carbon-oxygen double bond to produce an alcohol corresponding to the aldehyde or ketone. Similarly, "hydrogenation of a carboxylic acid ester", is understood to mean the hydrogenolysis of the ester to produce an alcohol corresponding to the acid residue of the ester.

The catalysts of the invention comprise copper chromite. The term "copper chromite", as used herein, is intended have its commonly understood meaning in the art and includes copper chromite itself as represented by the general formula, $CuCr_2O_x$, non-stoichiometric mixed copper-chromium oxides, prepared by coprecipitation, and the various mixtures of copper chromite with copper metal, copper oxides, and chromium oxides, that may be formed during the catalyst manufacturing process and its subsequent use as a hydrogenation catalyst. For example, the copper chromite, as prepared, may comprise one or more of: copper (II) oxide, copper chromite ($CuCr_2O_4$), chromium trioxide ($CrO_3$), or chromic oxide ($Cr_2O_3$). In one embodiment of the invention, for example, the copper chromite may comprise about 24-26 weight % copper(II) oxide, about 65-67 weight % copper chromite, about 1 weight % chromium trioxide, about 1 weight % chromic oxide, and about 0-4 weight % graphite. During the hydrogenation process, a portion of the copper oxide may be reduced to copper metal. Thus, under hydrogenation conditions, the copper chromite of the invention can comprise mixtures of copper chromite, copper oxides, chromium oxides, and copper metal in various proportions. The copper chromite component of the catalysts can be prepared using conventional coprecipitation techniques well known in the art. In addition, the copper chromite may be further compounded with binders to aid in pellet formation or supported on additional support materials such as, for example, alumina, titania, carbon, graphite, zirconia, silica, and the like.

Typically, copper chromite having various molar ratios of copper to chromium may be conveniently prepared by coprecipitation of an aqueous solution of soluble copper and chromium compounds at a pH of 7 or above. The precipitate, typically, is filtered, washed with water, dried, and calcined in air to give the final catalyst. One example of the preparation of a copper chromite that can be used in the present invention is provided by Conner et al., *J. Amer. Chem. Soc.*, 53, 1091 (1931). In another example, copper chromite may be prepared in the following manner: Copper sulfate, $CuSO_4 5.H_2O$, and sodium dichromate, $Na_2Cr_2O_7.2H_2O$, can be combined with ammonium hydroxide to form a complex from which copper chromite may be prepared. The copper sulfate and sodium dichromate are dissolved in water to form a solution. To this solution ammonium hydroxide is added until the pH reaches 7.0 to 7.5. A precipitate is formed which is a complex and is believed to have the formula $Cu(OH)NH_4CrO_4$. This complex can be filtered, washed with water, dried, and calcined in air to give a copper chromite.

In another example, copper chromite catalyst can prepared by mixing respective solutions of copper nitrate ($Cu(NO_3)_2$) or another soluble copper (11) salt and a stoichiometric excess of a solution of ammonium chromate (($NH_4)_2CrO_4$) with at least a 3:1 weight ratio of ammonium chromate to copper nitrate. If desired, ammonium hydroxide or an equivalent soluble ammonium salt can be partially substituted for ammonium chromate. Precipitation of the copper-ammonium-chromate precipitate is effected by mixing of the two (i.e., copper nitrate and ammonium chromate) solutions. If ammonium hydroxide is to be present, it can be mixed with the ammonium chromate solution prior to mixing with the copper nitrate solution. The precipitate is separated from the mixture and dried by any suitable nondegradative means (e.g. by filtering and vacuum drying) to produce a product which is typically brown in color.

The copper chromite can have a wide range of copper and chromium content. For example, in one embodiment, the copper chromite can have copper content of about 15 to about 60 weight percent and a chromium content of about 15 to 60 weight percent, based on the total weight of the copper chromite. In another example, the copper chromite can have a copper content of about 30 to about 50 weight percent and a chromium content of about 30 to about 50 weight percent. Typically, the gram-atom ratio of copper to chromium will be about 1:10 to about 10:1. Additional examples of gram-atom ratios of copper to chromium are about 1:5 to about 5:1 and about 1:2 to about 2:1.

The catalyst also comprises palladium and lanthanum deposited on the copper chromite. By the term "deposited on", as used herein, it is understood that the palladium and lanthanum are placed on the surface of the copper chromite using conventional techniques, well-known in the art. A physical mixture of palladium and copper chromite, for example, would not have palladium deposited on the copper chromite. The palladium and lanthanum may be deposited on the copper chromite by contacting the copper chromite with an aqueous solution of compounds of palladium and lanthanum followed by filtering and drying the copper chromite at a temperature of about 40 to about 150° C. Typically, the palladium and lanthanum are dissolved in aqueous solution as their various water-soluble salts such as, for example, as their nitrates, carbonates, oxides, hydroxides, bicarbonates, formates, chromates, sulfates, acetates, benzoates, and the like. The dried copper chromite may then be calcined by heating at a temperature of about 350 to about 600° C. in the presence of air or an inert gas such as, for example, nitrogen or argon. The terms "calcined", "calcination", and "calcining", as used herein, are intended to have their commonly understood meaning in the art, that is, heating the catalyst composition or catalyst precursor composition to a temperature below its melting point to bring about a state of thermal decomposition or a phase transition of some or all of its components other than melting. During calcining, for example, organic compounds and ammonium salts can be decomposed and water of hydration can be expelled. In a variant of the above impregnation process, the solution of palladium and lanthanum may be deposited on the copper chromite by incipient wetness methods well-known to persons skilled in the art. The palladium and promoter may be deposited on the copper chromite at the same time or sequentially in any order. For example, the copper chromite can be impregnated first with a solution of a water soluble palladium compound. After filtering, drying, and calcining the palladium-impregnated copper chromite as described above, the copper chromite can be further impregnated with a aqueous solution of a lanthanum compound. The impregnated copper chromite can be dried and calcined as described previously.

The catalyst typically will comprise greater than 50 weight percent copper chromite, based on the total weight of the catalyst. Other examples of copper chromite levels within the catalysts of the invention, are at least 60 weight percent, at least 70 weight percent, at least 80 weight percent, and at least 90 weight percent. In one embodiment, for example, the catalyst can comprise about 85 to about 99.89 weight percent of copper chromite. Typically the surface area of the catalyst can range from about 20 to about 120 m²/g or, in another example, from about 30 to about 70 m²/g. The catalyst also will comprise about 0.1 to about 10 weight percent ruthenium, based on the total weight of the catalyst. Further representative examples of ruthenium content are about 0.5 to about 5 weight percent ruthenium and about 0.5 to about 2 weight percent ruthenium.

The hydrogenation catalyst, in addition to palladium, comprises about 500 to about 8000 parts per million, based on the total weight of the catalyst, of lanthanum. Other examples of lanthanum concentrations are about 1000 to about 6000 parts per million and about 1000 to about 5000 part per million. Other promoters may be present in addition to lanthanum, provided they do not negatively affect the performance of the catalyst. The term "promoter", as used herein, is understood to mean as substance that, when added in relatively small quantities to a catalyst, increases its activity. Representative examples of additional promoters include, but are not limited to one or more of sodium, potassium, calcium, barium, magnesium, and manganese.

For example, in one embodiment of the invention, the catalyst can comprise copper chromite having a gram-atom ratio of copper to chromium of about 1:2 to 2:1, and on which is deposited about 0.5 to about 5 weight percent palladium and about 1000 to about 5000 parts per million of lanthanum. As described previously, the above weight percent and parts per million are based on the total weight of the catalyst. Further, the above embodiment is understood to include the various other embodiments of copper chromite, palladium, other metals, and catalyst preparation conditions described hereinabove and in any combination.

In one embodiment, for example, the copper chromite has a gram-atom ratio of copper to chromium of about 1:1. In yet another example, the catalyst can comprise about 1 weight percent palladium. In still another example, the catalyst can comprise about 4000 parts per million to about 6000 parts per million of lanthanum. In still another example, the catalyst of the invention comprises: copper chromite having a gram-atom ratio of copper to chromium of about 1:2 to about 2:1, about 0.5 to about 1.5 weight percent palladium, and about 4000 to about 6000 parts per million of lanthanum; wherein the palladium and lanthanum are deposited on the copper chromite and the weight percent and parts per million are based on the total weight of the catalyst. As noted previously, the catalyst may also include the various embodiments of copper chromite, palladium, promoters, and catalyst preparation conditions described hereinabove and in any combination.

Our invention also provides catalyst consisting essentially of: copper chromite having a gram-atom ratio of copper to chromium of about 1:2 to about 2:1, about 0.5 to about 1.5 weight percent palladium, and about 4000 to about 6000 ppm lanthanum, wherein the palladium and lanthanum are deposited on the copper chromite. As noted above, this embodiment may also include the various embodiments of copper chromite, palladium, promoters, and catalyst preparation conditions described hereinabove and in any combination.

The phrase "consisting essentially of", as used herein, is intended to encompass a catalyst which primarily comprises copper chromite acid on which is deposited palladium and lanthanum. It is understood to exclude any elements that would substantially alter the essential properties of the catalyst to which the phrase refers. Although the catalyst of the present invention is based predominantly on copper chromite, palladium, and lanthanum, it is understood that the catalyst also can contain small amounts of other noble and non-noble metals, promoters, salts, binders, support materials, deposited thereon, as long as the catalyst properties are not affected significantly. For example, the catalyst may contain additional metals or metal compounds, in small amounts, i.e., generally less than 1000 parts per million, as long as the additional metal and/or metal compounds do not significantly affect the performance and properties of the catalyst. In another example, the copper chromite catalyst containing the palladium and lanthanum deposited thereon, may be further supported on additional support materials such as, for example, alumina, titania, zirconia, silica, and the like. In yet another example, catalyst compositions in which the palladium and promoter metals are not deposited on the copper chromite such as, for example, by the impregnation techniques discussed herein, are intended to be excluded. For example, a physical mixture or blend of the copper chromite, palladium compounds, and lanthanum compounds are intended to be excluded from the invention because in such a mixture, the palladium and promoter metals would not be deposited on the copper chromite. The above discussion is intended to merely provide examples of the kinds of modifications that may be employed; those of skill in the art will readily recognize others. For example, the catalyst can comprise copper chromite having a gram-atom ratio of copper to chromium of about 1:1, about 1 weight percent palladium and about 5000 parts per million of lanthanum. As noted above, the palladium and lanthanum are deposited on the copper chromite and the weight percent and parts per million are based on the total weight of the catalyst.

Our invention also can include a process for the preparation of a hydrogenation catalyst, comprising: contacting copper chromite with a solution of a palladium compound and a solution a lanthanum compound; drying the copper chromite, and calcining the dried copper chromite. The copper chromite may be contacted with an aqueous solution of compounds of palladium and lanthanum followed by filtering and drying the copper chromite at a temperature of about 40 to about 150° C., as described above. Typically, the palladium, lanthanum, and any additional promoter metals are dissolved in aqueous solution as their various water-soluble salts such as, for example, as their nitrates, carbonates, oxides, hydroxides, bicarbonates, formates, chromates, sulfates, acetates, benzoates, and the like. The dried copper chromite may then be calcined by heating at a temperature of about 350 to about 600° C. in the presence of air or an inert gas such as, for example, nitrogen or argon.

As described above, palladium and lanthanum may be contacted with or deposited on the copper chromite at the same time or sequentially in any order. For example, the copper chromite can be impregnated first with a solution of a water soluble palladium compound. After filtering, drying, and calcining the palladium-impregnated copper chromite as described above, the copper chromite can be further impregnated with an aqueous solution of a lanthanum compound. The impregnated copper chromite can be dried and calcined as described previously. Thus, the above process may further comprise (i) contacting copper chromite with a solution of a palladium compound; (ii) drying the copper chromite; (iii) calcining the dried copper chromite from step (ii); (iv) contacting the calcined copper chromite from step (iii) with a solution of a lanthanum compound; (v) drying the copper chromite from step (iv); and (vi) calcining the dried copper chromite from step (v). The drying steps (ii) and (v) independently can be carried out at a temperature of about 40 to about 150° C. and the calcination steps (iii) and (vi) independently can be carried out at a temperature of about 400 to about 600° C.

The catalyst prepared by the process of the invention is understood to include the various embodiments of copper chromite, palladium, and lanthanum as described above and in any combination. For example, the catalyst can comprise about 0.1 to about 10 weight percent palladium and about 500 to about 8000 parts per million of lanthanum. In another example, the catalyst can comprise about 0.5 to about 2 weight percent palladium and about 1000 to about 5000 parts per million of lanthanum. In still another example, the copper chromite can comprise a gram-atom ratio of copper to chromium of about 1:2 to about 2:1.

Our catalysts are useful for the hydrogenation of carbon monoxide and/or carbon dioxide to methanol. Our invention, therefore, includes a process for the preparation of methanol, comprising: contacting a gaseous feed comprising hydrogen, carbon monoxide, and optionally carbon dioxide, with a catalyst comprising copper chromite, palladium and lanthanum; wherein the palladium and lanthanum are deposited on the copper chromite. The catalyst is understood to include the various embodiments of copper chromite, palladium, and lanthanum as described above and in any combination. For example, the catalyst can comprise about 0.1 to about 10 weight percent palladium based on the total weight of the catalyst. Other examples of palladium weight percentage ranges for the catalyst are about 0.5 to about 5 weight percent and about 0.5 to about 2 weight percent.

As described above, the catalyst also can comprise about 500 to about 8000 parts per million, based on the total weight of the catalyst, of lanthanum. Additional representative ranges of lanthanum include about 1000 to about 5000 parts per million and about 4000 to about 6000 parts per million.

The catalyst typically will comprise greater than 50 weight percent copper chromite, based on the total weight of the catalyst. Other examples of copper chromite levels within the catalysts of the invention, are at least 60 weight percent, at least 70 weight percent, at least 80 weight percent, and at least 90 weight percent. In one example, the catalyst comprises about 85 to about 99.5 weight percent of copper chromite. In another embodiment, the copper chromite can have a copper content of about 15 to about 60 weight percent and a chromium content of about 15 to about 60 weight percent, based on the total weight of the copper chromite. In yet another example, the copper chromite can have a copper content of about 30 to about 50 weight percent and a chromium content of about 30 to about 50 weight percent. Typically, the gram-atom ratio of copper to chromium will be about 1:10 to about 10:1. Additional examples of gram-atom ratios of copper to chromium are about 1:5 to about 5:1 and about 1:2 to about 2:1.

In another embodiment of our methanol process, for example, the catalyst comprises copper chromite having a gram-atom ratio of copper to chromium of about 1:2 to 2:1, about 0.5 to about 1.5 weight percent palladium and about 4000 to about 6000 parts per million of lanthanum, based on the total weight of the catalyst.

The catalyst is contacted with a gaseous feed comprising hydrogen, carbon monoxide, and optionally, carbon dioxide. Such mixtures are commonly referred to as "syngas" and can be produced by blending the individual gases or by any of a number of methods known in the art including steam or carbon dioxide reforming of carbonaceous materials such as natural gas or petroleum derivatives; and the partial oxidation or gasification of carbonaceous materials, such as petroleum residuum, bituminous, subbituminous, and anthracitic coals and cokes, lignite, oil shale, oil sands, peat, biomass, petroleum refining residues or cokes, and the like.

The hydrogen, carbon monoxide, and/or carbon dioxide content of the syngas may be adjusted for efficiency of conversion. For example, the gaseous feed to the catalyst can have a molar ratio of hydrogen to carbon oxides ($CO+CO_2$) in the range of from about 0.5:1 to about 20:1, preferably in the range of from about 2:1 to about 10:1. In another embodiment, the gaseous feed can have a molar ratio of hydrogen ($H_2$) to carbon monoxide (CO) of at least 2:1.

Carbon dioxide may be optionally present in an amount of not greater than 50% by weight, based on total volume of the gaseous feed. Additional examples of carbon dioxide levels in the gaseous feed include, but are not limited to, about 1 to about 25 weight percent carbon dioxide, about 1 to about 5 weight percent carbon dioxide, and about 10 to about 20 weight percent carbon dioxide.

The $CO_2$ content, relative to that of CO, in the gaseous feed can be high enough so as to maintain an appropriately high reaction temperature and to minimize the amount of undesirable by-products such as, for example, paraffins. At the same time, the relative $CO_2$ content should not be too high so as to reduce methanol yield. Typically, the gaseous feed will contain $CO_2$ and CO at a molar ratio of from about 0.5 to about 1.2 or, in another example, from about 0.6 to about 1.0.

The process of the invention may be carried out over a range of temperatures. The gaseous mixture of carbon monoxide, hydrogen, and optionally, carbon dioxide typically is contacted with the catalyst at a temperature of about 150 to about 350° C. and at a pressure of about 10 to about 100 bars absolute ("bara"). In another example, the gaseous mixture may be contacted with the catalyst at temperature of about 180 to about 250° C. and at a pressure of about 30 to about 70 bara.

The methanol process can be carried out in any type of methanol synthesis plant that is well known to persons skilled in the art and many of which are widely practiced on a commercial basis. Examples of such processes include batch processes and continuous processes. Tubular bed processes and fluidized bed processes are examples types of continuous processes. A number of different process technologies are known for synthesizing methanol such as, for example, the ICI (Imperial Chemical Industries) or Haldor Topsoe processes, the Lurgi process, and the Mitsubishi process. Liquid phase processes are also well known in the art. For example, the gaseous feed and catalyst of the process according to the present invention may be contacted in a fixed bed or liquid slurry phase reactor.

The syngas stream is typically supplied to a methanol reactor at the pressure of about 25 to about 140 bara, depending upon the process employed. The syngas then reacts over a catalyst to form methanol. The reaction is exothermic; therefore, heat removal is ordinarily required. The raw or impure methanol is then condensed and may be purified to remove impurities such as higher alcohols including ethanol, propanol, and the like, or used without purification. The uncondensed vapor phase comprising unreacted syngas feedstock typically is recycled to the methanol process feed.

The hydrogenation process may be conducted at various gas hourly space velocities depending upon the type of process that is used. In one embodiment, for example, the gas hourly space velocity of flow of gas through the catalyst bed is in the range of from about 50 $hr^{-1}$ to about 50,000 $hr^{-1}$. In other examples, the gas hourly space velocity of flow of gas through the catalyst bed is about 250 $hr^{-1}$ to about 25,000 $hr^{-1}$, or about 500 $hr^{-1}$ to about 15,000 $hr^{-1}$.

Our invention also may be used for the preparation of alcohols from organic carbonyl compounds such as, for example, an aliphatic, cycloaliphatic and aromatic carbonyl compound by hydrogenation in the presence of one of the catalysts described hereinabove. Thus, another aspect of the invention is a process for hydrogenating a carbonyl compound to an alcohol, comprising contacting at least one carbonyl compound with hydrogen in the presence of a catalyst comprising copper chromite, palladium and lanthanum; wherein the palladium and lanthanum are deposited on the copper chromite.

The catalyst is understood to include the various embodiments of copper chromite, palladium, and lanthanum as described above and in any combination. For example, the catalyst can comprise about 0.1 to about 10 weight percent palladium based on the total weight of the catalyst. Other examples of palladium weight percentage ranges for the catalyst are about 0.5 to about 5 weight percent and about 0.5 to about 2 weight percent.

As described above, the catalyst also comprises about 500 to about 8000 parts per million, based on the total weight of the catalyst, of lanthanum. Additional representative ranges of lanthanum include about 1000 to about 5000 parts per million and about 4000 to about 6000 parts per million. The catalyst typically can comprise about 85 to about 99.5 weight percent of copper chromite, based on the total weight of the catalyst. The copper chromite also can have a copper content of about 15 to about 60 weight percent and a chromium content of about 15 to 60 weight percent, based on the total weight of the copper chromite. In another example, the copper chromite can have a copper content of about 30 to about 50 weight percent and a chromium content of about 30 to about 50 weight percent. Generally, the gram-atom ratio of copper to chromium can be about 1:10 to about 10:1. Additional examples of gram-atom ratios of copper to chromium are about 1:5 to about 5:1 and about 1:2 to about 2:1.

The carbonyl compound can comprise an aldehyde, ketone, carboxylic acid ester, or combinations thereof. Examples of the carbonyl compounds which may be hydrogenated include aliphatic, cycloaliphatic and aromatic aldehydes, carboxylic acid esters, and ketones containing up to about 50 carbon atoms. Acetophenone, benzophenone, acetone, methyl butyl ketone, benzaldehyde, crotonaldehyde, acetaldehyde and butyraldehyde are typical ketones and aldehydes which may be converted to alcohols according to the present invention. Thus, one aspect of the novel hydrogenation process provides a process for the preparation of an alcohol by the hydrogenation of an aliphatic, cycloaliphatic or aromatic aldehyde, carboxylic acid ester, or ketone in the presence of one of the catalysts described hereinabove under hydrogenation conditions of temperature and pressure.

The carbonyl compound employed in the hydrogenation process can be an aliphatic, cycloaliphatic or aromatic ester of an aliphatic or cycloaliphatic mono- or polycarboxylic acid. In one embodiment, for example, the carbonyl compound can comprise an alkyl carboxylate comprising the residue of at least one hydroxy compound containing from 1 to about 40 carbon atoms. Representative examples, of hydroxy compounds are methanol, ethanol, propanol, 1-butanol, 2-butanol, isobutanol, 2-ethylhexanol, 2,2-dimethyl-1,3-propanediol, ethylene glycol, propylene glycol, 1,4-butanediol, 1,6-hexanediol, 1,10-decanediol, cyclohexanol, 4-methylcyclohexanemethanol, diethylene glycol, glycerin, trimethylolpropane, and combinations thereof.

The carboxylic acid residue of the alkyl carboxylate is not important to our process provided that each oxycarbonyl group hydrogenated is bonded to an aliphatic, aralkyl, aryl, or cycloaliphatic carbon atom. The alkyl carboxylate, for example, may comprise the residue of at least one aliphatic, cycloaliphatic, aryl, or aralkyl carboxylic acid having from 1 to 40 carbon atoms. In another example, the alkyl carboxylate, can comprise the residue of at least one aliphatic or cycloaliphatic carboxylic acid. Typical examples of cycloaliphatic carboxylic acids are 1,2-cyclohexanedicarboxylic acid, 1,3-cyclohexanedicarboxylic acid, 1,4-cyclohexanedicarboxylic acid, and combinations thereof. The aliphatic acid can be straight- or branched-chain, saturated or unsaturated and unsubstituted or substituted, for example, with a wide variety of substituents such as halogen, hydroxy, alkoxy, amino, substituted amino, acylamido, aryl, cycloalkyl, etc. The main chain of the aliphatic acid also may contain hetero atoms such as oxygen, sulfur and nitrogen atoms. In another embodiment of the present invention, esters of arylcarboxylic acids such as alkyl benzoates are excluded from the term "alkyl carboxylate", whereas esters of aralkylcarboxylic acids, such as alkyl phenylacetates are included within the meaning of alkyl carboxylates.

Additional representative examples of aliphatic and cycloaliphatic acids include, but are not limited to, formic, acetic, propionic, glycolic, butyric, valeric, hexanoic, heptanoic, octanoic, nonanoic, decanoic, undecanoic, lauric, tridecanoic, myristic, pentadecanoic, palmitic, heptadecanoic, stearic, oleic, linoleic, linolenic, nonadecanoic, eicosanoic, arachidonic, heneicosanoic, docosanoic, tetracosanoic, octacosanoic, triacontanoic, dotriacontanoic, acrylic, methacrylic, crotonic, 3-butenoic, cyclobutanecarboxylic, 2-norbornane-carboxylic, malonic, succinic, glutamic, maleic, glutaconic, adipic, pimelic, suberic, azelaic, sebacic, 1,2,4-hexanetricarboxylic, 1,2-, 1,3-, and 1,4-cyclohexanedicarboxylic, 2,6- and 2,7-octahydronaphthalenedicarboxylic, 3-1(2-carboxyethyl)thiolbutyric, and the line. Typical examples of esters useful in the invention process, based on the combination of the hydroxy compounds and carboxylic acids described hereinabove, include, but are not limited to, methyl acetate, methyl formate, methyl glycolate, ethyl acetate, methyl n-octa-decanoate, isobutyl decanoate, t-butylnonoate, phenyl acetate, 2-naphthyl propionate, dimethyl oxalate, diethyl oxalate, dimethyl malonate, diethyl malonate, dimethyl succinate, diethyl succinate, dimethyl adipate, diethyl adipate, methyl cyclohexylcarboxylate, dimethyl 1,4-cyclohexanedicarboxylate, ethyl cyclohexylacetate, isopropyl acetate, and sec-butyl propionate. The catalysts of the invention can be used, for example, to hydrogenate an alkyl glycolate, such as methyl glycolate, to ethylene glycol.

The amount of catalyst required can be varied substantially depending on a number of factors such as, for example, the composition and physical form of the catalyst and the hydrogenation conditions and mode of operation being used. The hydrogenation conditions of pressure and temperature also can be varied depending not only on one another but also on the activity of the catalyst, the mode of operation, selectivity considerations and the desired rate of conversion. Carbonyl compounds may be hydrogenated to their corresponding alcohols according to the process of the invention using temperatures in the range of about 150° C. to about 350° C. and hydrogen pressures in the range of about 40 to 450 bars absolute ("bara"). However, since hydrogenation rates generally increase with temperature, it may desirable to operate in the range of about 180 to about 300° C. and at a pressure of about 200 to about 350 bara to maximize both conversion rates and utilization of the commercial hydrogenation facility. While rates and conversions generally also increase with increasing pressure, the energy costs for compression of hydrogen, as well as the increased cost of high-pressure equipment render the use of the lowest pressure practical desirable.

The hydrogen gas used in the process may comprise fresh gas or a mixture of fresh gas and recycle gas. The hydrogen gas can be a mixture of hydrogen, optional minor amounts of components such as CO and $CO_2$, and inert gases, such as argon, nitrogen, or methane, containing at least about 70 mole % of hydrogen. For example, the hydrogen gas may contain at least 90 mole % or, in another example, at least 97 mole %, of hydrogen. The hydrogen gas may be obtained from any of the common sources well known in the art such as, for example, by partial oxidation or steam reforming of natural gas. Pressure swing absorption can be used if a high purity hydrogen gas is desired. If gas recycle is utilized in the process, then the recycle gas will normally contain minor amounts of one or more products of the hydrogenation reaction which have not been fully condensed in the product recovery stage downstream from the hydrogenation zone. Thus, when using gas recycle in the process of the invention, the gas recycle stream will typically contain a minor amount of an alkanol, e.g., methanol.

The ester hydrogenation process of this invention may be carried out in the absence or presence of an inert solvent, i.e., a solvent for the ester being hydrogenated which does not affect significantly the activity of the catalyst and does not react with the hydrogenation product or products. Examples of such solvents include alcohols such as ethanol and lauryl alcohol; glycols such as mono-, di- and tri-ethylene glycol; hydrocarbons such as hexane, cyclohexane, octane and decane; and aromatic ethers such as diphenyl ether, etc.

The hydrogenation process may be carried out as a batch, semi-continuous or continuous process. Examples of suitable reactor types include, but are not limited to, stirred tank, continuous stirred tank, trickle bed, tower, slurry, and tubular reactors. The catalyst should be dispersed throughout the reaction media to effectively assist contact of reactants and catalyst. For example, the catalyst may be introduced as small particles that can be slurried or suspended in an agitated reaction mixture. Typically, the catalyst is used in the form of a fixed bed or in slurry form through which reactants are continuously circulated in the liquid or gas phase.

In batch operation a slurry of the catalyst in the reactant and/or an inert solvent in which the reactant has been dissolved is fed to a pressure vessel equipped with means for agitation. The pressure vessel is then pressurized with hydrogen to a predetermined pressure followed by heating to bring the reaction mixture to the desired temperature. After the hydrogenation is complete, the reaction mixture is removed from the pressure vessel, the catalyst is separated by filtration and the product is isolated, for example, in a distillation train.

Continuous operation can utilize a fixed bed using a larger particle size of catalyst, e.g., catalyst pellets. The catalyst bed may be fixed in a tubular or columnar, high pressure reactor and the liquid reactant, dissolved in an inert solvent if necessary or desired, slowly fed continuously above the bed at elevated pressure and temperature and crude product removed from the base of the reactor. Another mode of continuous operation utilizes a slurry of the catalyst in an agitated pressure vessel which is equipped with a filter leg to permit continuous removal of a solution of product in unreacted ester and/or an inert solvent. In this manner, a liquid reactant or reactant solution can be continuously fed to and product solution continuously removed from an agitated pressure vessel containing an agitated slurry of the catalyst.

The hydrogenation process provided by the invention can be used for converting dialkyl cyclohexanedicarboxylic acid esters to cyclohexane-dimethanols. Our invention, therefore, also provides a process for the preparation of a cyclohexanedimethanol comprising contacting at least one dialkyl cyclohexanedicarboxylate with hydrogen in the presence of a catalyst comprising copper chromite, palladium and lanthanum; wherein the palladium and lanthanum are deposited on the copper chromite. The term "cyclohexane-dimethanol", as used herein, means one or more compounds having a cyclohexane ring bearing 2 hydroxymethyl substituents. Examples of cyclo-hexanedimethanols include 1,4-cyclohexanedimethanol, 1,3-cyclohexane-dimethanol, 1,2-cyclohexanedimethanol, and 1,1-cyclohexanedimethanol. The cyclohexanedicarboxylate ester reactant may be any ester of a cyclohexane-dicarboxylic acid. For example, the cyclohexanedimethanol may be 1,4-cyclo-hexanedimethanol and the cyclohexanedicarboxylate ester is a dialkyl 1,4-cyclohexanedicarboxylate comprising one or more residues of a hydroxy compound containing from 1 to about 20 carbon atoms. Examples of hydroxy compound residues are any mono- or polyhydroxy compound such as methanol, ethanol, butanol, 2-butanol, 2-ethylhexanol, 2,2-dimethyl-1,3-propanediol, ethylene glycol, propylene glycol, 1,4-butanediol, 1,6-hexanediol, 1,10-decanediol, cyclohexanol, benzyl alcohol, diethylene glycol, glycerin, and trimethylolpropane.

Dialkyl cyclohexanedicarboxylates may be obtained commercially as a mixture of cis and trans isomers or as purified cis or trans isomers. Dimethyl 1,4-cyclohexanedicarboxylate, for example, may be used as a mixture of cis and trans isomers, although pure cis and trans grades of dimethyl 1,4-cyclohexane-dicarboxylate may be used if desired. For example, in one embodiment, the alkyl carboxylate comprises dimethyl 1,4-cyclohexanedicarboxylate having a cis:trans molar ratio of about 1:1 to about 2:1. In a typical bulk sample of commercially available dimethyl 1,4-cyclohexanedicarboxylate, the molar cis:trans isomer ratio is about 2:1 to about 1.7:1. The 1,4-cyclohexanedimethanol product, in turn, can have a cis:trans molar ratio of about 0.7:1 to about 2:1.

The hydrogenation conditions of pressure and temperature may be varied depending not only on one another but also on the activity of the catalyst, the mode of operation, selectivity considerations, and the desired rate of conversion. The process typically is conducted at temperatures in the range of about 150° C. to about 350° C. and pressures in the range of about 40 to about 450 bars absolute (abbreviated herein as "bara"). Further examples of temperatures and pressures at which the process of the invention may be operated are about 175° C. to about 300° C. at about 200 to about 380 bara, and about 200° C. to about 250° C. at about 300 to about 350 bara. While rates and conversions generally also increase with increasing pressure, the energy costs for compression of hydrogen, as well as the increased cost of high-pressure equipment generally can make the use of the lowest pressure practical desirable.

The process of the invention may be carried out in the absence or presence of an inert solvent, i.e., a solvent for the cyclohexanedicarboxylate ester being hydrogenated which does not affect significantly the activity of the catalyst and does not react with the hydrogenation product or products. Examples of such solvents include alcohols such as ethanol and lauryl alcohol; glycols such as mono-, di- and tri-ethylene glycol; hydrocarbons such as hexane, cyclohexane, octane and decane; and aromatic ethers such as diphenyl ether, etc. It is often economically desirable, however, to conduct the process in the absence of solvent and use the neat, molten cyclohexanedicarboxylate ester alone or as a mixture with the cyclohexanedimethanol and other hydrogenation products as the feed to the process.

The process may be carried out as a batch, semi-continuous or continuous process and may utilize a variety of reactor types. Examples of suitable reactor types include, but are not limited to, stirred tank, continuous stirred tank, slurry, tubular, fixed bed, and trickle bed. The term "continuous" as used herein means a process wherein reactants are introduced and products withdrawn simultaneously in an uninterrupted manner. By "continuous" it is meant that the process is substantially or completely continuous in operation in contrast to a "batch" process. "Continuous" is not meant in any way to prohibit normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which no material is fed or removed into the reactor. For example, in a batch operation, a slurry of the catalyst in the cyclohexanedicarboxylate ester and/or an inert solvent in which the cyclohexanedicarboxylate ester has been dissolved is fed to a pressure vessel equipped with means for agitation. The pressure vessel is then pressurized with hydrogen to a predetermined pressure followed by heating to bring the reaction mixture to the desired temperature. After the hydrogenation is complete, the reaction mixture is removed from the pressure vessel, the catalyst is separated by filtration and the cyclohexane-dimethanol product is isolated, for example, in a distillation train. The term "semicontinuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses.

For economic and operability reasons, the process may be operated as a continuous process which comprises contacting hydrogen and the catalyst in a fixed bed or a liquid slurry phase reactor. Continuous operation may utilize a fixed bed with a larger particle size of catalyst such as, for example, granules, pellets, various multilobal shaped pellets, rings, or saddles that are well known to skilled persons in the art.

As an example of a continuous process, the catalyst bed may be fixed in a high pressure, tubular or columnar reactor and the liquid cyclohexane-dicarboxylate ester, dissolved in an inert solvent if necessary or desired, fed continuously into the top of the bed at elevated pressure and temperature, and the crude hydrogenation product removed from the base of the reactor. Alternatively, it is possible to feed the cyclohexanedicarboxylate ester into the bottom of the bed and remove the crude product from the top of the reactor. It is also possible to use 2 or more catalyst beds or hydrogenation zones connected in parallel or in series to improve conversion, to reduce the quantity of catalyst, or to by-pass a catalyst bed for periodic maintenance or catalyst removal. Another mode of continuous operation utilizes a slurry of the catalyst in an agitated pressure vessel which is equipped with a filter leg to permit continuous removal of a solution of product in unreacted ester and/or an inert solvent. In this manner a liquid reactant or reactant solution can be continuously fed to and product solution continuously removed from an agitated pressure vessel containing an agitated slurry of the catalyst.

The process may be conducted in the liquid phase, the vapor phase, or as combination of the liquid and vapor phase. For example, the process may be carried in the vapor phase as described, for example, in U.S. Pat. No. 5,395,987. In one example of a vapor phase operation, the process of the invention may be operated using vaporous feed conditions by feeding the cyclohexanedicarboxylate ester in essentially liquid free, vaporous form to a hydrogenation zone comprising the catalyst of the invention. Hence, the feed stream is introduced into the hydrogenation zone at a temperature which is above the dew point of the mixture. The process may be operated so that vapor phase conditions will exist throughout the hydrogenation zone. Such a vapor phase process often has the advantage of lower operating pressures in comparison to liquid phase process which can reduce the construction and operating costs of a commercial plant.

In a vapor phase process, it is desirable but not essential to avoid contact of the cyclohexanedicarboxylate ester liquid with the catalyst to prevent localized overheating of and damage to the catalyst from the exothermic nature of the hydrogenation reaction. In conventional liquid phase hydrogenation processes, this danger is lessened by the greater heat capacity of the liquids surrounding the catalyst. It is desirable, therefore, that the vaporous feed stream is maintained above its dew point so that the cyclohexanedicarboxylate ester is present in the vapor phase at the inlet end of the catalyst. This means that the composition of the vaporous feed mixture must be controlled so that, under the selected operating conditions, the temperature of the mixture at the inlet end of the catalyst bed is always above its dew point at the operating pressure. The term "dew point", as used herein, means that temperature at which a gas or a mixture of gases is saturated with respect to a condensable component. This dew point liquid will normally contain all the condensable components of the vapor phase, as well as dissolved gases, in concentrations that satisfy vapor/liquid equilibrium conditions. Typically the feed temperature of the vaporous feed mixture to the hydrogenation zone is from about 5° C. to about 10° C. or more above its dew point at the operating pressure.

A convenient method of forming a vaporous mixture for use in a vapor phase process is to spray liquid cyclohexanedicarboxylate ester or a cyclohexanedicarboxylate ester solution into a stream of hot hydrogen-containing gas to form a saturated or partially saturated vaporous mixture. Alternatively, such a vapor mixture can be obtained by bubbling a hot hydrogen-containing gas through a body of the liquid 1,4-cyclohexane-dicarboxylate ester or cyclohexanedicarboxylate ester solution. If a saturated vapor mixture is formed it should then be heated further or diluted with more hot gas so as to produce a partially saturated vaporous mixture prior to contact with the catalyst. To maintain the vaporous feed stream above its dew point at the inlet end of a catalyst bed at the operating pressure, the hydrogen-containing gas:cyclohexanedicarboxylate ester molar ratio is desirably about 10:1 to about 8000:1 or about 200:1 to about 1000:1.

For a vapor phase process, the cyclohexanedicarboxylate ester, typically, is fed to the catalyst bed at a liquid hourly space velocity of about 0.05 to about 4.0 $h^{-1}$. Liquid hourly space velocity, as used herein, is defined as the liquid volume of the hydrogenatable material fed to the vaporization zone per volume of the hydrogenation catalyst per unit time (typically hours). Thus, for the above liquid hourly space velocity, the cyclohexanedicarboxylate ester is fed to the vaporization zone at a rate which is equivalent to, per unit volume of catalyst, from about 0.05 to about 4.0 unit volumes of cyclohexanedicarboxylate ester per hour (i.e. about 0.05 to about 4.0 $m^3$ $h^{-1}$ per $m^3$ of catalyst). In another example, the liquid hourly space velocity is from about 0.1 $h^{-1}$ to about 1.0 $h^{-1}$.

EXAMPLES

The invention is further illustrated by the following examples. The palladium copper chromite catalysts were prepared by wet impregnation of commercial E403TU copper chromite obtained from BASF Corporation (Lot 68D-10E). The copper chromite had a surface area of 30 m$^2$/g, and contained approximately 24-26 weight % copper(II) oxide, 65-67 weight % copper chromite, 1 weight % chromium trioxide, 1 weight % chromic oxide, and 0-4 weight % graphite. The copper content was about 37 weight % copper and the chromium content about 31 weight %. The gram-atom ratio of copper to chromium was approximately 1:1. Impregnation was done with a solution of Pd(NH$_3$)$_4$(NO$_3$)$_2$ obtained from Alfa (lot G22Q16). This solution contained 4.6% Pd. The catalyst was dried at 80° C. and calcined at 500° C. for 2 hours. The calcination heating rate was 2° C./min. This treatment gave a modified copper chromite catalyst containing 1% palladium metal. The palladium modified copper chromite catalyst was further impregnated with a solution of lanthanum nitrate to a target level of either 1000 ppm or 5000 ppm. This treatment was again followed by drying at 80° C. and calcination at 500° C. for 2 hours.

Catalyst activity was measured using a system of parallel, fixed-bed, quartz microreactors with a 2-mm inside diameter. These reactors are suitable for testing from 25 to 250 mg of catalyst. Each reactor was charged with 25 microliters of catalyst for these experiments. Catalysts were reduced by heating the reactors at a rate of 5° C./min to 220° C. in a flow of 80 volume %/20 volume % nitrogen and hydrogen. The reactors were pressurized to 3.45 MPa at 0.5 MPa/min and then pure hydrogen feed was started. The reactors were maintained under these conditions for four hours.

Methanol synthesis was conducted at temperatures ranging from 180° C. to 240° C. at a pressure of 5.5 MPa. Two synthesis gas feed compositions were employed for these tests. The lean $CO_2$ gas mixture contained 68 weight % hydrogen, 29.3 weight % CO, and 2.7 weight % $CO_2$. The $CO_2$ rich gas stream contained 73.5 weight % hydrogen, 6.7 weight % CO, and 19.8 weight % $CO_2$. Both gas streams approximate an equivalent stoichiometric ratio of $H_2$/CO of 2.0 after adjusting for the influence of the water gas shift reaction. A gas feed rate (GHSV) of 12000 hr$^{-1}$ was selected to keep conversion with the most active catalysts below 50% and avoid thermodynamic equilibrium effects.

Products were analyzed by on-line gas chromatography using a Varian 4900 Micro-GC equipped with a thermal conductivity detector. A 5 A molecular sieve was used with He carrier in one channel to separate $CH_4$, $CO_2$, ethane, water, propane, dimethyl ether (DME), and methanol. Another channel employed PPQ and a nitrogen carrier to separate $H_2$, $O_2$, $CH_4$ and CO from the He internal standard. The product from every reactor was sampled twice at each temperature with the time interval between analyses being approximately three to four hours. The data from these experiments are presented in Tables 1-8. The temperatures shown in Tables 1-8 represent the temperatures of the catalyst bed which, under the conditions of the experiments, was approximately isothermal. The quantities of hydrogen, carbon monoxide, carbon dioxide, dimethyl ether, and methanol are provided in Tables 1-8 as weight percentages of the reactor effluent.

The relative activity of the subject catalysts was determined by comparing the amount of methanol in the reactor product, and the total conversion of CO and $CO_2$ achieved in the reaction. The activity of various Pd/La promoted copper chromite catalysts for methanol production is shown in Table 1. Tables 2 and 3 show the data for the individual measurements of activity of the reference copper zinc catalysts, Table 4 shows the data for copper zinc catalysts containing various promoters, and Table 5 shows the data for copper zinc catalysts promoted with palladium in combination with lanthanum and other promoters. Table 1 shows that the activity of the Pd/La promoted copper chromite catalyst at the 5000 ppm La level (see, for example, Table 1, Examples 2, 4, 16, and 19) is comparable to the activity obtained with two unpromoted reference copper zinc methanol catalysts at about 240° C. (CuZn A and CuZn B), shown in Tables 2 and 3 (see, for example, Table 2, Comparative Examples 5-16 and 56-65; and Table 3, Comparative Examples 130-137 and 165-171), and the same reference copper zinc catalysts modified with the Pd/La promoter combination, shown in Table 5 (see, for example, Comparative Examples 481, 489, 494, 499, 500, 503, 504, and 512). Further inspection of Table 1 reveals that methanol production is reduced when the syngas contains a high level of $CO_2$, but significant methanol production activity remains (see, for example, Examples 2 and 4 versus 16 and 19).

The high activity of lanthanum promoted palladium copper chromite catalysts for methanol synthesis is unexpected in view of the fact that copper chromite alone has a low activity for methanol synthesis, and addition of either palladium or various promoters to the copper chromite does not give a meaningful improvement in the activity of the base catalyst. The low activity of these comparison catalysts is shown in Tables 6, 7, and 8. Unmodified copper chromite, shown in Table 6, gave a maximum methanol concentration in the product of 1.5% at 240° C. when feeding the low $CO_2$ syngas (see, for example, Comparative Examples 955-956). Results in the high $CO_2$ syngas again were about half the values obtained with the low $CO_2$ feed (see, for example, Comparative Examples 963-964). This is considerably lower than the activity obtained with the lanthanum promoted palladium catalyst prepared from this base catalyst.

Impregnation of the base copper chromite catalyst with 1% palladium actually reduced the activity of the resulting catalyst for methanol synthesis. As shown in Table 7, only about 0.8% methanol was produced in the high $CO_2$ syngas at about 240° C. (see, for example, Comparative Examples 1006-1008), and no detectable methanol was produced in the low $CO_2$ syngas (see, for example, Comparative Examples 973-974). The addition of various promoters shown in Table 8, but not palladium, to the base copper chromite had a generally negative impact on the activity of the catalyst (see, for example, Comparative Examples 1112-1115, 1118-1125, 1127-1128, and 1176-1178). The addition of 1000 ppm rubidium to the copper chromite catalyst, however, improved the activity under high $CO_2$ conditions compared to the unpromoted copper chromite catalyst or a copper chromite catalyst promoted with palladium alone and palladium with non-lanthanum promoters (see, for example, Comparative Examples 963-964, 1006-1027 and 1176-1178).

TABLE 1

Activity of La-Promoted 1% Palladium on Copper Chromite Catalysts for Methanol Production

| Ex. No. | $CO_2$ Level | Promoter | Promoter (ppm) | Temp (° C.) | $H_2$ wt % | CO wt % | $CO_2$ wt % | DME wt % | MeOH wt % | CO & $CO_2$ conv % |
|---|---|---|---|---|---|---|---|---|---|---|
| 1 | Low | La | 1000 | 238.5 | 66.76 | 28.55 | 2.47 | 0.00 | 0.56 | 3.45 |
| 2 | Low | La | 5000 | 238.4 | 56.18 | 23.86 | 3.14 | 0.00 | 14.76 | 32.26 |
| 3 | Low | La | 1000 | 238.4 | 66.88 | 28.41 | 2.47 | 0.00 | 0.58 | 3.87 |
| 4 | Low | La | 5000 | 238.3 | 56.05 | 23.84 | 3.14 | 0.00 | 14.90 | 32.48 |
| 5 | Low | La | 1000 | 228.6 | 66.89 | 28.60 | 2.47 | 0.00 | 0.38 | 2.78 |
| 6 | Low | La | 5000 | 228.3 | 59.85 | 25.64 | 2.87 | 0.00 | 9.72 | 23.12 |
| 7 | Low | La | 5000 | 228.3 | 60.07 | 25.74 | 2.86 | 0.00 | 9.42 | 22.47 |
| 8 | Low | La | 1000 | 228.3 | 67.01 | 28.50 | 2.47 | 0.00 | 0.37 | 3.10 |
| 9 | Low | La | 1000 | 198.7 | 66.95 | 28.82 | 2.47 | 0.00 | 0.11 | 1.62 |
| 10 | Low | La | 1000 | 198.7 | 67.06 | 28.72 | 2.47 | 0.00 | 0.10 | 1.74 |
| 11 | Low | La | 5000 | 198.6 | 66.52 | 28.61 | 2.42 | 0.00 | 0.78 | 3.35 |
| 12 | Low | La | 5000 | 198.3 | 66.37 | 28.72 | 2.44 | 0.00 | 0.80 | 3.42 |
| 13 | Low | La | 5000 | 178.6 | 66.78 | 28.88 | 2.44 | 0.00 | 0.25 | 1.96 |
| 14 | Low | La | 5000 | 178.6 | 66.81 | 28.85 | 2.44 | 0.00 | 0.24 | 2.01 |
| 15 | High | La | 1000 | 240.1 | 72.14 | 6.68 | 18.56 | 0.00 | 0.94 | 6.05 |
| 16 | High | La | 5000 | 240.0 | 67.11 | 2.95 | 19.61 | 0.00 | 8.39 | 27.04 |
| 17 | High | La | 1000 | 240.0 | 72.08 | 6.72 | 18.59 | 0.00 | 0.92 | 5.59 |
| 18 | High | La | 1000 | 240.0 | 72.10 | 6.71 | 18.59 | 0.00 | 0.92 | 5.91 |
| 19 | High | La | 5000 | 239.9 | 67.28 | 2.74 | 19.48 | 0.00 | 8.54 | 28.69 |
| 20 | High | La | 5000 | 230.1 | 68.12 | 3.70 | 19.50 | 0.00 | 6.81 | 22.48 |
| 21 | High | La | 5000 | 229.9 | 68.35 | 3.80 | 19.41 | 0.00 | 6.56 | 22.68 |
| 22 | High | La | 1000 | 229.9 | 72.23 | 6.75 | 18.69 | 0.00 | 0.67 | 4.43 |
| 23 | High | La | 1000 | 229.8 | 72.26 | 6.76 | 18.65 | 0.00 | 0.67 | 4.81 |
| 24 | High | La | 1000 | 229.8 | 72.16 | 6.75 | 18.78 | 0.00 | 0.65 | 4.01 |
| 25 | High | La | 5000 | 200.1 | 71.29 | 6.35 | 18.77 | 0.00 | 1.87 | 8.61 |
| 26 | High | La | 1000 | 200.1 | 72.57 | 6.64 | 18.94 | 0.00 | 0.21 | 2.57 |
| 27 | High | La | 1000 | 200.0 | 72.59 | 6.53 | 19.02 | 0.00 | 0.22 | 2.56 |
| 28 | High | La | 1000 | 200.0 | 72.54 | 6.60 | 19.02 | 0.00 | 0.21 | 2.29 |
| 29 | High | La | 5000 | 199.8 | 71.52 | 6.26 | 18.60 | 0.00 | 1.89 | 9.69 |
| 30 | High | La | 1000 | 180.2 | 72.63 | 6.44 | 19.19 | 0.00 | 0.10 | 2.10 |
| 31 | High | La | 5000 | 180.0 | 72.24 | 6.55 | 18.69 | 0.00 | 0.84 | 5.81 |
| 32 | High | La | 5000 | 180.0 | 72.11 | 6.61 | 18.78 | 0.00 | 0.83 | 4.95 |
| 33 | High | La | 1000 | 180.0 | 72.46 | 6.45 | 19.36 | 0.00 | 0.10 | 0.82 |
| 34 | High | La | 1000 | 179.7 | 72.59 | 6.50 | 19.18 | 0.00 | 0.09 | 1.43 |

TABLE 2

Activity of Reference Copper Zinc Catalysts for Methanol Production in Low $CO_2$ Syngas.

| Comp. Ex. No | $CO_2$ | Cat | Temp (° C.) | $H_2$ wt % | CO wt % | $CO_2$ wt % | DME wt % | MeOH wt % | CO & $CO_2$ conv % |
|---|---|---|---|---|---|---|---|---|---|
| 1 | Low | CuZnO Ref A | 316.8 | 62.46 | 24.47 | 4.87 | 0.07 | 6.20 | 20.78 |
| 2 | Low | CuZnO Ref A | 297.7 | 59.30 | 25.34 | 3.67 | 0.03 | 9.71 | 22.43 |
| 3 | Low | CuZnO Ref A | 294.8 | 58.69 | 23.10 | 4.50 | 0.05 | 11.59 | 30.69 |
| 4 | Low | CuZnO Ref A | 274.7 | 53.58 | 21.85 | 4.22 | 0.03 | 18.11 | 39.01 |
| 5 | Low | CuZnO Ref A | 240.3 | 51.15 | 21.60 | 3.73 | 0.00 | 21.26 | 42.22 |
| 6 | Low | CuZnO Ref A | 240.1 | 51.20 | 21.69 | 3.71 | 0.00 | 21.13 | 41.86 |
| 7 | Low | CuZnO Ref A | 240.1 | 56.20 | 23.60 | 3.12 | 0.00 | 15.01 | 33.52 |
| 8 | Low | CuZnO Ref A | 240.0 | 53.25 | 22.90 | 3.60 | 0.00 | 18.06 | 37.10 |
| 9 | Low | CuZnO Ref A | 240.0 | 56.69 | 23.93 | 3.07 | 0.00 | 14.25 | 32.07 |
| 10 | Low | CuZnO Ref A | 240.0 | 58.47 | 25.18 | 3.22 | 0.00 | 11.18 | 24.60 |
| 11 | Low | CuZnO Ref A | 239.7 | 53.32 | 22.64 | 3.60 | 0.00 | 18.26 | 37.57 |
| 12 | Low | CuZnO Ref A | 239.6 | 59.42 | 25.41 | 3.17 | 0.00 | 10.09 | 22.98 |
| 13 | Low | CuZnO Ref A | 238.7 | 51.43 | 21.58 | 3.70 | 0.00 | 21.02 | 42.00 |
| 14 | Low | CuZnO Ref A | 238.4 | 56.35 | 24.71 | 3.27 | 0.00 | 13.64 | 28.86 |
| 15 | Low | CuZnO Ref A | 238.3 | 51.26 | 21.50 | 3.73 | 0.00 | 21.26 | 42.17 |
| 16 | Low | CuZnO Ref A | 238.3 | 56.20 | 24.47 | 3.29 | 0.00 | 14.00 | 29.87 |
| 17 | Low | CuZnO Ref A | 230.2 | 58.46 | 24.73 | 2.94 | 0.00 | 11.89 | 27.78 |
| 18 | Low | CuZnO Ref A | 230.1 | 59.79 | 25.61 | 3.14 | 0.00 | 9.55 | 21.85 |
| 19 | Low | CuZnO Ref A | 230.1 | 57.70 | 24.39 | 3.00 | 0.00 | 12.89 | 29.60 |
| 20 | Low | CuZnO Ref A | 230.1 | 55.59 | 24.02 | 3.38 | 0.00 | 14.93 | 31.62 |
| 21 | Low | CuZnO Ref A | 229.9 | 55.45 | 23.88 | 3.39 | 0.00 | 15.18 | 32.32 |
| 22 | Low | CuZnO Ref A | 229.9 | 60.33 | 25.88 | 3.09 | 0.00 | 8.82 | 20.42 |
| 23 | Low | CuZnO Ref A | 229.8 | 53.64 | 22.97 | 3.48 | 0.00 | 17.75 | 36.55 |
| 24 | Low | CuZnO Ref A | 229.7 | 53.71 | 22.91 | 3.49 | 0.00 | 17.74 | 36.65 |
| 25 | Low | CuZnO Ref A | 228.8 | 53.87 | 22.82 | 3.49 | 0.00 | 17.67 | 36.68 |
| 26 | Low | CuZnO Ref A | 228.5 | 54.11 | 22.87 | 3.47 | 0.00 | 17.40 | 36.32 |
| 27 | Low | CuZnO Ref A | 228.5 | 58.91 | 25.61 | 3.07 | 0.00 | 10.48 | 23.46 |
| 28 | Low | CuZnO Ref A | 228.2 | 59.04 | 25.43 | 3.08 | 0.00 | 10.51 | 23.90 |
| 29 | Low | CuZnO Ref A | 200.4 | 65.53 | 28.37 | 2.71 | 0.00 | 1.71 | 4.55 |

TABLE 2-continued

Activity of Reference Copper Zinc Catalysts for Methanol Production in Low CO$_2$ Syngas.

| Comp. Ex. No | CO$_2$ | Cat | Temp (° C.) | H$_2$ wt % | CO wt % | CO$_2$ wt % | DME wt % | MeOH wt % | CO & CO$_2$ conv % |
|---|---|---|---|---|---|---|---|---|---|
| 30 | Low | CuZnO Ref A | 200.3 | 65.53 | 28.11 | 2.46 | 0.00 | 2.19 | 7.38 |
| 31 | Low | CuZnO Ref A | 200.1 | 64.93 | 28.41 | 2.68 | 0.00 | 2.28 | 5.66 |
| 32 | Low | CuZnO Ref A | 200.1 | 64.71 | 28.01 | 2.68 | 0.00 | 2.87 | 7.90 |
| 33 | Low | CuZnO Ref A | 199.8 | 65.95 | 27.97 | 2.44 | 0.00 | 1.94 | 7.19 |
| 34 | Low | CuZnO Ref A | 199.6 | 65.01 | 28.32 | 2.68 | 0.00 | 2.28 | 6.00 |
| 35 | Low | CuZnO Ref A | 199.6 | 65.73 | 28.52 | 2.69 | 0.00 | 1.38 | 3.39 |
| 36 | Low | CuZnO Ref A | 199.5 | 64.81 | 27.88 | 2.69 | 0.00 | 2.89 | 8.45 |
| 37 | Low | CuZnO Ref A | 198.7 | 65.03 | 27.90 | 2.68 | 0.00 | 2.67 | 7.56 |
| 38 | Low | CuZnO Ref A | 198.6 | 65.53 | 28.71 | 2.57 | 0.00 | 1.50 | 4.07 |
| 39 | Low | CuZnO Ref A | 198.6 | 65.13 | 27.81 | 2.68 | 0.00 | 2.67 | 8.03 |
| 40 | Low | CuZnO Ref A | 198.4 | 65.60 | 28.70 | 2.57 | 0.00 | 1.44 | 4.01 |
| 41 | Low | CuZnO Ref A | 180.3 | 66.41 | 28.66 | 2.66 | 0.00 | 0.62 | 2.14 |
| 42 | Low | CuZnO Ref A | 180.2 | 66.23 | 28.87 | 2.59 | 0.00 | 0.65 | 1.83 |
| 43 | Low | CuZnO Ref A | 180.0 | 66.78 | 28.59 | 2.38 | 0.00 | 0.59 | 3.40 |
| 44 | Low | CuZnO Ref A | 180.0 | 66.46 | 28.72 | 2.66 | 0.00 | 0.51 | 1.71 |
| 45 | Low | CuZnO Ref A | 180.0 | 66.66 | 28.64 | 2.38 | 0.00 | 0.66 | 3.47 |
| 46 | Low | CuZnO Ref A | 179.9 | 66.42 | 28.65 | 2.56 | 0.00 | 0.71 | 2.96 |
| 47 | Low | CuZnO Ref A | 179.9 | 66.17 | 28.95 | 2.59 | 0.00 | 0.63 | 1.53 |
| 48 | Low | CuZnO Ref A | 179.7 | 66.19 | 28.88 | 2.55 | 0.00 | 0.71 | 2.16 |
| 49 | Low | CuZnO Ref A | 179.2 | 66.56 | 28.56 | 2.56 | 0.00 | 0.68 | 2.47 |
| 50 | Low | CuZnO Ref A | 179.2 | 66.51 | 28.61 | 2.56 | 0.00 | 0.66 | 2.31 |
| 51 | Low | CuZnO Ref A | 178.5 | 66.39 | 28.95 | 2.52 | 0.00 | 0.48 | 1.93 |
| 52 | Low | CuZnO Ref A | 178.5 | 66.36 | 29.02 | 2.52 | 0.00 | 0.44 | 1.21 |
| 53 | Low | CuZnO Ref B | 316.8 | 62.70 | 24.36 | 4.79 | 0.15 | 6.08 | 21.27 |
| 54 | Low | CuZnO Ref B | 292.6 | 58.33 | 23.04 | 4.39 | 0.08 | 12.09 | 31.27 |
| 55 | Low | CuZnO Ref B | 275.0 | 53.94 | 21.97 | 4.18 | 0.05 | 17.66 | 38.35 |
| 56 | Low | CuZnO Ref B | 240.1 | 52.10 | 21.74 | 3.69 | 0.01 | 20.22 | 41.32 |
| 57 | Low | CuZnO Ref B | 240.1 | 53.25 | 23.06 | 3.59 | 0.01 | 17.92 | 36.36 |
| 58 | Low | CuZnO Ref B | 240.0 | 52.14 | 21.81 | 3.68 | 0.01 | 20.13 | 40.94 |
| 59 | Low | CuZnO Ref B | 240.0 | 57.31 | 24.66 | 3.23 | 0.00 | 12.80 | 28.08 |
| 60 | Low | CuZnO Ref B | 240.0 | 57.52 | 25.05 | 3.20 | 0.00 | 12.24 | 26.55 |
| 61 | Low | CuZnO Ref B | 239.9 | 53.56 | 22.76 | 3.57 | 0.01 | 17.94 | 36.65 |
| 62 | Low | CuZnO Ref B | 238.4 | 53.68 | 22.49 | 3.31 | 0.01 | 18.34 | 38.64 |
| 63 | Low | CuZnO Ref B | 238.4 | 53.77 | 22.52 | 3.30 | 0.01 | 18.22 | 38.53 |
| 64 | Low | CuZnO Ref B | 238.4 | 56.43 | 24.29 | 3.31 | 0.00 | 13.93 | 30.09 |
| 65 | Low | CuZnO Ref B | 238.4 | 56.59 | 24.24 | 3.30 | 0.00 | 13.83 | 30.29 |
| 66 | Low | CuZnO Ref B | 230.1 | 54.55 | 23.19 | 3.44 | 0.00 | 16.68 | 35.25 |
| 67 | Low | CuZnO Ref B | 229.9 | 55.96 | 24.46 | 3.34 | 0.00 | 14.18 | 29.96 |
| 68 | Low | CuZnO Ref B | 229.9 | 56.15 | 24.46 | 3.32 | 0.00 | 14.03 | 29.55 |
| 69 | Low | CuZnO Ref B | 229.9 | 59.82 | 25.93 | 3.01 | 0.00 | 9.32 | 21.57 |
| 70 | Low | CuZnO Ref B | 229.8 | 59.76 | 25.64 | 3.04 | 0.00 | 9.65 | 22.53 |
| 71 | Low | CuZnO Ref B | 229.5 | 54.39 | 22.99 | 3.46 | 0.00 | 17.02 | 35.86 |
| 72 | Low | CuZnO Ref B | 228.3 | 56.88 | 24.13 | 3.05 | 0.00 | 13.90 | 31.01 |
| 73 | Low | CuZnO Ref B | 228.3 | 59.55 | 25.71 | 3.07 | 0.00 | 9.76 | 22.45 |
| 74 | Low | CuZnO Ref B | 228.3 | 59.64 | 25.72 | 3.06 | 0.00 | 9.67 | 22.22 |
| 75 | Low | CuZnO Ref B | 228.2 | 56.74 | 24.14 | 3.05 | 0.00 | 14.03 | 31.06 |
| 76 | Low | CuZnO Ref B | 200.1 | 65.01 | 28.73 | 2.66 | 0.00 | 1.91 | 4.16 |
| 77 | Low | CuZnO Ref B | 200.0 | 64.96 | 28.80 | 2.65 | 0.00 | 1.90 | 3.99 |
| 78 | Low | CuZnO Ref B | 199.8 | 65.16 | 27.90 | 2.67 | 0.00 | 2.55 | 7.96 |
| 79 | Low | CuZnO Ref B | 199.8 | 65.82 | 28.56 | 2.57 | 0.00 | 1.36 | 4.27 |
| 80 | Low | CuZnO Ref B | 199.8 | 65.87 | 28.61 | 2.56 | 0.00 | 1.28 | 3.43 |
| 81 | Low | CuZnO Ref B | 199.5 | 65.11 | 27.97 | 2.66 | 0.00 | 2.54 | 7.73 |
| 82 | Low | CuZnO Ref B | 198.7 | 65.84 | 28.20 | 2.43 | 0.00 | 1.83 | 6.21 |
| 83 | Low | CuZnO Ref B | 198.6 | 65.90 | 28.07 | 2.45 | 0.00 | 1.88 | 7.04 |
| 118 | Low | CuZnO Ref B | 198.6 | 65.84 | 28.66 | 2.59 | 0.00 | 1.24 | 3.09 |
| 119 | Low | CuZnO Ref B | 198.6 | 65.84 | 28.68 | 2.59 | 0.00 | 1.21 | 3.25 |
| 120 | Low | CuZnO Ref B | 180.3 | 66.64 | 28.75 | 2.54 | 0.00 | 0.42 | 2.19 |
| 121 | Low | CuZnO Ref B | 180.0 | 66.26 | 28.84 | 2.58 | 0.00 | 0.66 | 1.69 |
| 122 | Low | CuZnO Ref B | 180.0 | 65.97 | 29.26 | 2.59 | 0.00 | 0.53 | 0.51 |
| 123 | Low | CuZnO Ref B | 180.0 | 66.46 | 28.89 | 2.53 | 0.00 | 0.47 | 1.93 |
| 124 | Low | CuZnO Ref B | 179.9 | 65.98 | 29.25 | 2.59 | 0.00 | 0.53 | 0.55 |
| 125 | Low | CuZnO Ref B | 179.6 | 66.47 | 28.65 | 2.57 | 0.00 | 0.65 | 2.91 |
| 126 | Low | CuZnO Ref B | 178.9 | 66.75 | 28.66 | 2.40 | 0.00 | 0.53 | 3.26 |
| 127 | Low | CuZnO Ref B | 178.8 | 66.78 | 28.65 | 2.40 | 0.00 | 0.52 | 3.19 |
| 128 | Low | CuZnO Ref B | 178.5 | 66.49 | 28.92 | 2.57 | 0.00 | 0.37 | 0.92 |
| 129 | Low | CuZnO Ref B | 178.3 | 66.56 | 28.84 | 2.57 | 0.00 | 0.39 | 1.12 |

TABLE 3

Activity of Copper Zinc Reference Catalysts for Methanol Production in High $CO_2$ Syngas

| Comp. Ex. No. | $CO_2$ | Cat | Temp (° C.) | $H_2$ wt % | CO wt % | $CO_2$ wt % | DME wt % | MeOH wt % | CO & $CO_2$ conv % |
|---|---|---|---|---|---|---|---|---|---|
| 130 | High | CuZnO Ref A | 238.5 | 66.53 | 2.15 | 19.61 | 0.00 | 9.72 | 31.34 |
| 131 | High | CuZnO Ref A | 238.4 | 66.49 | 2.29 | 19.57 | 0.00 | 9.66 | 30.77 |
| 132 | High | CuZnO Ref A | 238.3 | 66.54 | 2.60 | 19.59 | 0.00 | 9.30 | 29.55 |
| 133 | High | CuZnO Ref A | 238.5 | 66.66 | 2.68 | 19.47 | 0.00 | 9.22 | 29.54 |
| 134 | High | CuZnO Ref A | 238.4 | 66.95 | 2.50 | 19.57 | 0.00 | 9.02 | 29.41 |
| 135 | High | CuZnO Ref A | 239.6 | 66.70 | 2.75 | 19.62 | 0.00 | 8.97 | 28.33 |
| 136 | High | CuZnO Ref A | 238.4 | 66.79 | 2.63 | 19.67 | 0.00 | 8.94 | 28.83 |
| 137 | High | CuZnO Ref A | 240.1 | 66.84 | 2.83 | 19.48 | 0.00 | 8.89 | 28.58 |
| 138 | High | CuZnO Ref A | 228.3 | 67.46 | 2.98 | 19.50 | 0.00 | 8.13 | 26.87 |
| 139 | High | CuZnO Ref A | 228.5 | 67.32 | 3.08 | 19.64 | 0.00 | 8.04 | 25.80 |
| 140 | High | CuZnO Ref A | 228.3 | 67.45 | 3.31 | 19.55 | 0.00 | 7.78 | 25.12 |
| 141 | High | CuZnO Ref A | 228.3 | 67.50 | 3.42 | 19.50 | 0.00 | 7.67 | 24.70 |
| 142 | High | CuZnO Ref A | 229.9 | 67.80 | 3.41 | 19.38 | 0.00 | 7.49 | 25.29 |
| 143 | High | CuZnO Ref A | 229.8 | 67.73 | 3.45 | 19.50 | 0.00 | 7.41 | 24.45 |
| 144 | High | CuZnO Ref A | 229.8 | 67.79 | 3.53 | 19.44 | 0.00 | 7.34 | 24.12 |
| 145 | High | CuZnO Ref A | 228.5 | 67.91 | 3.42 | 19.53 | 0.00 | 7.23 | 24.27 |
| 146 | High | CuZnO Ref A | 228.9 | 67.93 | 3.46 | 19.58 | 0.00 | 7.14 | 23.85 |
| 147 | High | CuZnO Ref A | 198.6 | 71.03 | 6.22 | 18.63 | 0.00 | 2.39 | 10.15 |
| 148 | High | CuZnO Ref A | 198.4 | 70.82 | 6.32 | 18.75 | 0.00 | 2.37 | 9.06 |
| 149 | High | CuZnO Ref A | 198.7 | 70.93 | 6.37 | 18.66 | 0.00 | 2.30 | 9.49 |
| 150 | High | CuZnO Ref A | 198.4 | 70.99 | 6.35 | 18.64 | 0.00 | 2.28 | 9.68 |
| 151 | High | CuZnO Ref A | 199.6 | 71.29 | 6.24 | 18.49 | 0.00 | 2.24 | 10.76 |
| 152 | High | CuZnO Ref A | 200.0 | 71.35 | 6.25 | 18.45 | 0.00 | 2.22 | 10.64 |
| 153 | High | CuZnO Ref A | 200.1 | 71.17 | 6.27 | 18.62 | 0.00 | 2.20 | 10.00 |
| 154 | High | CuZnO Ref A | 198.6 | 71.11 | 6.25 | 18.75 | 0.00 | 2.16 | 9.75 |
| 155 | High | CuZnO Ref A | 198.9 | 71.09 | 6.13 | 18.88 | 0.00 | 2.15 | 9.86 |
| 156 | High | CuZnO Ref A | 179.2 | 72.10 | 6.30 | 18.88 | 0.00 | 1.03 | 6.47 |
| 157 | High | CuZnO Ref A | 179.1 | 72.03 | 6.52 | 18.74 | 0.00 | 1.03 | 6.04 |
| 158 | High | CuZnO Ref A | 178.9 | 71.85 | 6.65 | 18.81 | 0.00 | 1.01 | 4.91 |
| 159 | High | CuZnO Ref A | 179.4 | 71.91 | 6.73 | 18.67 | 0.00 | 1.00 | 5.55 |
| 160 | High | CuZnO Ref A | 180.2 | 72.01 | 6.67 | 18.64 | 0.00 | 0.99 | 5.86 |
| 161 | High | CuZnO Ref A | 180.0 | 71.90 | 6.52 | 18.92 | 0.00 | 0.98 | 5.06 |
| 162 | High | CuZnO Ref A | 180.2 | 72.02 | 6.71 | 18.60 | 0.00 | 0.97 | 5.87 |
| 163 | High | CuZnO Ref A | 178.9 | 71.89 | 6.69 | 18.78 | 0.00 | 0.96 | 5.21 |
| 164 | High | CuZnO Ref A | 178.9 | 71.95 | 6.65 | 18.76 | 0.00 | 0.96 | 5.63 |
| 165 | High | CuZnO Ref B | 240.0 | 67.92 | 3.55 | 19.32 | 0.00 | 7.31 | 24.62 |
| 166 | High | CuZnO Ref B | 239.9 | 67.95 | 3.59 | 19.38 | 0.00 | 7.17 | 24.34 |
| 167 | High | CuZnO Ref B | 239.7 | 67.85 | 3.66 | 19.39 | 0.00 | 7.21 | 23.57 |
| 168 | High | CuZnO Ref B | 238.4 | 68.53 | 4.66 | 19.19 | 0.00 | 5.77 | 19.36 |
| 169 | High | CuZnO Ref B | 238.4 | 68.62 | 4.77 | 19.09 | 0.00 | 5.68 | 19.14 |
| 170 | High | CuZnO Ref B | 238.4 | 70.01 | 3.96 | 18.48 | 0.00 | 5.66 | 25.96 |
| 171 | High | CuZnO Ref B | 238.1 | 69.99 | 3.84 | 18.54 | 0.00 | 5.74 | 26.08 |
| 172 | High | CuZnO Ref B | 230.1 | 68.88 | 4.44 | 19.10 | 0.00 | 5.73 | 20.13 |
| 173 | High | CuZnO Ref B | 230.1 | 68.90 | 4.57 | 19.18 | 0.00 | 5.50 | 19.01 |
| 174 | High | CuZnO Ref B | 229.7 | 68.92 | 4.48 | 19.13 | 0.00 | 5.63 | 19.62 |
| 175 | High | CuZnO Ref B | 228.3 | 69.41 | 5.52 | 18.99 | 0.00 | 4.29 | 14.89 |
| 176 | High | CuZnO Ref B | 228.3 | 70.71 | 4.67 | 18.50 | 0.00 | 4.28 | 21.17 |
| 177 | High | CuZnO Ref B | 228.3 | 69.51 | 5.57 | 18.94 | 0.00 | 4.19 | 14.66 |
| 178 | High | CuZnO Ref B | 228.2 | 70.89 | 5.05 | 18.12 | 0.00 | 4.10 | 21.24 |
| 179 | High | CuZnO Ref B | 200.3 | 71.48 | 6.49 | 18.49 | 0.00 | 1.83 | 8.88 |
| 180 | High | CuZnO Ref B | 200.1 | 71.63 | 6.44 | 18.43 | 0.00 | 1.78 | 9.31 |
| 181 | High | CuZnO Ref B | 199.6 | 71.57 | 6.33 | 18.58 | 0.00 | 1.81 | 9.16 |
| 182 | High | CuZnO Ref B | 198.6 | 71.30 | 6.84 | 18.67 | 0.00 | 1.48 | 6.61 |
| 183 | High | CuZnO Ref B | 198.6 | 71.15 | 6.92 | 18.77 | 0.00 | 1.45 | 5.48 |
| 184 | High | CuZnO Ref B | 198.6 | 72.87 | 5.99 | 17.97 | 0.00 | 1.42 | 13.89 |
| 185 | High | CuZnO Ref B | 198.4 | 72.51 | 6.30 | 18.01 | 0.00 | 1.44 | 12.21 |
| 186 | High | CuZnO Ref B | 180.0 | 72.07 | 6.55 | 18.82 | 0.00 | 0.88 | 5.36 |
| 187 | High | CuZnO Ref B | 179.7 | 72.05 | 6.63 | 18.74 | 0.00 | 0.90 | 5.32 |
| 188 | High | CuZnO Ref B | 179.7 | 72.03 | 6.59 | 18.84 | 0.00 | 0.87 | 4.93 |
| 189 | High | CuZnO Ref B | 178.9 | 71.99 | 6.65 | 18.95 | 0.00 | 0.73 | 4.60 |
| 190 | High | CuZnO Ref B | 178.9 | 71.82 | 6.86 | 18.93 | 0.00 | 0.72 | 3.77 |
| 191 | High | CuZnO Ref B | 178.5 | 73.29 | 6.15 | 18.16 | 0.00 | 0.71 | 10.32 |
| 192 | High | CuZnO Ref B | 178.2 | 73.21 | 6.20 | 18.20 | 0.00 | 0.70 | 10.02 |

TABLE 4

Activity of Promoted Copper Zinc Oxide Catalysts for Methanol Production

| Comp. Ex. No. | $CO_2$ Level | Support | Promoter | Promoter (ppm) | Temp (° C.) | $H_2$ wt % | CO wt % | $CO_2$ wt % | DME wt % | MeOH wt % | CO & $CO_2$ conv % |
|---|---|---|---|---|---|---|---|---|---|---|---|
| 193 | Low | CuZnO Ref A | Ga | 5000 | 316.9 | 62.53 | 24.47 | 4.66 | 0.09 | 6.34 | 21.35 |
| 194 | Low | CuZnO Ref A | K | 5000 | 316.8 | 62.67 | 24.19 | 4.87 | 0.05 | 6.28 | 21.94 |
| 195 | Low | CuZnO Ref A | K | 5000 | 293.3 | 58.13 | 23.04 | 4.45 | 0.04 | 12.28 | 31.35 |
| 196 | Low | CuZnO Ref A | Ga | 5000 | 292.3 | 57.97 | 23.08 | 4.31 | 0.06 | 12.51 | 31.43 |
| 197 | Low | CuZnO Ref A | K | 5000 | 274.7 | 53.69 | 21.56 | 4.24 | 0.02 | 18.27 | 39.84 |
| 198 | Low | CuZnO Ref A | Ga | 5000 | 274.7 | 54.05 | 21.91 | 4.13 | 0.04 | 17.68 | 38.40 |
| 199 | Low | CuZnO Ref A | Rb | 5000 | 240.1 | 54.07 | 23.26 | 3.51 | 0.00 | 17.03 | 35.04 |
| 200 | Low | CuZnO Ref A | La | 5000 | 240.1 | 55.61 | 23.88 | 3.37 | 0.01 | 15.07 | 31.73 |
| 201 | Low | CuZnO Ref A | Ga | 5000 | 240.0 | 53.86 | 22.90 | 3.51 | 0.00 | 17.58 | 36.46 |
| 202 | Low | CuZnO Ref A | Sr | 1000 | 240.0 | 66.57 | 28.66 | 2.65 | 0.00 | 0.47 | 1.56 |
| 203 | Low | CuZnO Ref A | K | 1000 | 240.0 | 67.03 | 28.58 | 2.48 | 0.00 | 0.26 | 2.35 |
| 204 | Low | CuZnO Ref A | Ga | 5000 | 239.9 | 53.86 | 22.67 | 3.53 | 0.00 | 17.78 | 37.23 |
| 205 | Low | CuZnO Ref A | La | 5000 | 239.9 | 55.57 | 23.75 | 3.39 | 0.01 | 15.20 | 32.56 |
| 206 | Low | CuZnO Ref A | Rb | 1000 | 239.9 | 66.38 | 28.82 | 2.70 | 0.00 | 0.44 | 0.85 |
| 207 | Low | CuZnO Ref A | Rb | 1000 | 239.9 | 66.22 | 28.99 | 2.71 | 0.00 | 0.44 | 0.60 |
| 208 | Low | CuZnO Ref A | K | 5000 | 239.7 | 52.32 | 21.91 | 3.67 | 0.00 | 19.88 | 40.53 |
| 209 | Low | CuZnO Ref A | Rb | 5000 | 239.7 | 54.22 | 22.95 | 3.51 | 0.00 | 17.18 | 35.89 |
| 210 | Low | CuZnO Ref A | Sr | 1000 | 239.7 | 66.35 | 28.91 | 2.65 | 0.00 | 0.45 | 0.20 |
| 211 | Low | CuZnO Ref A | K | 1000 | 239.7 | 67.09 | 28.53 | 2.49 | 0.00 | 0.25 | 2.62 |
| 212 | Low | CuZnO Ref A | K | 5000 | 239.6 | 52.32 | 21.94 | 3.66 | 0.00 | 19.86 | 40.46 |
| 213 | Low | CuZnO Ref A | Ba | 1000 | 238.7 | 66.44 | 28.48 | 2.83 | 0.00 | 0.61 | 0.82 |
| 214 | Low | CuZnO Ref A | Sr | 5000 | 238.7 | 66.43 | 28.98 | 2.66 | 0.00 | 0.29 | 0.09 |
| 215 | Low | CuZnO Ref A | K | 5000 | 238.5 | 50.30 | 20.80 | 3.56 | 0.00 | 23.04 | 45.46 |
| 216 | Low | CuZnO Ref A | K | 5000 | 238.5 | 50.53 | 20.95 | 3.53 | 0.00 | 22.69 | 44.95 |
| 217 | Low | CuZnO Ref A | Na | 5000 | 238.5 | 54.22 | 22.71 | 3.51 | 0.00 | 17.42 | 36.63 |
| 218 | Low | CuZnO Ref A | Na | 5000 | 238.5 | 54.28 | 22.81 | 3.49 | 0.00 | 17.28 | 36.34 |
| 219 | Low | CuZnO Ref A | Li | 5000 | 238.5 | 66.59 | 28.31 | 2.71 | 0.00 | 0.72 | 3.25 |
| 220 | Low | CuZnO Ref A | Na | 1000 | 238.5 | 66.12 | 28.91 | 2.83 | 0.00 | 0.51 | −0.99 |
| 221 | Low | CuZnO Ref A | Li | 5000 | 238.4 | 66.60 | 28.31 | 2.72 | 0.00 | 0.72 | 3.31 |
| 222 | Low | CuZnO Ref A | Ba | 1000 | 238.4 | 66.48 | 28.40 | 2.84 | 0.00 | 0.64 | 1.14 |
| 223 | Low | CuZnO Ref A | Na | 1000 | 238.4 | 66.06 | 28.95 | 2.83 | 0.00 | 0.54 | −1.13 |
| 224 | Low | CuZnO Ref A | Li | 1000 | 238.4 | 67.20 | 28.17 | 2.50 | 0.00 | 0.47 | 3.95 |
| 225 | Low | CuZnO Ref A | La | 1000 | 238.4 | 66.72 | 28.69 | 2.65 | 0.00 | 0.30 | 1.10 |
| 226 | Low | CuZnO Ref A | La | 1000 | 238.4 | 66.70 | 28.72 | 2.65 | 0.00 | 0.29 | 1.25 |
| 227 | Low | CuZnO Ref A | Sr | 5000 | 238.4 | 66.43 | 29.00 | 2.66 | 0.00 | 0.27 | 0.17 |
| 228 | Low | CuZnO Ref A | Li | 1000 | 238.3 | 67.23 | 28.11 | 2.51 | 0.00 | 0.50 | 4.16 |
| 229 | Low | CuZnO Ref A | Ga | 5000 | 230.1 | 57.25 | 24.21 | 3.26 | 0.00 | 13.24 | 30.01 |
| 230 | Low | CuZnO Ref A | K | 1000 | 230.1 | 67.09 | 28.57 | 2.49 | 0.00 | 0.20 | 2.46 |
| 231 | Low | CuZnO Ref A | Rb | 5000 | 229.9 | 56.73 | 24.49 | 3.30 | 0.00 | 13.45 | 28.99 |
| 232 | Low | CuZnO Ref A | Ga | 5000 | 229.9 | 57.23 | 24.22 | 3.26 | 0.00 | 13.27 | 29.87 |
| 233 | Low | CuZnO Ref A | La | 5000 | 229.9 | 58.79 | 25.13 | 3.12 | 0.00 | 11.01 | 25.26 |
| 234 | Low | CuZnO Ref A | Sr | 1000 | 229.9 | 66.70 | 28.65 | 2.65 | 0.00 | 0.36 | 1.58 |
| 235 | Low | CuZnO Ref A | Rb | 1000 | 229.9 | 66.44 | 28.87 | 2.70 | 0.00 | 0.34 | 0.81 |
| 236 | Low | CuZnO Ref A | K | 5000 | 229.8 | 55.29 | 23.51 | 3.38 | 0.00 | 15.71 | 33.64 |
| 237 | Low | CuZnO Ref A | Rb | 5000 | 229.8 | 56.43 | 24.41 | 3.34 | 0.00 | 13.78 | 29.72 |
| 238 | Low | CuZnO Ref A | La | 5000 | 229.8 | 58.83 | 25.13 | 3.12 | 0.00 | 10.97 | 25.29 |
| 239 | Low | CuZnO Ref A | Rb | 1000 | 229.8 | 66.39 | 28.94 | 2.70 | 0.00 | 0.33 | 0.36 |
| 240 | Low | CuZnO Ref A | K | 1000 | 229.8 | 67.16 | 28.52 | 2.49 | 0.00 | 0.18 | 2.62 |
| 241 | Low | CuZnO Ref A | K | 5000 | 229.7 | 55.35 | 23.57 | 3.39 | 0.00 | 15.59 | 33.30 |
| 242 | Low | CuZnO Ref A | Sr | 1000 | 229.7 | 66.82 | 28.55 | 2.65 | 0.00 | 0.32 | 2.23 |
| 243 | Low | CuZnO Ref A | Sr | 5000 | 228.8 | 66.62 | 28.87 | 2.65 | 0.00 | 0.20 | 0.77 |
| 244 | Low | CuZnO Ref A | Ba | 1000 | 228.6 | 66.50 | 28.56 | 2.83 | 0.00 | 0.48 | 0.07 |
| 245 | Low | CuZnO Ref A | Na | 1000 | 228.6 | 66.40 | 28.73 | 2.82 | 0.00 | 0.43 | −0.56 |
| 246 | Low | CuZnO Ref A | Li | 1000 | 228.6 | 67.24 | 28.28 | 2.49 | 0.00 | 0.34 | 2.97 |
| 247 | Low | CuZnO Ref A | Sr | 5000 | 228.6 | 66.66 | 28.82 | 2.65 | 0.00 | 0.22 | 0.48 |
| 248 | Low | CuZnO Ref A | K | 5000 | 228.5 | 53.41 | 22.26 | 3.30 | 0.00 | 18.84 | 39.32 |
| 249 | Low | CuZnO Ref A | Na | 5000 | 228.5 | 57.23 | 24.18 | 3.28 | 0.00 | 13.30 | 29.47 |
| 250 | Low | CuZnO Ref A | Na | 1000 | 228.5 | 66.41 | 28.74 | 2.83 | 0.00 | 0.39 | −0.47 |
| 251 | Low | CuZnO Ref A | La | 1000 | 228.5 | 66.76 | 28.71 | 2.66 | 0.00 | 0.24 | 1.05 |
| 252 | Low | CuZnO Ref A | K | 5000 | 228.3 | 53.11 | 22.21 | 3.32 | 0.00 | 19.16 | 39.80 |
| 253 | Low | CuZnO Ref A | Na | 5000 | 228.3 | 57.49 | 24.19 | 3.25 | 0.00 | 13.05 | 29.45 |
| 254 | Low | CuZnO Ref A | Li | 5000 | 228.3 | 66.73 | 28.45 | 2.72 | 0.00 | 0.46 | 1.99 |
| 255 | Low | CuZnO Ref A | Li | 5000 | 228.3 | 66.82 | 28.38 | 2.71 | 0.00 | 0.44 | 2.30 |
| 256 | Low | CuZnO Ref A | Li | 1000 | 228.3 | 67.16 | 28.31 | 2.49 | 0.00 | 0.38 | 3.15 |
| 257 | Low | CuZnO Ref A | La | 1000 | 228.3 | 66.72 | 28.78 | 2.65 | 0.00 | 0.21 | 0.65 |
| 258 | Low | CuZnO Ref A | Ba | 1000 | 228.2 | 66.55 | 28.47 | 2.83 | 0.00 | 0.51 | 0.66 |
| 259 | Low | CuZnO Ref A | Rb | 5000 | 200.3 | 65.08 | 28.44 | 2.71 | 0.00 | 2.07 | 5.12 |
| 260 | Low | CuZnO Ref A | K | 5000 | 200.1 | 65.71 | 28.17 | 2.65 | 0.00 | 1.78 | 5.89 |
| 261 | Low | CuZnO Ref A | K | 5000 | 200.1 | 65.66 | 28.23 | 2.65 | 0.00 | 1.76 | 5.64 |
| 262 | Low | CuZnO Ref A | La | 5000 | 200.1 | 66.20 | 28.64 | 2.55 | 0.00 | 0.94 | 3.09 |
| 263 | Low | CuZnO Ref A | K | 1000 | 200.1 | 67.00 | 28.79 | 2.50 | 0.00 | 0.07 | 1.56 |
| 264 | Low | CuZnO Ref A | K | 1000 | 200.1 | 67.16 | 28.64 | 2.49 | 0.00 | 0.06 | 1.75 |
| 265 | Low | CuZnO Ref A | Sr | 1000 | 200.0 | 66.97 | 28.64 | 2.65 | 0.00 | 0.11 | 0.96 |
| 266 | Low | CuZnO Ref A | Rb | 1000 | 200.0 | 66.62 | 28.93 | 2.70 | 0.00 | 0.11 | 0.17 |

TABLE 4-continued

Activity of Promoted Copper Zinc Oxide Catalysts for Methanol Production

| Comp. Ex. No. | $CO_2$ Level | Support | Promoter | Promoter (ppm) | Temp (° C.) | $H_2$ wt % | CO wt % | $CO_2$ wt % | DME wt % | MeOH wt % | CO & $CO_2$ conv % |
|---|---|---|---|---|---|---|---|---|---|---|---|
| 267 | Low | CuZnO Ref A | Sr | 1000 | 200.0 | 66.97 | 28.64 | 2.65 | 0.00 | 0.10 | 1.21 |
| 268 | Low | CuZnO Ref A | Rb | 5000 | 199.8 | 65.10 | 28.42 | 2.72 | 0.00 | 2.07 | 5.34 |
| 269 | Low | CuZnO Ref A | La | 5000 | 199.8 | 66.14 | 28.64 | 2.55 | 0.00 | 1.00 | 3.29 |
| 270 | Low | CuZnO Ref A | Ga | 5000 | 199.6 | 65.87 | 28.36 | 2.60 | 0.00 | 1.48 | 4.90 |
| 271 | Low | CuZnO Ref A | Rb | 1000 | 199.6 | 66.58 | 28.98 | 2.70 | 0.00 | 0.10 | −0.15 |
| 272 | Low | CuZnO Ref A | Ga | 5000 | 199.5 | 65.91 | 28.30 | 2.60 | 0.00 | 1.50 | 5.30 |
| 273 | Low | CuZnO Ref A | K | 5000 | 198.7 | 65.43 | 27.86 | 2.50 | 0.00 | 2.49 | 8.34 |
| 274 | Low | CuZnO Ref A | Li | 5000 | 198.7 | 66.95 | 28.57 | 2.72 | 0.00 | 0.12 | 0.82 |
| 275 | Low | CuZnO Ref A | Li | 1000 | 198.7 | 67.33 | 28.42 | 2.50 | 0.00 | 0.12 | 2.13 |
| 276 | Low | CuZnO Ref A | Sr | 5000 | 198.7 | 66.81 | 28.82 | 2.66 | 0.00 | 0.08 | 0.82 |
| 277 | Low | CuZnO Ref A | Na | 5000 | 198.6 | 66.16 | 28.19 | 2.63 | 0.00 | 1.34 | 4.56 |
| 278 | Low | CuZnO Ref A | Na | 5000 | 198.6 | 66.22 | 28.13 | 2.63 | 0.00 | 1.34 | 4.79 |
| 279 | Low | CuZnO Ref A | Ba | 1000 | 198.6 | 66.76 | 28.65 | 2.84 | 0.00 | 0.14 | −0.74 |
| 280 | Low | CuZnO Ref A | Na | 1000 | 198.6 | 66.62 | 28.81 | 2.82 | 0.00 | 0.13 | −1.31 |
| 281 | Low | CuZnO Ref A | Na | 1000 | 198.6 | 66.63 | 28.80 | 2.83 | 0.00 | 0.12 | −0.85 |
| 282 | Low | CuZnO Ref A | Li | 1000 | 198.6 | 67.42 | 28.35 | 2.49 | 0.00 | 0.11 | 2.44 |
| 283 | Low | CuZnO Ref A | Li | 5000 | 198.6 | 67.01 | 28.52 | 2.73 | 0.00 | 0.11 | 1.06 |
| 284 | Low | CuZnO Ref A | Sr | 5000 | 198.6 | 66.87 | 28.75 | 2.66 | 0.00 | 0.07 | 1.10 |
| 285 | Low | CuZnO Ref A | K | 5000 | 198.4 | 65.54 | 27.71 | 2.50 | 0.00 | 2.53 | 8.59 |
| 286 | Low | CuZnO Ref A | Ba | 1000 | 198.4 | 66.79 | 28.60 | 2.84 | 0.00 | 0.15 | −0.41 |
| 287 | Low | CuZnO Ref A | La | 1000 | 198.4 | 66.79 | 28.84 | 2.66 | 0.00 | 0.08 | 0.05 |
| 288 | Low | CuZnO Ref A | La | 1000 | 198.4 | 66.83 | 28.80 | 2.66 | 0.00 | 0.07 | 0.27 |
| 289 | Low | CuZnO Ref A | K | 5000 | 180.2 | 66.55 | 28.79 | 2.60 | 0.00 | 0.41 | 1.57 |
| 290 | Low | CuZnO Ref A | K | 5000 | 180.2 | 66.65 | 28.70 | 2.59 | 0.00 | 0.40 | 2.01 |
| 291 | Low | CuZnO Ref A | Ga | 5000 | 180.0 | 66.30 | 29.04 | 2.57 | 0.00 | 0.44 | 0.21 |
| 292 | Low | CuZnO Ref A | Rb | 5000 | 180.0 | 66.29 | 29.00 | 2.63 | 0.00 | 0.43 | 0.70 |
| 293 | Low | CuZnO Ref A | Rb | 5000 | 180.0 | 66.26 | 29.03 | 2.63 | 0.00 | 0.43 | 0.67 |
| 294 | Low | CuZnO Ref A | La | 5000 | 180.0 | 66.61 | 28.83 | 2.53 | 0.00 | 0.38 | 1.52 |
| 295 | Low | CuZnO Ref A | Rb | 1000 | 180.0 | 66.63 | 28.97 | 2.71 | 0.00 | 0.05 | −0.19 |
| 296 | Low | CuZnO Ref A | Sr | 1000 | 180.0 | 67.06 | 28.61 | 2.66 | 0.00 | 0.05 | 0.84 |
| 297 | Low | CuZnO Ref A | La | 5000 | 179.9 | 66.80 | 28.69 | 2.55 | 0.00 | 0.32 | 1.79 |
| 298 | Low | CuZnO Ref A | Sr | 1000 | 179.9 | 67.08 | 28.58 | 2.65 | 0.00 | 0.06 | 0.99 |
| 299 | Low | CuZnO Ref A | Rb | 1000 | 179.9 | 66.60 | 29.01 | 2.70 | 0.00 | 0.05 | −0.49 |
| 300 | Low | CuZnO Ref A | K | 1000 | 179.9 | 67.02 | 28.79 | 2.50 | 0.00 | 0.03 | 1.67 |
| 301 | Low | CuZnO Ref A | K | 1000 | 179.9 | 67.07 | 28.75 | 2.51 | 0.00 | 0.03 | 1.78 |
| 302 | Low | CuZnO Ref A | Ga | 5000 | 179.6 | 66.60 | 28.75 | 2.57 | 0.00 | 0.43 | 1.99 |
| 303 | Low | CuZnO Ref A | Li | 5000 | 179.6 | 66.97 | 28.63 | 2.73 | 0.00 | 0.05 | 0.16 |
| 304 | Low | CuZnO Ref A | Na | 1000 | 179.4 | 66.71 | 28.79 | 2.83 | 0.00 | 0.06 | −0.83 |
| 305 | Low | CuZnO Ref A | Na | 1000 | 179.1 | 66.75 | 28.73 | 2.82 | 0.00 | 0.06 | −0.50 |
| 306 | Low | CuZnO Ref A | K | 5000 | 178.9 | 66.90 | 28.55 | 2.42 | 0.00 | 0.48 | 2.99 |
| 307 | Low | CuZnO Ref A | Na | 5000 | 178.9 | 66.88 | 28.58 | 2.60 | 0.00 | 0.30 | 1.41 |
| 308 | Low | CuZnO Ref A | Ba | 1000 | 178.9 | 66.83 | 28.64 | 2.85 | 0.00 | 0.06 | −0.72 |
| 309 | Low | CuZnO Ref A | Li | 5000 | 178.9 | 67.04 | 28.54 | 2.73 | 0.00 | 0.05 | 0.74 |
| 310 | Low | CuZnO Ref A | Sr | 5000 | 178.9 | 66.93 | 28.74 | 2.66 | 0.00 | 0.04 | 0.79 |
| 311 | Low | CuZnO Ref A | Sr | 5000 | 178.9 | 66.90 | 28.77 | 2.66 | 0.00 | 0.03 | 0.47 |
| 312 | Low | CuZnO Ref A | K | 5000 | 178.8 | 66.97 | 28.49 | 2.42 | 0.00 | 0.47 | 3.28 |
| 313 | Low | CuZnO Ref A | Ba | 1000 | 178.8 | 66.82 | 28.66 | 2.85 | 0.00 | 0.06 | −0.83 |
| 314 | Low | CuZnO Ref A | Na | 5000 | 178.6 | 66.90 | 28.54 | 2.60 | 0.00 | 0.31 | 1.66 |
| 315 | Low | CuZnO Ref A | Li | 1000 | 178.6 | 67.42 | 28.38 | 2.51 | 0.00 | 0.05 | 2.68 |
| 316 | Low | CuZnO Ref A | Li | 1000 | 178.6 | 67.25 | 28.57 | 2.50 | 0.00 | 0.05 | 1.85 |
| 317 | Low | CuZnO Ref A | La | 1000 | 178.5 | 66.89 | 28.78 | 2.66 | 0.00 | 0.04 | 0.17 |
| 318 | Low | CuZnO Ref A | La | 1000 | 178.5 | 66.85 | 28.83 | 2.66 | 0.00 | 0.03 | 0.07 |
| 319 | Low | CuZnO Ref B | Ga | 5000 | 316.9 | 62.50 | 24.65 | 4.51 | 0.33 | 6.11 | 20.88 |
| 320 | Low | CuZnO Ref B | Ga | 5000 | 295.9 | 58.95 | 23.70 | 4.22 | 0.20 | 10.91 | 28.46 |
| 321 | Low | CuZnO Ref B | Ga | 5000 | 275.0 | 54.98 | 22.52 | 3.97 | 0.09 | 16.29 | 36.10 |
| 322 | Low | CuZnO Ref B | Ga | 5000 | 240.0 | 56.41 | 23.86 | 3.34 | 0.01 | 14.32 | 31.79 |
| 323 | Low | CuZnO Ref B | Ga | 5000 | 239.9 | 56.36 | 23.79 | 3.34 | 0.01 | 14.43 | 31.88 |
| 324 | Low | CuZnO Ref B | K | 5000 | 239.9 | 58.79 | 25.38 | 3.17 | 0.00 | 10.71 | 24.35 |
| 325 | Low | CuZnO Ref B | K | 5000 | 239.7 | 58.78 | 25.42 | 3.16 | 0.00 | 10.69 | 24.25 |
| 326 | Low | CuZnO Ref B | Ga | 5000 | 230.1 | 59.75 | 25.62 | 3.06 | 0.00 | 9.65 | 22.79 |
| 327 | Low | CuZnO Ref B | K | 5000 | 229.9 | 61.38 | 26.71 | 2.96 | 0.00 | 7.09 | 16.97 |
| 328 | Low | CuZnO Ref B | K | 5000 | 229.9 | 61.44 | 26.65 | 2.97 | 0.00 | 7.09 | 16.92 |
| 329 | Low | CuZnO Ref B | Ga | 5000 | 229.5 | 59.85 | 25.59 | 3.06 | 0.00 | 9.57 | 22.86 |
| 330 | Low | CuZnO Ref B | K | 5000 | 200.3 | 66.22 | 28.74 | 2.63 | 0.00 | 0.74 | 2.32 |
| 331 | Low | CuZnO Ref B | Ga | 5000 | 199.8 | 66.23 | 28.51 | 2.58 | 0.00 | 1.01 | 3.88 |
| 332 | Low | CuZnO Ref B | Ga | 5000 | 199.8 | 66.16 | 28.59 | 2.58 | 0.00 | 1.00 | 3.45 |
| 333 | Low | CuZnO Ref B | K | 5000 | 199.8 | 66.16 | 28.80 | 2.62 | 0.00 | 0.75 | 2.20 |
| 334 | Low | CuZnO Ref B | K | 5000 | 180.2 | 66.55 | 28.94 | 2.63 | 0.00 | 0.23 | 0.56 |
| 335 | Low | CuZnO Ref B | K | 5000 | 180.0 | 66.59 | 28.90 | 2.63 | 0.00 | 0.23 | 0.76 |
| 336 | Low | CuZnO Ref B | Ga | 5000 | 179.9 | 66.67 | 28.77 | 2.58 | 0.00 | 0.32 | 1.83 |
| 337 | Low | CuZnO Ref B | Ga | 5000 | 179.7 | 66.67 | 28.79 | 2.58 | 0.00 | 0.32 | 1.52 |
| 338 | High | CuZnO Ref A | La | 1000 | 240.1 | 72.29 | 6.78 | 18.78 | 0.00 | 0.49 | 3.80 |
| 339 | High | CuZnO Ref A | K | 5000 | 240.0 | 67.72 | 3.73 | 19.59 | 0.00 | 7.08 | 22.48 |
| 340 | High | CuZnO Ref A | Rb | 5000 | 240.0 | 68.43 | 4.10 | 19.42 | 0.00 | 6.19 | 20.83 |

TABLE 4-continued

Activity of Promoted Copper Zinc Oxide Catalysts for Methanol Production

| Comp. Ex. No. | CO$_2$ Level | Support | Promoter | Promoter (ppm) | Temp (° C.) | H$_2$ wt % | CO wt % | CO$_2$ wt % | DME wt % | MeOH wt % | CO & CO$_2$ conv % |
|---|---|---|---|---|---|---|---|---|---|---|---|
| 341 | High | CuZnO Ref A | Li | 1000 | 240.0 | 72.39 | 6.70 | 18.79 | 0.00 | 0.45 | 3.93 |
| 342 | High | CuZnO Ref A | La | 5000 | 239.9 | 67.81 | 3.55 | 19.30 | 0.00 | 7.44 | 24.83 |
| 343 | High | CuZnO Ref A | K | 5000 | 239.9 | 67.79 | 3.74 | 19.58 | 0.00 | 7.02 | 22.30 |
| 344 | High | CuZnO Ref A | Li | 1000 | 239.9 | 72.44 | 6.66 | 18.76 | 0.00 | 0.48 | 4.22 |
| 345 | High | CuZnO Ref A | Rb | 1000 | 239.9 | 72.41 | 6.70 | 18.79 | 0.00 | 0.43 | 4.66 |
| 346 | High | CuZnO Ref A | Rb | 1000 | 239.9 | 72.23 | 6.77 | 18.92 | 0.00 | 0.41 | 3.26 |
| 347 | High | CuZnO Ref A | La | 5000 | 239.7 | 67.83 | 3.43 | 19.35 | 0.00 | 7.48 | 25.12 |
| 348 | High | CuZnO Ref A | La | 5000 | 239.7 | 67.86 | 3.59 | 19.26 | 0.00 | 7.39 | 24.96 |
| 349 | High | CuZnO Ref A | K | 5000 | 239.7 | 67.66 | 3.69 | 19.57 | 0.00 | 7.19 | 22.92 |
| 350 | High | CuZnO Ref A | La | 1000 | 239.7 | 72.24 | 6.82 | 18.81 | 0.00 | 0.47 | 3.43 |
| 351 | High | CuZnO Ref A | Li | 1000 | 239.7 | 72.28 | 6.88 | 18.72 | 0.00 | 0.47 | 3.24 |
| 352 | High | CuZnO Ref A | K | 1000 | 239.7 | 72.31 | 6.72 | 18.95 | 0.00 | 0.35 | 3.58 |
| 353 | High | CuZnO Ref A | K | 1000 | 239.7 | 72.35 | 6.70 | 18.94 | 0.00 | 0.34 | 3.71 |
| 354 | High | CuZnO Ref A | Rb | 5000 | 239.6 | 68.56 | 4.08 | 19.44 | 0.00 | 6.08 | 20.60 |
| 355 | High | CuZnO Ref A | Na | 1000 | 238.7 | 72.10 | 7.05 | 18.67 | 0.00 | 0.51 | 3.41 |
| 356 | High | CuZnO Ref A | Sr | 1000 | 238.7 | 72.19 | 6.51 | 19.14 | 0.00 | 0.48 | 4.04 |
| 357 | High | CuZnO Ref A | Sr | 5000 | 238.7 | 71.84 | 7.34 | 18.81 | 0.00 | 0.35 | 1.23 |
| 358 | High | CuZnO Ref A | Ga | 5000 | 238.5 | 67.28 | 3.30 | 19.73 | 0.00 | 7.78 | 24.59 |
| 359 | High | CuZnO Ref A | Na | 5000 | 238.5 | 68.09 | 4.28 | 19.39 | 0.00 | 6.37 | 20.52 |
| 360 | High | CuZnO Ref A | Na | 5000 | 238.5 | 68.34 | 4.37 | 19.14 | 0.00 | 6.28 | 21.49 |
| 361 | High | CuZnO Ref A | Sr | 1000 | 238.5 | 72.21 | 6.62 | 19.04 | 0.00 | 0.46 | 3.95 |
| 362 | High | CuZnO Ref A | Ga | 5000 | 238.4 | 67.25 | 3.35 | 19.71 | 0.00 | 7.79 | 24.23 |
| 363 | High | CuZnO Ref A | Na | 1000 | 238.4 | 72.15 | 6.97 | 18.72 | 0.00 | 0.49 | 3.49 |
| 364 | High | CuZnO Ref A | Ba | 1000 | 238.4 | 71.94 | 7.21 | 18.93 | 0.00 | 0.26 | 1.06 |
| 365 | High | CuZnO Ref A | Ba | 1000 | 238.4 | 71.96 | 7.11 | 19.03 | 0.00 | 0.25 | 1.19 |
| 366 | High | CuZnO Ref A | Li | 5000 | 238.3 | 72.03 | 6.98 | 18.78 | 0.00 | 0.53 | 3.93 |
| 367 | High | CuZnO Ref A | Li | 5000 | 238.3 | 71.81 | 7.04 | 18.96 | 0.00 | 0.52 | 2.58 |
| 368 | High | CuZnO Ref A | Sr | 5000 | 238.3 | 71.92 | 7.34 | 18.75 | 0.00 | 0.33 | 1.77 |
| 369 | High | CuZnO Ref A | La | 5000 | 230.1 | 68.78 | 4.64 | 19.42 | 0.00 | 5.35 | 17.06 |
| 370 | High | CuZnO Ref A | Rb | 5000 | 230.1 | 69.48 | 4.64 | 19.17 | 0.00 | 4.89 | 18.12 |
| 371 | High | CuZnO Ref A | Rb | 5000 | 230.1 | 69.39 | 4.74 | 19.29 | 0.00 | 4.76 | 16.78 |
| 372 | High | CuZnO Ref A | Rb | 5000 | 230.1 | 69.41 | 4.77 | 19.36 | 0.00 | 4.65 | 16.32 |
| 373 | High | CuZnO Ref A | Li | 1000 | 230.1 | 72.44 | 6.67 | 18.87 | 0.00 | 0.37 | 3.42 |
| 374 | High | CuZnO Ref A | La | 1000 | 230.1 | 72.39 | 6.69 | 18.90 | 0.00 | 0.36 | 3.29 |
| 375 | High | CuZnO Ref A | Rb | 1000 | 229.9 | 72.46 | 6.60 | 18.95 | 0.00 | 0.32 | 3.95 |
| 376 | High | CuZnO Ref A | K | 1000 | 229.9 | 72.30 | 6.75 | 19.00 | 0.00 | 0.29 | 2.86 |
| 377 | High | CuZnO Ref A | K | 1000 | 229.9 | 72.32 | 6.68 | 19.08 | 0.00 | 0.26 | 2.55 |
| 378 | High | CuZnO Ref A | La | 5000 | 229.8 | 69.17 | 4.76 | 18.94 | 0.00 | 5.29 | 19.07 |
| 379 | High | CuZnO Ref A | La | 5000 | 229.8 | 69.36 | 4.82 | 18.97 | 0.00 | 5.02 | 18.37 |
| 380 | High | CuZnO Ref A | La | 1000 | 229.8 | 72.31 | 6.76 | 18.87 | 0.00 | 0.40 | 3.04 |
| 381 | High | CuZnO Ref A | Li | 1000 | 229.8 | 72.42 | 6.74 | 18.79 | 0.00 | 0.39 | 3.27 |
| 382 | High | CuZnO Ref A | La | 1000 | 229.8 | 72.26 | 6.80 | 18.91 | 0.00 | 0.37 | 2.80 |
| 383 | High | CuZnO Ref A | Li | 1000 | 229.8 | 72.45 | 6.71 | 18.83 | 0.00 | 0.36 | 3.49 |
| 384 | High | CuZnO Ref A | Rb | 1000 | 229.7 | 72.31 | 6.74 | 18.94 | 0.00 | 0.36 | 3.16 |
| 385 | High | CuZnO Ref A | Na | 1000 | 228.6 | 72.29 | 6.83 | 18.80 | 0.00 | 0.41 | 3.51 |
| 386 | High | CuZnO Ref A | Ga | 5000 | 228.5 | 68.64 | 4.31 | 19.45 | 0.00 | 5.75 | 19.48 |
| 387 | High | CuZnO Ref A | K | 5000 | 228.5 | 68.97 | 4.87 | 19.29 | 0.00 | 5.06 | 16.76 |
| 388 | High | CuZnO Ref A | Sr | 1000 | 228.5 | 72.11 | 6.59 | 19.24 | 0.00 | 0.39 | 2.75 |
| 389 | High | CuZnO Ref A | Na | 1000 | 228.5 | 72.05 | 6.96 | 18.95 | 0.00 | 0.38 | 1.97 |
| 390 | High | CuZnO Ref A | Sr | 1000 | 228.5 | 72.09 | 6.53 | 19.36 | 0.00 | 0.36 | 2.27 |
| 391 | High | CuZnO Ref A | Sr | 5000 | 228.5 | 71.86 | 7.29 | 18.92 | 0.00 | 0.28 | 0.73 |
| 392 | High | CuZnO Ref A | Sr | 5000 | 228.5 | 71.86 | 7.26 | 18.97 | 0.00 | 0.26 | 0.33 |
| 393 | High | CuZnO Ref A | Ba | 1000 | 228.5 | 71.94 | 7.11 | 19.10 | 0.00 | 0.21 | 0.43 |
| 394 | High | CuZnO Ref A | Ga | 5000 | 228.3 | 68.64 | 4.38 | 19.36 | 0.00 | 5.77 | 19.61 |
| 395 | High | CuZnO Ref A | K | 5000 | 228.3 | 69.05 | 4.75 | 19.28 | 0.00 | 5.11 | 17.32 |
| 396 | High | CuZnO Ref A | Na | 5000 | 228.3 | 69.20 | 5.10 | 19.06 | 0.00 | 4.82 | 17.00 |
| 397 | High | CuZnO Ref A | Na | 5000 | 228.3 | 69.27 | 5.08 | 19.12 | 0.00 | 4.71 | 16.58 |
| 398 | High | CuZnO Ref A | Li | 5000 | 228.3 | 71.83 | 6.95 | 19.18 | 0.00 | 0.37 | 1.41 |
| 399 | High | CuZnO Ref A | Ba | 1000 | 228.3 | 71.82 | 7.11 | 19.24 | 0.00 | 0.19 | −0.25 |
| 400 | High | CuZnO Ref A | K | 5000 | 228.2 | 68.99 | 4.82 | 19.40 | 0.00 | 4.98 | 16.44 |
| 401 | High | CuZnO Ref A | Li | 5000 | 228.2 | 71.89 | 6.99 | 19.07 | 0.00 | 0.39 | 2.02 |
| 402 | High | CuZnO Ref A | La | 1000 | 200.3 | 72.65 | 6.56 | 19.00 | 0.00 | 0.15 | 2.73 |
| 403 | High | CuZnO Ref A | K | 5000 | 200.1 | 71.41 | 6.53 | 18.81 | 0.00 | 1.55 | 7.00 |
| 404 | High | CuZnO Ref A | K | 1000 | 200.1 | 72.26 | 6.67 | 19.32 | 0.00 | 0.11 | 1.15 |
| 405 | High | CuZnO Ref A | K | 5000 | 200.0 | 71.44 | 6.58 | 18.72 | 0.00 | 1.55 | 7.07 |
| 406 | High | CuZnO Ref A | Rb | 5000 | 200.0 | 71.70 | 6.45 | 18.70 | 0.00 | 1.44 | 7.35 |
| 407 | High | CuZnO Ref A | Rb | 5000 | 200.0 | 71.69 | 6.47 | 18.73 | 0.00 | 1.41 | 7.13 |
| 408 | High | CuZnO Ref A | La | 5000 | 200.0 | 71.83 | 6.64 | 18.49 | 0.00 | 1.33 | 7.09 |
| 409 | High | CuZnO Ref A | Li | 1000 | 200.0 | 72.61 | 6.52 | 19.06 | 0.00 | 0.16 | 2.21 |
| 410 | High | CuZnO Ref A | La | 1000 | 200.0 | 72.62 | 6.57 | 19.01 | 0.00 | 0.15 | 2.78 |
| 411 | High | CuZnO Ref A | La | 5000 | 199.8 | 71.53 | 6.47 | 18.90 | 0.00 | 1.41 | 6.03 |
| 412 | High | CuZnO Ref A | La | 5000 | 199.8 | 71.87 | 6.54 | 18.52 | 0.00 | 1.36 | 7.73 |
| 413 | High | CuZnO Ref A | Li | 1000 | 199.8 | 72.69 | 6.47 | 19.05 | 0.00 | 0.15 | 2.69 |
| 414 | High | CuZnO Ref A | Li | 1000 | 199.8 | 72.65 | 6.52 | 19.05 | 0.00 | 0.14 | 2.39 |

TABLE 4-continued

Activity of Promoted Copper Zinc Oxide Catalysts for Methanol Production

| Comp. Ex. No. | CO$_2$ Level | Support | Promoter | Promoter (ppm) | Temp (° C.) | H$_2$ wt % | CO wt % | CO$_2$ wt % | DME wt % | MeOH wt % | CO & CO$_2$ conv % |
|---|---|---|---|---|---|---|---|---|---|---|---|
| 415 | High | CuZnO Ref A | Rb | 1000 | 199.8 | 72.47 | 6.58 | 19.16 | 0.00 | 0.14 | 2.25 |
| 416 | High | CuZnO Ref A | La | 1000 | 199.8 | 72.47 | 6.62 | 19.13 | 0.00 | 0.14 | 1.66 |
| 417 | High | CuZnO Ref A | K | 5000 | 199.6 | 71.47 | 6.57 | 18.72 | 0.00 | 1.54 | 7.25 |
| 418 | High | CuZnO Ref A | Rb | 5000 | 199.6 | 71.71 | 6.49 | 18.68 | 0.00 | 1.42 | 7.21 |
| 419 | High | CuZnO Ref A | Rb | 1000 | 199.6 | 72.40 | 6.57 | 19.24 | 0.00 | 0.13 | 1.77 |
| 420 | High | CuZnO Ref A | K | 1000 | 199.6 | 72.50 | 6.63 | 19.11 | 0.00 | 0.11 | 2.25 |
| 421 | High | CuZnO Ref A | Na | 5000 | 199.0 | 71.24 | 6.83 | 18.80 | 0.00 | 1.44 | 5.69 |
| 422 | High | CuZnO Ref A | Ga | 5000 | 198.7 | 70.96 | 6.69 | 18.98 | 0.00 | 1.66 | 5.80 |
| 423 | High | CuZnO Ref A | Na | 1000 | 198.7 | 72.37 | 6.69 | 19.14 | 0.00 | 0.16 | 1.45 |
| 424 | High | CuZnO Ref A | Sr | 1000 | 198.7 | 71.96 | 6.74 | 19.52 | 0.00 | 0.15 | −0.33 |
| 425 | High | CuZnO Ref A | Sr | 5000 | 198.7 | 72.05 | 7.07 | 19.15 | 0.00 | 0.10 | −0.18 |
| 426 | High | CuZnO Ref A | Ba | 1000 | 198.7 | 72.00 | 7.13 | 19.14 | 0.00 | 0.08 | −0.02 |
| 427 | High | CuZnO Ref A | Ba | 1000 | 198.7 | 71.90 | 7.14 | 19.25 | 0.00 | 0.07 | −0.89 |
| 428 | High | CuZnO Ref A | Na | 1000 | 198.6 | 72.15 | 6.86 | 19.20 | 0.00 | 0.15 | 0.30 |
| 429 | High | CuZnO Ref A | Sr | 1000 | 198.6 | 72.06 | 6.66 | 19.51 | 0.00 | 0.14 | −0.02 |
| 430 | High | CuZnO Ref A | Li | 5000 | 198.6 | 72.01 | 6.75 | 19.46 | 0.00 | 0.12 | 0.63 |
| 431 | High | CuZnO Ref A | Sr | 5000 | 198.6 | 71.88 | 7.16 | 19.23 | 0.00 | 0.10 | −0.98 |
| 432 | High | CuZnO Ref A | Ga | 5000 | 198.4 | 71.07 | 6.50 | 19.05 | 0.00 | 1.67 | 6.41 |
| 433 | High | CuZnO Ref A | Na | 5000 | 198.4 | 71.24 | 6.91 | 18.69 | 0.00 | 1.45 | 5.86 |
| 434 | High | CuZnO Ref A | Li | 5000 | 198.4 | 71.97 | 6.81 | 19.44 | 0.00 | 0.13 | 0.21 |
| 435 | High | CuZnO Ref A | K | 5000 | 180.0 | 71.82 | 6.81 | 18.99 | 0.00 | 0.71 | 3.19 |
| 436 | High | CuZnO Ref A | Rb | 5000 | 180.0 | 72.06 | 6.65 | 19.02 | 0.00 | 0.62 | 3.43 |
| 437 | High | CuZnO Ref A | Rb | 5000 | 180.0 | 72.04 | 6.59 | 19.10 | 0.00 | 0.61 | 3.25 |
| 438 | High | CuZnO Ref A | Rb | 5000 | 180.0 | 72.25 | 6.67 | 18.81 | 0.00 | 0.60 | 4.44 |
| 439 | High | CuZnO Ref A | Li | 1000 | 180.0 | 72.65 | 6.48 | 19.16 | 0.00 | 0.08 | 1.78 |
| 440 | High | CuZnO Ref A | La | 1000 | 180.0 | 72.57 | 6.45 | 19.27 | 0.00 | 0.08 | 1.53 |
| 441 | High | CuZnO Ref A | Li | 1000 | 180.0 | 72.46 | 6.42 | 19.42 | 0.00 | 0.08 | 0.72 |
| 442 | High | CuZnO Ref A | Rb | 1000 | 180.0 | 72.77 | 6.57 | 18.94 | 0.00 | 0.07 | 3.12 |
| 443 | High | CuZnO Ref A | Rb | 1000 | 180.0 | 72.54 | 6.51 | 19.25 | 0.00 | 0.06 | 1.78 |
| 444 | High | CuZnO Ref A | K | 1000 | 180.0 | 72.65 | 6.54 | 19.11 | 0.00 | 0.06 | 1.95 |
| 445 | High | CuZnO Ref A | K | 1000 | 180.0 | 72.42 | 6.66 | 19.23 | 0.00 | 0.05 | 1.27 |
| 446 | High | CuZnO Ref A | K | 5000 | 179.9 | 71.88 | 6.79 | 18.96 | 0.00 | 0.70 | 3.50 |
| 447 | High | CuZnO Ref A | La | 5000 | 179.9 | 72.25 | 6.61 | 18.81 | 0.00 | 0.66 | 4.66 |
| 448 | High | CuZnO Ref A | La | 5000 | 179.9 | 72.24 | 6.58 | 18.87 | 0.00 | 0.64 | 4.29 |
| 449 | High | CuZnO Ref A | La | 5000 | 179.9 | 72.24 | 6.66 | 18.80 | 0.00 | 0.64 | 4.42 |
| 450 | High | CuZnO Ref A | La | 1000 | 179.9 | 72.63 | 6.52 | 19.13 | 0.00 | 0.07 | 1.87 |
| 451 | High | CuZnO Ref A | K | 5000 | 179.7 | 72.00 | 6.64 | 18.97 | 0.00 | 0.72 | 4.06 |
| 452 | High | CuZnO Ref A | La | 1000 | 179.7 | 72.43 | 6.50 | 19.37 | 0.00 | 0.08 | 0.67 |
| 453 | High | CuZnO Ref A | Li | 1000 | 179.7 | 72.57 | 6.50 | 19.23 | 0.00 | 0.07 | 1.13 |
| 454 | High | CuZnO Ref A | Na | 1000 | 179.2 | 72.39 | 6.64 | 19.26 | 0.00 | 0.07 | 0.80 |
| 455 | High | CuZnO Ref A | Sr | 5000 | 179.2 | 72.21 | 6.81 | 19.28 | 0.00 | 0.04 | 0.52 |
| 456 | High | CuZnO Ref A | Ga | 5000 | 179.1 | 71.75 | 6.57 | 19.23 | 0.00 | 0.77 | 3.50 |
| 457 | High | CuZnO Ref A | Na | 5000 | 179.1 | 72.13 | 6.56 | 18.96 | 0.00 | 0.66 | 4.85 |
| 458 | High | CuZnO Ref A | Ba | 1000 | 179.1 | 72.18 | 6.89 | 19.25 | 0.00 | 0.03 | 0.32 |
| 459 | High | CuZnO Ref A | Na | 5000 | 178.9 | 71.93 | 6.93 | 18.81 | 0.00 | 0.66 | 3.83 |
| 460 | High | CuZnO Ref A | Na | 1000 | 178.9 | 72.52 | 6.53 | 19.24 | 0.00 | 0.08 | 1.38 |
| 461 | High | CuZnO Ref A | Sr | 1000 | 178.9 | 72.12 | 6.69 | 19.49 | 0.00 | 0.07 | −0.39 |
| 462 | High | CuZnO Ref A | Sr | 1000 | 178.9 | 71.98 | 6.72 | 19.61 | 0.00 | 0.06 | −1.08 |
| 463 | High | CuZnO Ref A | Sr | 5000 | 178.9 | 72.07 | 7.01 | 19.23 | 0.00 | 0.04 | −0.36 |
| 464 | High | CuZnO Ref A | Ba | 1000 | 178.9 | 72.18 | 6.86 | 19.27 | 0.00 | 0.04 | 0.41 |
| 465 | High | CuZnO Ref A | Ga | 5000 | 178.8 | 71.70 | 6.68 | 19.17 | 0.00 | 0.77 | 3.37 |
| 466 | High | CuZnO Ref A | Li | 5000 | 178.5 | 72.18 | 6.76 | 19.36 | 0.00 | 0.06 | 0.44 |
| 467 | High | CuZnO Ref A | Li | 5000 | 178.5 | 72.19 | 6.79 | 19.31 | 0.00 | 0.05 | 0.74 |
| 468 | High | CuZnO Ref B | Ga | 5000 | 239.9 | 67.81 | 3.52 | 19.42 | 0.00 | 7.35 | 24.32 |
| 469 | High | CuZnO Ref B | Ga | 5000 | 239.9 | 67.75 | 3.44 | 19.57 | 0.00 | 7.34 | 24.16 |
| 470 | High | CuZnO Ref B | Ga | 5000 | 230.1 | 68.84 | 4.63 | 19.20 | 0.00 | 5.50 | 18.61 |
| 471 | High | CuZnO Ref B | Ga | 5000 | 229.9 | 69.01 | 4.57 | 19.17 | 0.00 | 5.41 | 19.20 |
| 472 | High | CuZnO Ref B | Ga | 5000 | 200.1 | 71.48 | 6.52 | 18.64 | 0.00 | 1.65 | 8.09 |
| 473 | High | CuZnO Ref B | Ga | 5000 | 199.8 | 71.41 | 6.40 | 18.84 | 0.00 | 1.63 | 7.79 |
| 474 | High | CuZnO Ref B | Ga | 5000 | 180.0 | 72.27 | 6.52 | 18.72 | 0.00 | 0.82 | 5.77 |
| 475 | High | CuZnO Ref B | Ga | 5000 | 180.0 | 72.07 | 6.56 | 18.91 | 0.00 | 0.78 | 4.93 |

TABLE 5

Activity of Promoted 1% Palladium on Copper Zinc Oxide Catalysts for Methanol Production

| Comp. Ex. No. | CO$_2$ Level | Support | Promoter | Promoter (ppm) | Temp (° C.) | H$_2$ wt % | CO wt % | CO$_2$ wt % | DME wt % | MeOH wt % | CO & CO$_2$ conv % |
|---|---|---|---|---|---|---|---|---|---|---|---|
| 476 | Low | CuZnO Ref A | Mn | 1000 | 240.1 | 59.68 | 25.34 | 3.08 | 0.00 | 9.97 | 23.61 |
| 477 | Low | CuZnO Ref A | Mg | 5000 | 240.1 | 60.49 | 25.55 | 2.82 | 0.00 | 9.23 | 22.94 |

TABLE 5-continued

Activity of Promoted 1% Palladium on Copper Zinc Oxide Catalysts for Methanol Production

| Comp. Ex. No. | $CO_2$ Level | Support | Promoter | Promoter (ppm) | Temp (° C.) | $H_2$ wt % | CO wt % | $CO_2$ wt % | DME wt % | MeOH wt % | CO & $CO_2$ conv % |
|---|---|---|---|---|---|---|---|---|---|---|---|
| 478 | Low | CuZnO Ref A | Mn | 1000 | 240.0 | 59.77 | 25.25 | 3.08 | 0.00 | 9.98 | 23.76 |
| 479 | Low | CuZnO Ref A | Mg | 5000 | 240.0 | 60.23 | 25.55 | 2.84 | 0.00 | 9.46 | 23.18 |
| 480 | Low | CuZnO Ref A | Mn | 5000 | 240.0 | 61.73 | 26.51 | 2.91 | 0.00 | 7.01 | 17.47 |
| 481 | Low | CuZnO Ref B | La | 5000 | 240.0 | 63.86 | 27.12 | 2.59 | 0.00 | 4.65 | 13.40 |
| 482 | Low | CuZnO Ref B | Ba | 1000 | 240.0 | 63.95 | 27.08 | 2.69 | 0.00 | 4.53 | 12.30 |
| 483 | Low | CuZnO Ref B | Ca | 5000 | 240.0 | 64.00 | 27.35 | 2.56 | 0.00 | 4.31 | 12.37 |
| 484 | Low | CuZnO Ref A | Ca | 1000 | 240.0 | 59.69 | 25.17 | 2.88 | 0.00 | 10.32 | 25.12 |
| 485 | Low | CuZnO Ref B | Ba | 1000 | 239.9 | 63.98 | 27.01 | 2.67 | 0.00 | 4.58 | 13.13 |
| 486 | Low | CuZnO Ref B | Ca | 5000 | 239.9 | 64.15 | 27.30 | 2.57 | 0.00 | 4.23 | 12.29 |
| 487 | Low | CuZnO Ref A | Ca | 1000 | 239.9 | 59.53 | 25.17 | 2.88 | 0.00 | 10.48 | 25.18 |
| 488 | Low | CuZnO Ref A | Mn | 5000 | 239.7 | 61.52 | 26.73 | 2.91 | 0.00 | 7.01 | 16.44 |
| 489 | Low | CuZnO Ref B | La | 5000 | 239.7 | 63.87 | 27.04 | 2.60 | 0.00 | 4.72 | 13.77 |
| 490 | Low | CuZnO Ref B | Na | 1000 | 239.7 | 65.53 | 28.49 | 2.61 | 0.00 | 1.68 | 4.91 |
| 491 | Low | CuZnO Ref B | Na | 1000 | 239.7 | 65.61 | 28.43 | 2.61 | 0.00 | 1.66 | 5.26 |
| 492 | Low | CuZnO Ref A | None |  | 238.8 | 61.90 | 26.15 | 2.93 | 0.00 | 7.17 | 18.38 |
| 493 | Low | CuZnO Ref B | Mg | 5000 | 238.8 | 62.99 | 27.08 | 2.81 | 0.00 | 5.32 | 13.67 |
| 494 | Low | CuZnO Ref A | La | 1000 | 238.7 | 60.61 | 25.63 | 2.83 | 0.00 | 9.03 | 22.42 |
| 495 | Low | CuZnO Ref A | Na | 1000 | 238.7 | 61.91 | 26.74 | 2.93 | 0.00 | 6.60 | 15.66 |
| 496 | Low | CuZnO Ref A | Ca | 5000 | 238.7 | 63.83 | 28.18 | 2.78 | 0.00 | 3.48 | 7.49 |
| 497 | Low | CuZnO Ref A | None |  | 238.7 | 59.25 | 24.67 | 3.15 | 0.01 | 10.96 | 26.58 |
| 498 | Low | CuZnO Ref A | None |  | 238.7 | 59.20 | 24.86 | 3.14 | 0.01 | 10.84 | 25.80 |
| 499 | Low | CuZnO Ref A | La | 1000 | 238.5 | 60.50 | 25.51 | 2.84 | 0.00 | 9.23 | 23.07 |
| 500 | Low | CuZnO Ref B | La | 1000 | 238.5 | 61.49 | 26.51 | 2.92 | 0.00 | 7.24 | 17.11 |
| 501 | Low | CuZnO Ref A | K | 5000 | 238.5 | 62.15 | 26.28 | 2.77 | 0.00 | 6.95 | 18.22 |
| 502 | Low | CuZnO Ref B | Mn | 5000 | 238.5 | 62.19 | 26.41 | 2.70 | 0.00 | 6.86 | 17.89 |
| 503 | Low | CuZnO Ref A | La | 5000 | 238.5 | 63.05 | 26.81 | 2.83 | 0.00 | 5.50 | 14.67 |
| 504 | Low | CuZnO Ref A | La | 5000 | 238.5 | 63.10 | 26.82 | 2.84 | 0.00 | 5.45 | 14.43 |
| 505 | Low | CuZnO Ref B | Ca | 5000 | 238.5 | 64.05 | 27.91 | 2.79 | 0.00 | 3.51 | 8.53 |
| 506 | Low | CuZnO Ref B | Ca | 1000 | 238.5 | 64.28 | 27.88 | 2.70 | 0.00 | 3.41 | 8.88 |
| 507 | Low | CuZnO Ref B | Ca | 1000 | 238.5 | 64.25 | 28.00 | 2.69 | 0.00 | 3.33 | 8.15 |
| 508 | Low | CuZnO Ref A | K | 1000 | 238.5 | 64.85 | 28.22 | 2.68 | 0.00 | 2.54 | 6.74 |
| 509 | Low | CuZnO Ref A | Na | 5000 | 238.5 | 65.34 | 28.26 | 2.46 | 0.00 | 2.22 | 7.24 |
| 510 | Low | CuZnO Ref A | Mg | 1000 | 238.5 | 58.40 | 24.44 | 3.20 | 0.00 | 11.98 | 28.07 |
| 511 | Low | CuZnO Ref A | Mg | 1000 | 238.5 | 58.18 | 24.90 | 3.17 | 0.00 | 11.77 | 26.51 |
| 512 | Low | CuZnO Ref B | La | 1000 | 238.4 | 61.51 | 26.34 | 2.93 | 0.00 | 7.37 | 17.92 |
| 513 | Low | CuZnO Ref B | None |  | 238.4 | 61.79 | 26.17 | 2.94 | 0.00 | 7.26 | 18.29 |
| 514 | Low | CuZnO Ref B | Mn | 5000 | 238.4 | 62.24 | 26.30 | 2.71 | 0.01 | 6.91 | 18.27 |
| 515 | Low | CuZnO Ref A | Na | 1000 | 238.4 | 61.88 | 26.89 | 2.93 | 0.00 | 6.48 | 15.04 |
| 516 | Low | CuZnO Ref B | Mg | 5000 | 238.4 | 62.91 | 27.02 | 2.82 | 0.00 | 5.46 | 13.97 |
| 517 | Low | CuZnO Ref B | K | 5000 | 238.4 | 64.57 | 28.29 | 2.67 | 0.00 | 2.76 | 6.70 |
| 518 | Low | CuZnO Ref B | K | 5000 | 238.4 | 64.54 | 28.44 | 2.66 | 0.00 | 2.64 | 5.72 |
| 519 | Low | CuZnO Ref B | Na | 5000 | 238.4 | 65.07 | 28.23 | 2.66 | 0.00 | 2.33 | 6.37 |
| 520 | Low | CuZnO Ref A | Ba | 1000 | 238.4 | 65.31 | 28.80 | 2.60 | 0.00 | 1.60 | 3.78 |
| 521 | Low | CuZnO Ref A | Ba | 1000 | 238.4 | 65.27 | 28.91 | 2.60 | 0.00 | 1.53 | 3.37 |
| 522 | Low | CuZnO Ref B | Mn | 1000 | 238.4 | 65.77 | 28.67 | 2.59 | 0.00 | 1.28 | 4.03 |
| 523 | Low | CuZnO Ref B | Mn | 1000 | 238.4 | 65.82 | 28.63 | 2.59 | 0.00 | 1.26 | 4.55 |
| 524 | Low | CuZnO Ref B | Mg | 1000 | 238.4 | 65.83 | 29.06 | 2.57 | 0.00 | 0.88 | 1.38 |
| 525 | Low | CuZnO Ref A | K | 5000 | 238.3 | 62.20 | 26.36 | 2.76 | 0.00 | 6.84 | 17.97 |
| 526 | Low | CuZnO Ref B | K | 1000 | 238.3 | 64.79 | 28.24 | 2.67 | 0.00 | 2.57 | 7.30 |
| 527 | Low | CuZnO Ref B | Na | 5000 | 238.3 | 65.13 | 28.23 | 2.65 | 0.00 | 2.28 | 6.36 |
| 528 | Low | CuZnO Ref A | Na | 5000 | 238.3 | 65.28 | 28.31 | 2.46 | 0.00 | 2.24 | 7.18 |
| 529 | Low | CuZnO Ref B | K | 1000 | 238.3 | 55.43 | 22.29 | 3.27 | 0.02 | 16.86 | 37.88 |
| 530 | Low | CuZnO Ref B | Mg | 1000 | 238.3 | 65.88 | 28.83 | 2.58 | 0.00 | 1.04 | 2.63 |
| 531 | Low | CuZnO Ref B | K | 1000 | 238.1 | 55.14 | 22.13 | 3.29 | 0.02 | 17.27 | 38.59 |
| 532 | Low | CuZnO Ref A | Ca | 1000 | 230.1 | 62.89 | 26.58 | 2.66 | 0.00 | 6.06 | 16.56 |
| 533 | Low | CuZnO Ref B | La | 5000 | 230.1 | 65.46 | 27.85 | 2.48 | 0.00 | 2.50 | 8.27 |
| 534 | Low | CuZnO Ref B | Ba | 1000 | 230.1 | 65.56 | 27.63 | 2.62 | 0.00 | 2.49 | 8.14 |
| 535 | Low | CuZnO Ref A | Mn | 1000 | 229.9 | 62.80 | 26.60 | 2.86 | 0.00 | 5.93 | 15.58 |
| 536 | Low | CuZnO Ref A | Mg | 5000 | 229.9 | 63.43 | 26.89 | 2.63 | 0.00 | 5.26 | 14.93 |
| 537 | Low | CuZnO Ref A | Mn | 5000 | 229.9 | 63.82 | 27.37 | 2.74 | 0.00 | 4.31 | 11.22 |
| 538 | Low | CuZnO Ref B | Ba | 1000 | 229.9 | 65.60 | 27.84 | 2.47 | 0.00 | 2.38 | 8.32 |
| 539 | Low | CuZnO Ref B | Ca | 5000 | 229.9 | 65.59 | 27.99 | 2.46 | 0.00 | 2.25 | 7.72 |
| 540 | Low | CuZnO Ref B | Na | 1000 | 229.9 | 66.03 | 28.71 | 2.58 | 0.00 | 1.00 | 3.21 |
| 541 | Low | CuZnO Ref A | Mg | 5000 | 229.8 | 63.49 | 26.80 | 2.62 | 0.00 | 5.29 | 15.03 |
| 542 | Low | CuZnO Ref B | La | 5000 | 229.8 | 65.48 | 27.65 | 2.49 | 0.00 | 2.66 | 9.32 |
| 543 | Low | CuZnO Ref B | Ca | 5000 | 229.8 | 65.64 | 28.03 | 2.45 | 0.00 | 2.17 | 7.27 |
| 544 | Low | CuZnO Ref A | Ca | 1000 | 229.7 | 62.87 | 26.65 | 2.65 | 0.00 | 6.01 | 16.37 |
| 545 | Low | CuZnO Ref A | Mn | 5000 | 229.7 | 63.99 | 27.40 | 2.74 | 0.00 | 4.11 | 11.70 |
| 546 | Low | CuZnO Ref A | La | 1000 | 228.8 | 63.63 | 26.93 | 2.62 | 0.00 | 5.03 | 14.26 |
| 547 | Low | CuZnO Ref B | Mn | 5000 | 228.8 | 64.57 | 27.24 | 2.55 | 0.00 | 3.90 | 11.78 |
| 548 | Low | CuZnO Ref B | La | 1000 | 228.6 | 63.94 | 27.21 | 2.76 | 0.00 | 4.34 | 12.02 |
| 549 | Low | CuZnO Ref A | La | 5000 | 228.6 | 64.89 | 27.72 | 2.70 | 0.00 | 2.97 | 8.52 |
| 550 | Low | CuZnO Ref A | Mg | 1000 | 228.5 | 61.77 | 26.24 | 2.93 | 0.00 | 7.22 | 17.89 |
| 551 | Low | CuZnO Ref A | None |  | 228.5 | 62.46 | 26.26 | 2.89 | 0.00 | 6.57 | 17.20 |

TABLE 5-continued

Activity of Promoted 1% Palladium on Copper Zinc Oxide Catalysts for Methanol Production

| Comp. Ex. No. | $CO_2$ Level | Support | Promoter | Promoter (ppm) | Temp (°C.) | $H_2$ wt % | CO wt % | $CO_2$ wt % | DME wt % | MeOH wt % | CO & $CO_2$ conv % |
|---|---|---|---|---|---|---|---|---|---|---|---|
| 552 | Low | CuZnO Ref A | None |  | 228.5 | 62.35 | 26.38 | 2.89 | 0.00 | 6.56 | 16.72 |
| 553 | Low | CuZnO Ref A | La | 1000 | 228.5 | 63.54 | 27.02 | 2.62 | 0.00 | 5.04 | 13.97 |
| 554 | Low | CuZnO Ref B | La | 1000 | 228.5 | 63.90 | 27.14 | 2.76 | 0.00 | 4.44 | 11.91 |
| 555 | Low | CuZnO Ref A | K | 5000 | 228.5 | 64.13 | 27.25 | 2.64 | 0.00 | 4.22 | 12.04 |
| 556 | Low | CuZnO Ref A | K | 5000 | 228.5 | 64.27 | 27.27 | 2.63 | 0.00 | 4.08 | 11.88 |
| 557 | Low | CuZnO Ref B | Mn | 5000 | 228.5 | 64.39 | 27.26 | 2.56 | 0.00 | 4.04 | 11.86 |
| 558 | Low | CuZnO Ref A | Na | 1000 | 228.5 | 64.17 | 27.62 | 2.76 | 0.00 | 3.69 | 10.15 |
| 559 | Low | CuZnO Ref A | Na | 1000 | 228.5 | 64.20 | 27.64 | 2.76 | 0.00 | 3.65 | 9.56 |
| 560 | Low | CuZnO Ref B | Mg | 5000 | 228.5 | 64.59 | 27.78 | 2.68 | 0.00 | 3.22 | 9.03 |
| 561 | Low | CuZnO Ref B | Mg | 5000 | 228.5 | 64.80 | 27.68 | 2.68 | 0.00 | 3.11 | 9.13 |
| 562 | Low | CuZnO Ref B | La | 5000 | 228.5 | 64.93 | 27.80 | 2.68 | 0.00 | 2.87 | 8.07 |
| 563 | Low | CuZnO Ref B | K | 1000 | 228.5 | 57.83 | 23.57 | 3.07 | 0.00 | 13.52 | 31.72 |
| 564 | Low | CuZnO Ref A | Ca | 5000 | 228.5 | 65.38 | 28.51 | 2.69 | 0.00 | 1.74 | 4.33 |
| 565 | Low | CuZnO Ref A | K | 1000 | 228.5 | 65.75 | 28.63 | 2.61 | 0.00 | 1.33 | 3.82 |
| 566 | Low | CuZnO Ref B | Na | 5000 | 228.5 | 65.80 | 28.64 | 2.61 | 0.00 | 1.28 | 3.42 |
| 567 | Low | CuZnO Ref B | Na | 5000 | 228.5 | 65.91 | 28.60 | 2.60 | 0.00 | 1.22 | 3.49 |
| 568 | Low | CuZnO Ref B | Na | 1000 | 228.5 | 66.07 | 28.72 | 2.57 | 0.00 | 0.97 | 3.07 |
| 569 | Low | CuZnO Ref B | Mg | 1000 | 228.5 | 66.08 | 28.90 | 2.56 | 0.00 | 0.80 | 1.75 |
| 570 | Low | CuZnO Ref B | Mn | 1000 | 228.5 | 66.09 | 28.90 | 2.57 | 0.00 | 0.78 | 2.53 |
| 571 | Low | CuZnO Ref A | Mg | 1000 | 228.3 | 61.78 | 26.06 | 2.94 | 0.00 | 7.37 | 18.90 |
| 572 | Low | CuZnO Ref A | Mn | 1000 | 228.3 | 62.73 | 26.69 | 2.86 | 0.00 | 5.92 | 15.33 |
| 573 | Low | CuZnO Ref B | None |  | 228.3 | 63.82 | 27.27 | 2.77 | 0.00 | 4.40 | 11.18 |
| 574 | Low | CuZnO Ref B | K | 1000 | 228.3 | 58.44 | 23.59 | 3.04 | 0.00 | 12.92 | 31.42 |
| 575 | Low | CuZnO Ref B | Ca | 1000 | 228.3 | 65.56 | 28.20 | 2.61 | 0.00 | 1.92 | 6.44 |
| 576 | Low | CuZnO Ref B | Ca | 1000 | 228.3 | 65.48 | 28.39 | 2.60 | 0.00 | 1.84 | 5.36 |
| 577 | Low | CuZnO Ref A | Ca | 5000 | 228.3 | 65.38 | 28.44 | 2.69 | 0.00 | 1.80 | 4.91 |
| 578 | Low | CuZnO Ref B | K | 5000 | 228.3 | 65.59 | 28.63 | 2.60 | 0.00 | 1.50 | 3.91 |
| 579 | Low | CuZnO Ref A | K | 1000 | 228.3 | 65.70 | 28.65 | 2.61 | 0.00 | 1.35 | 3.81 |
| 580 | Low | CuZnO Ref A | Na | 5000 | 228.3 | 66.16 | 28.59 | 2.41 | 0.00 | 1.16 | 4.69 |
| 581 | Low | CuZnO Ref A | Na | 5000 | 228.3 | 66.14 | 28.65 | 2.41 | 0.00 | 1.13 | 4.26 |
| 582 | Low | CuZnO Ref B | Mn | 1000 | 228.3 | 66.09 | 28.92 | 2.56 | 0.00 | 0.75 | 2.38 |
| 583 | Low | CuZnO Ref B | Mg | 1000 | 228.3 | 66.21 | 28.89 | 2.56 | 0.00 | 0.68 | 1.67 |
| 584 | Low | CuZnO Ref B | None |  | 228.2 | 64.07 | 27.19 | 2.76 | 0.00 | 4.22 | 11.65 |
| 585 | Low | CuZnO Ref B | K | 5000 | 228.2 | 65.21 | 28.82 | 2.64 | 0.00 | 1.59 | 6.21 |
| 586 | Low | CuZnO Ref A | Ba | 1000 | 228.2 | 65.87 | 29.00 | 2.56 | 0.00 | 0.90 | 2.34 |
| 587 | Low | CuZnO Ref A | Ba | 1000 | 228.0 | 65.89 | 28.93 | 2.56 | 0.00 | 0.96 | 1.81 |
| 588 | Low | CuZnO Ref A | Mg | 5000 | 200.0 | 66.94 | 28.42 | 2.41 | 0.00 | 0.57 | 4.22 |
| 589 | Low | CuZnO Ref A | Ca | 1000 | 200.0 | 66.96 | 28.43 | 2.40 | 0.00 | 0.56 | 3.52 |
| 590 | Low | CuZnO Ref A | Mn | 5000 | 200.0 | 66.57 | 28.69 | 2.55 | 0.00 | 0.53 | 2.28 |
| 591 | Low | CuZnO Ref B | La | 5000 | 200.0 | 66.86 | 28.66 | 2.41 | 0.00 | 0.42 | 2.86 |
| 592 | Low | CuZnO Ref B | Ba | 1000 | 200.0 | 66.92 | 28.63 | 2.41 | 0.00 | 0.39 | 2.94 |
| 593 | Low | CuZnO Ref B | Ca | 5000 | 200.0 | 66.82 | 28.77 | 2.40 | 0.00 | 0.36 | 2.38 |
| 594 | Low | CuZnO Ref B | Na | 1000 | 200.0 | 66.56 | 28.99 | 2.58 | 0.00 | 0.22 | 0.89 |
| 595 | Low | CuZnO Ref A | Mg | 5000 | 199.8 | 66.87 | 28.45 | 2.42 | 0.00 | 0.60 | 4.02 |
| 596 | Low | CuZnO Ref A | Mn | 1000 | 199.8 | 66.72 | 28.46 | 2.59 | 0.00 | 0.59 | 2.56 |
| 597 | Low | CuZnO Ref A | Mn | 5000 | 199.8 | 66.64 | 28.67 | 2.55 | 0.00 | 0.49 | 1.81 |
| 598 | Low | CuZnO Ref B | La | 5000 | 199.8 | 66.99 | 28.55 | 2.40 | 0.00 | 0.39 | 3.71 |
| 599 | Low | CuZnO Ref B | Ba | 1000 | 199.8 | 67.08 | 28.51 | 2.40 | 0.00 | 0.36 | 2.84 |
| 600 | Low | CuZnO Ref B | Ca | 5000 | 199.8 | 67.05 | 28.58 | 2.40 | 0.00 | 0.33 | 2.61 |
| 601 | Low | CuZnO Ref B | Na | 1000 | 199.8 | 66.59 | 28.97 | 2.57 | 0.00 | 0.21 | 0.91 |
| 602 | Low | CuZnO Ref A | Mn | 1000 | 199.6 | 66.70 | 28.45 | 2.59 | 0.00 | 0.60 | 2.57 |
| 603 | Low | CuZnO Ref A | Ca | 1000 | 199.6 | 66.82 | 28.51 | 2.41 | 0.00 | 0.59 | 3.53 |
| 604 | Low | CuZnO Ref A | Na | 1000 | 199.0 | 66.62 | 28.68 | 2.61 | 0.00 | 0.44 | 1.23 |
| 605 | Low | CuZnO Ref A | None |  | 198.9 | 66.72 | 28.37 | 2.59 | 0.00 | 0.68 | 2.91 |
| 606 | Low | CuZnO Ref B | None |  | 198.9 | 66.69 | 28.51 | 2.58 | 0.00 | 0.57 | 2.15 |
| 607 | Low | CuZnO Ref B | Mn | 5000 | 198.9 | 66.97 | 28.44 | 2.40 | 0.00 | 0.54 | 3.45 |
| 608 | Low | CuZnO Ref A | La | 5000 | 198.9 | 66.83 | 28.57 | 2.58 | 0.00 | 0.38 | 2.00 |
| 609 | Low | CuZnO Ref A | Ca | 5000 | 198.9 | 66.41 | 29.02 | 2.64 | 0.00 | 0.27 | 0.76 |
| 610 | Low | CuZnO Ref A | Mg | 1000 | 198.7 | 66.76 | 28.33 | 2.59 | 0.00 | 0.67 | 3.20 |
| 611 | Low | CuZnO Ref B | None |  | 198.7 | 66.79 | 28.38 | 2.58 | 0.00 | 0.60 | 2.72 |
| 612 | Low | CuZnO Ref B | La | 1000 | 198.7 | 66.94 | 28.46 | 2.42 | 0.00 | 0.52 | 3.27 |
| 613 | Low | CuZnO Ref B | Mn | 5000 | 198.7 | 67.03 | 28.42 | 2.40 | 0.00 | 0.51 | 3.24 |
| 614 | Low | CuZnO Ref A | Na | 1000 | 198.7 | 66.70 | 28.63 | 2.62 | 0.00 | 0.42 | 1.32 |
| 615 | Low | CuZnO Ref B | Ca | 1000 | 198.7 | 66.85 | 28.62 | 2.56 | 0.00 | 0.34 | 1.76 |
| 616 | Low | CuZnO Ref B | K | 1000 | 198.6 | 66.48 | 27.87 | 2.42 | 0.00 | 1.57 | 5.96 |
| 617 | Low | CuZnO Ref A | Mg | 1000 | 198.6 | 66.69 | 28.39 | 2.59 | 0.00 | 0.67 | 2.79 |
| 618 | Low | CuZnO Ref B | La | 1000 | 198.6 | 66.73 | 28.49 | 2.56 | 0.00 | 0.56 | 2.53 |
| 619 | Low | CuZnO Ref B | La | 1000 | 198.6 | 66.64 | 28.64 | 2.56 | 0.00 | 0.53 | 1.24 |
| 620 | Low | CuZnO Ref A | K | 5000 | 198.6 | 66.81 | 28.57 | 2.48 | 0.00 | 0.48 | 3.15 |
| 621 | Low | CuZnO Ref B | Mg | 5000 | 198.6 | 66.78 | 28.55 | 2.55 | 0.00 | 0.47 | 2.31 |
| 622 | Low | CuZnO Ref A | K | 5000 | 198.6 | 66.82 | 28.59 | 2.47 | 0.00 | 0.46 | 2.66 |
| 623 | Low | CuZnO Ref B | Mg | 5000 | 198.6 | 66.83 | 28.54 | 2.55 | 0.00 | 0.43 | 1.93 |
| 624 | Low | CuZnO Ref B | Ca | 1000 | 198.6 | 66.84 | 28.63 | 2.56 | 0.00 | 0.32 | 2.10 |
| 625 | Low | CuZnO Ref A | Ca | 5000 | 198.6 | 66.58 | 28.83 | 2.65 | 0.00 | 0.29 | 1.17 |

TABLE 5-continued

Activity of Promoted 1% Palladium on Copper Zinc Oxide Catalysts for Methanol Production

| Comp. Ex. No. | $CO_2$ Level | Support | Promoter | Promoter (ppm) | Temp (° C.) | $H_2$ wt % | CO wt % | $CO_2$ wt % | DME wt % | MeOH wt % | CO & $CO_2$ conv % |
|---|---|---|---|---|---|---|---|---|---|---|---|
| 626 | Low | CuZnO Ref B | K | 5000 | 198.6 | 66.53 | 28.98 | 2.57 | 0.00 | 0.27 | 0.84 |
| 627 | Low | CuZnO Ref B | Na | 5000 | 198.6 | 66.60 | 28.93 | 2.59 | 0.00 | 0.23 | 0.67 |
| 628 | Low | CuZnO Ref B | Mg | 1000 | 198.6 | 66.67 | 28.88 | 2.58 | 0.00 | 0.22 | 1.09 |
| 629 | Low | CuZnO Ref A | Ba | 1000 | 198.6 | 66.51 | 29.06 | 2.57 | 0.00 | 0.20 | 1.26 |
| 630 | Low | CuZnO Ref B | Mn | 1000 | 198.6 | 66.53 | 29.05 | 2.58 | 0.00 | 0.19 | 1.07 |
| 631 | Low | CuZnO Ref A | Na | 5000 | 198.6 | 66.81 | 28.95 | 2.40 | 0.00 | 0.19 | 1.40 |
| 632 | Low | CuZnO Ref B | Mn | 1000 | 198.6 | 66.50 | 29.09 | 2.57 | 0.00 | 0.18 | 0.69 |
| 633 | Low | CuZnO Ref B | K | 1000 | 198.4 | 66.56 | 27.65 | 2.46 | 0.00 | 1.65 | 7.50 |
| 634 | Low | CuZnO Ref A | None |  | 198.4 | 66.71 | 28.40 | 2.58 | 0.00 | 0.66 | 2.81 |
| 635 | Low | CuZnO Ref A | La | 1000 | 198.4 | 66.77 | 28.61 | 2.42 | 0.00 | 0.55 | 3.10 |
| 636 | Low | CuZnO Ref A | La | 5000 | 198.4 | 66.73 | 28.64 | 2.58 | 0.00 | 0.40 | 1.80 |
| 637 | Low | CuZnO Ref B | K | 5000 | 198.4 | 66.59 | 28.95 | 2.57 | 0.00 | 0.25 | 0.73 |
| 638 | Low | CuZnO Ref A | K | 1000 | 198.4 | 66.53 | 28.99 | 2.59 | 0.00 | 0.24 | 0.78 |
| 639 | Low | CuZnO Ref B | Na | 5000 | 198.4 | 66.63 | 28.91 | 2.59 | 0.00 | 0.22 | 0.72 |
| 640 | Low | CuZnO Ref A | Ba | 1000 | 198.4 | 66.43 | 29.14 | 2.56 | 0.00 | 0.22 | 0.95 |
| 641 | Low | CuZnO Ref A | Na | 5000 | 198.4 | 66.57 | 29.17 | 2.40 | 0.00 | 0.20 | 1.24 |
| 642 | Low | CuZnO Ref A | K | 1000 | 198.3 | 66.51 | 29.00 | 2.59 | 0.00 | 0.25 | 0.78 |
| 643 | Low | CuZnO Ref B | Mg | 1000 | 198.3 | 66.66 | 28.92 | 2.59 | 0.00 | 0.19 | 0.78 |
| 644 | Low | CuZnO Ref A | Mn | 1000 | 180.2 | 66.99 | 28.55 | 2.61 | 0.00 | 0.21 | 1.37 |
| 645 | Low | CuZnO Ref A | Mn | 1000 | 180.2 | 67.00 | 28.55 | 2.62 | 0.00 | 0.19 | 1.22 |
| 646 | Low | CuZnO Ref A | Mn | 5000 | 180.2 | 66.81 | 28.80 | 2.58 | 0.00 | 0.18 | 1.05 |
| 647 | Low | CuZnO Ref B | Ca | 5000 | 180.2 | 67.01 | 28.77 | 2.43 | 0.00 | 0.14 | 2.00 |
| 648 | Low | CuZnO Ref B | Na | 1000 | 180.2 | 66.73 | 28.92 | 2.61 | 0.00 | 0.09 | 0.75 |
| 649 | Low | CuZnO Ref A | Mn | 5000 | 180.0 | 66.81 | 28.76 | 2.56 | 0.00 | 0.23 | 1.03 |
| 650 | Low | CuZnO Ref A | Mg | 5000 | 180.0 | 66.96 | 28.75 | 2.43 | 0.00 | 0.21 | 1.88 |
| 651 | Low | CuZnO Ref A | Ca | 1000 | 180.0 | 67.12 | 28.61 | 2.43 | 0.00 | 0.20 | 2.55 |
| 652 | Low | CuZnO Ref A | Mg | 5000 | 180.0 | 67.09 | 28.63 | 2.44 | 0.00 | 0.19 | 2.48 |
| 653 | Low | CuZnO Ref A | Ca | 1000 | 180.0 | 67.15 | 28.58 | 2.43 | 0.00 | 0.19 | 2.66 |
| 654 | Low | CuZnO Ref B | La | 5000 | 180.0 | 67.01 | 28.75 | 2.44 | 0.00 | 0.16 | 1.96 |
| 655 | Low | CuZnO Ref B | Ba | 1000 | 180.0 | 67.09 | 28.68 | 2.43 | 0.00 | 0.15 | 2.24 |
| 656 | Low | CuZnO Ref B | Na | 1000 | 180.0 | 66.75 | 28.89 | 2.61 | 0.00 | 0.10 | 0.96 |
| 657 | Low | CuZnO Ref B | Ba | 1000 | 179.9 | 67.17 | 28.60 | 2.44 | 0.00 | 0.15 | 2.47 |
| 658 | Low | CuZnO Ref B | Ca | 5000 | 179.9 | 67.11 | 28.67 | 2.44 | 0.00 | 0.13 | 2.13 |
| 659 | Low | CuZnO Ref A | Mg | 1000 | 179.7 | 67.02 | 28.52 | 2.61 | 0.00 | 0.21 | 1.52 |
| 660 | Low | CuZnO Ref B | La | 5000 | 179.7 | 67.11 | 28.63 | 2.43 | 0.00 | 0.18 | 2.26 |
| 661 | Low | CuZnO Ref A | None |  | 179.4 | 66.93 | 28.62 | 2.60 | 0.00 | 0.22 | 0.94 |
| 662 | Low | CuZnO Ref A | Mg | 1000 | 179.1 | 67.11 | 28.43 | 2.61 | 0.00 | 0.21 | 1.62 |
| 663 | Low | CuZnO Ref B | Mn | 5000 | 179.1 | 67.28 | 28.44 | 2.43 | 0.00 | 0.19 | 3.07 |
| 664 | Low | CuZnO Ref B | Mg | 5000 | 179.1 | 67.04 | 28.57 | 2.57 | 0.00 | 0.18 | 1.75 |
| 665 | Low | CuZnO Ref B | Na | 1000 | 179.1 | 66.84 | 28.71 | 2.65 | 0.00 | 0.16 | 1.23 |
| 666 | Low | CuZnO Ref B | Ca | 1000 | 179.1 | 66.95 | 28.68 | 2.59 | 0.00 | 0.13 | 1.59 |
| 667 | Low | CuZnO Ref B | None |  | 178.9 | 67.05 | 28.50 | 2.61 | 0.00 | 0.21 | 1.54 |
| 668 | Low | CuZnO Ref A | La | 1000 | 178.9 | 67.08 | 28.63 | 2.46 | 0.00 | 0.19 | 2.46 |
| 669 | Low | CuZnO Ref A | Mg | 5000 | 178.9 | 67.01 | 28.60 | 2.58 | 0.00 | 0.17 | 1.76 |
| 670 | Low | CuZnO Ref A | Na | 1000 | 178.9 | 66.92 | 28.63 | 2.64 | 0.00 | 0.17 | 1.38 |
| 671 | Low | CuZnO Ref B | Ca | 1000 | 178.9 | 66.96 | 28.66 | 2.58 | 0.00 | 0.14 | 1.67 |
| 672 | Low | CuZnO Ref A | K | 5000 | 178.9 | 67.02 | 28.69 | 2.50 | 0.00 | 0.14 | 2.17 |
| 673 | Low | CuZnO Ref A | Ca | 5000 | 178.9 | 66.66 | 28.89 | 2.68 | 0.00 | 0.12 | 0.41 |
| 674 | Low | CuZnO Ref A | Ca | 5000 | 178.9 | 66.78 | 28.77 | 2.69 | 0.00 | 0.11 | 0.89 |
| 675 | Low | CuZnO Ref B | None |  | 178.8 | 67.00 | 28.54 | 2.60 | 0.00 | 0.22 | 1.31 |
| 676 | Low | CuZnO Ref A | None |  | 178.8 | 67.00 | 28.54 | 2.61 | 0.00 | 0.22 | 1.23 |
| 677 | Low | CuZnO Ref B | La | 1000 | 178.8 | 67.03 | 28.55 | 2.58 | 0.00 | 0.21 | 1.59 |
| 678 | Low | CuZnO Ref B | Mn | 5000 | 178.8 | 67.13 | 28.60 | 2.43 | 0.00 | 0.19 | 2.39 |
| 679 | Low | CuZnO Ref B | La | 1000 | 178.8 | 67.17 | 28.40 | 2.59 | 0.00 | 0.19 | 2.34 |
| 680 | Low | CuZnO Ref A | La | 1000 | 178.8 | 67.01 | 28.70 | 2.45 | 0.00 | 0.19 | 2.25 |
| 681 | Low | CuZnO Ref A | La | 5000 | 178.8 | 67.00 | 28.60 | 2.61 | 0.00 | 0.16 | 1.16 |
| 682 | Low | CuZnO Ref A | La | 5000 | 178.8 | 66.98 | 28.62 | 2.62 | 0.00 | 0.15 | 0.99 |
| 683 | Low | CuZnO Ref A | K | 5000 | 178.8 | 67.04 | 28.67 | 2.50 | 0.00 | 0.14 | 2.14 |
| 684 | Low | CuZnO Ref B | K | 1000 | 178.6 | 67.31 | 28.23 | 2.42 | 0.00 | 0.39 | 3.25 |
| 685 | Low | CuZnO Ref A | Ba | 1000 | 178.6 | 66.59 | 29.08 | 2.58 | 0.00 | 0.10 | 0.42 |
| 686 | Low | CuZnO Ref B | K | 1000 | 178.5 | 67.33 | 28.24 | 2.42 | 0.00 | 0.37 | 3.16 |
| 687 | Low | CuZnO Ref B | K | 5000 | 178.5 | 66.71 | 28.95 | 2.59 | 0.00 | 0.11 | 0.27 |
| 688 | Low | CuZnO Ref B | K | 5000 | 178.5 | 66.68 | 28.97 | 2.60 | 0.00 | 0.10 | 0.44 |
| 689 | Low | CuZnO Ref B | Mg | 1000 | 178.5 | 66.71 | 28.96 | 2.60 | 0.00 | 0.10 | 0.13 |
| 690 | Low | CuZnO Ref B | Na | 5000 | 178.5 | 66.71 | 28.93 | 2.63 | 0.00 | 0.10 | 0.12 |
| 691 | Low | CuZnO Ref A | K | 1000 | 178.5 | 66.63 | 29.00 | 2.62 | 0.00 | 0.10 | 0.40 |
| 692 | Low | CuZnO Ref B | Na | 5000 | 178.5 | 66.72 | 28.92 | 2.63 | 0.00 | 0.09 | 0.13 |
| 693 | Low | CuZnO Ref A | Ba | 1000 | 178.5 | 66.59 | 29.08 | 2.59 | 0.00 | 0.09 | 0.76 |
| 694 | Low | CuZnO Ref A | Mn | 1000 | 178.5 | 66.60 | 29.07 | 2.61 | 0.00 | 0.08 | 0.40 |
| 695 | Low | CuZnO Ref A | Na | 5000 | 178.5 | 66.84 | 28.99 | 2.44 | 0.00 | 0.08 | 1.67 |
| 696 | Low | CuZnO Ref A | Na | 5000 | 178.5 | 66.77 | 29.06 | 2.44 | 0.00 | 0.07 | 1.34 |
| 697 | Low | CuZnO Ref B | Mg | 1000 | 178.3 | 66.68 | 28.96 | 2.59 | 0.00 | 0.12 | 0.63 |
| 698 | Low | CuZnO Ref A | K | 1000 | 178.3 | 66.63 | 29.01 | 2.62 | 0.00 | 0.10 | 0.33 |
| 699 | Low | CuZnO Ref B | Mn | 1000 | 178.3 | 66.62 | 29.05 | 2.60 | 0.00 | 0.08 | 0.37 |

TABLE 5-continued

Activity of Promoted 1% Palladium on Copper Zinc Oxide Catalysts for Methanol Production

| Comp. Ex. No. | $CO_2$ Level | Support | Promoter | Promoter (ppm) | Temp (° C.) | $H_2$ wt % | CO wt % | $CO_2$ wt % | DME wt % | MeOH wt % | CO & $CO_2$ conv % |
|---|---|---|---|---|---|---|---|---|---|---|---|
| 700 | | | | | | | | | | | |
| 701 | High | CuZnO Ref B | None | | 240.1 | 69.21 | 4.61 | 18.87 | 0.00 | 5.46 | 20.11 |
| 702 | High | CuZnO Ref B | K | 1000 | 240.1 | 70.37 | 6.17 | 18.51 | 0.00 | 3.17 | 12.85 |
| 703 | High | CuZnO Ref A | K | 1000 | 240.0 | 67.55 | 4.69 | 20.17 | 0.00 | 5.79 | 13.78 |
| 704 | High | CuZnO Ref B | None | | 240.0 | 69.22 | 4.70 | 18.86 | 0.00 | 5.38 | 19.56 |
| 705 | High | CuZnO Ref B | Mg | 1000 | 240.0 | 69.38 | 4.71 | 18.80 | 0.00 | 5.29 | 19.73 |
| 706 | High | CuZnO Ref B | Ca | 5000 | 240.0 | 69.88 | 5.40 | 18.70 | 0.00 | 4.21 | 16.36 |
| 707 | High | CuZnO Ref B | Mn | 5000 | 240.0 | 69.97 | 5.87 | 18.75 | 0.00 | 3.64 | 13.35 |
| 708 | High | CuZnO Ref B | Mn | 5000 | 240.0 | 70.15 | 5.95 | 18.54 | 0.00 | 3.58 | 13.90 |
| 709 | High | CuZnO Ref B | K | 1000 | 240.0 | 70.15 | 6.13 | 18.77 | 0.00 | 3.19 | 11.58 |
| 710 | High | CuZnO Ref B | K | 5000 | 240.0 | 70.19 | 6.10 | 18.81 | 0.00 | 3.14 | 11.70 |
| 711 | High | CuZnO Ref A | Ca | 1000 | 240.0 | 71.47 | 5.13 | 18.55 | 0.00 | 3.07 | 16.55 |
| 712 | High | CuZnO Ref A | None | | 239.9 | 67.48 | 3.52 | 19.72 | 0.00 | 7.40 | 22.97 |
| 713 | High | CuZnO Ref A | K | 1000 | 239.9 | 67.38 | 4.70 | 20.21 | 0.00 | 5.91 | 13.28 |
| 714 | High | CuZnO Ref A | K | 1000 | 239.9 | 67.54 | 4.67 | 20.14 | 0.00 | 5.85 | 13.69 |
| 715 | High | CuZnO Ref B | None | | 239.9 | 69.25 | 4.71 | 18.79 | 0.00 | 5.42 | 20.22 |
| 716 | High | CuZnO Ref B | Mg | 1000 | 239.9 | 69.19 | 4.73 | 18.85 | 0.00 | 5.39 | 19.41 |
| 717 | High | CuZnO Ref B | Mg | 1000 | 239.9 | 69.32 | 4.62 | 18.89 | 0.00 | 5.33 | 19.72 |
| 718 | High | CuZnO Ref A | K | 5000 | 239.9 | 69.14 | 4.60 | 19.22 | 0.00 | 5.22 | 18.06 |
| 719 | High | CuZnO Ref A | K | 5000 | 239.9 | 69.18 | 4.73 | 19.27 | 0.00 | 5.02 | 17.04 |
| 720 | High | CuZnO Ref A | K | 5000 | 239.9 | 69.38 | 4.73 | 19.16 | 0.00 | 4.93 | 17.25 |
| 721 | High | CuZnO Ref B | Na | 1000 | 239.9 | 69.62 | 5.03 | 18.75 | 0.00 | 4.77 | 18.38 |
| 722 | High | CuZnO Ref B | K | 5000 | 239.9 | 70.37 | 6.04 | 18.62 | 0.00 | 3.20 | 13.06 |
| 723 | High | CuZnO Ref A | Ca | 1000 | 239.9 | 71.39 | 5.21 | 18.55 | 0.00 | 3.08 | 16.17 |
| 724 | High | CuZnO Ref A | Ca | 1000 | 239.9 | 71.33 | 5.29 | 18.53 | 0.00 | 3.07 | 15.92 |
| 725 | High | CuZnO Ref A | None | | 239.7 | 68.12 | 3.42 | 19.25 | 0.00 | 7.30 | 25.58 |
| 726 | High | CuZnO Ref A | Mg | 5000 | 239.7 | 68.79 | 4.39 | 19.00 | 0.00 | 5.96 | 21.18 |
| 727 | High | CuZnO Ref A | Na | 1000 | 239.7 | 69.51 | 5.07 | 18.88 | 0.00 | 4.71 | 17.76 |
| 728 | High | CuZnO Ref B | Ca | 5000 | 239.7 | 69.94 | 5.38 | 18.62 | 0.00 | 4.25 | 17.00 |
| 729 | High | CuZnO Ref B | Ca | 5000 | 239.7 | 69.89 | 5.53 | 18.60 | 0.00 | 4.18 | 16.04 |
| 730 | High | CuZnO Ref B | Mn | 5000 | 239.7 | 70.13 | 5.85 | 18.55 | 0.00 | 3.68 | 14.65 |
| 731 | High | CuZnO Ref B | Mg | 5000 | 239.6 | 68.58 | 4.49 | 19.04 | 0.00 | 6.03 | 20.59 |
| 732 | High | CuZnO Ref B | K | 1000 | 239.6 | 70.41 | 6.19 | 18.58 | 0.00 | 3.04 | 12.90 |
| 733 | High | CuZnO Ref B | Na | 5000 | 238.8 | 69.80 | 5.12 | 18.75 | 0.00 | 4.52 | 17.37 |
| 734 | High | CuZnO Ref A | La | 1000 | 238.7 | 67.71 | 3.47 | 19.48 | 0.00 | 7.44 | 24.30 |
| 735 | High | CuZnO Ref A | Na | 5000 | 238.7 | 68.65 | 4.82 | 19.78 | 0.00 | 4.96 | 13.64 |
| 736 | High | CuZnO Ref A | La | 1000 | 238.5 | 67.99 | 3.21 | 19.31 | 0.00 | 7.57 | 26.25 |
| 737 | High | CuZnO Ref A | Na | 1000 | 238.5 | 67.89 | 3.67 | 19.21 | 0.00 | 7.32 | 24.79 |
| 738 | High | CuZnO Ref B | La | 1000 | 238.5 | 68.33 | 3.56 | 19.32 | 0.00 | 6.90 | 24.22 |
| 739 | High | CuZnO Ref A | Mg | 1000 | 238.5 | 68.39 | 3.95 | 19.32 | 0.00 | 6.47 | 22.21 |
| 740 | High | CuZnO Ref A | La | 5000 | 238.5 | 68.57 | 4.49 | 19.01 | 0.00 | 6.06 | 20.95 |
| 741 | High | CuZnO Ref A | Ca | 5000 | 238.5 | 69.92 | 5.45 | 18.69 | 0.00 | 4.13 | 16.57 |
| 742 | High | CuZnO Ref A | Ca | 5000 | 238.5 | 69.78 | 5.60 | 18.71 | 0.00 | 4.10 | 15.71 |
| 743 | High | CuZnO Ref B | Ba | 1000 | 238.5 | 70.52 | 6.12 | 18.57 | 0.00 | 3.01 | 12.92 |
| 744 | High | CuZnO Ref B | Ba | 1000 | 238.5 | 70.38 | 6.27 | 18.59 | 0.00 | 2.97 | 12.34 |
| 745 | High | CuZnO Ref A | Ba | 1000 | 238.4 | 65.88 | 3.02 | 20.26 | 0.00 | 8.94 | 23.43 |
| 746 | High | CuZnO Ref A | Ba | 1000 | 238.4 | 66.06 | 2.98 | 20.22 | 0.00 | 8.84 | 23.66 |
| 747 | High | CuZnO Ref B | Na | 1000 | 238.4 | 67.93 | 3.82 | 19.17 | 0.00 | 7.18 | 24.29 |
| 748 | High | CuZnO Ref B | La | 1000 | 238.4 | 68.27 | 3.44 | 19.34 | 0.00 | 7.06 | 24.42 |
| 749 | High | CuZnO Ref B | Ca | 1000 | 238.4 | 68.36 | 4.09 | 19.03 | 0.00 | 6.63 | 22.88 |
| 750 | High | CuZnO Ref B | Ca | 1000 | 238.4 | 68.37 | 4.13 | 19.04 | 0.00 | 6.58 | 22.56 |
| 751 | High | CuZnO Ref A | Mg | 1000 | 238.4 | 68.56 | 3.95 | 19.27 | 0.00 | 6.35 | 22.31 |
| 752 | High | CuZnO Ref A | La | 5000 | 238.4 | 68.72 | 4.53 | 18.84 | 0.00 | 6.04 | 21.44 |
| 753 | High | CuZnO Ref A | Mn | 5000 | 238.4 | 68.54 | 5.01 | 19.12 | 0.00 | 5.50 | 17.80 |
| 754 | High | CuZnO Ref B | Mg | 5000 | 238.4 | 68.97 | 5.04 | 18.81 | 0.00 | 5.35 | 18.89 |
| 755 | High | CuZnO Ref A | Na | 5000 | 238.4 | 68.64 | 4.85 | 19.93 | 0.00 | 4.81 | 12.75 |
| 756 | High | CuZnO Ref B | Mn | 1000 | 238.4 | 70.20 | 5.83 | 18.46 | 0.00 | 3.71 | 15.32 |
| 757 | High | CuZnO Ref B | Mn | 1000 | 238.4 | 69.94 | 6.00 | 18.60 | 0.00 | 3.66 | 14.11 |
| 758 | High | CuZnO Ref A | Mn | 1000 | 238.4 | 70.79 | 6.85 | 18.41 | 0.00 | 2.18 | 10.15 |
| 759 | High | CuZnO Ref A | Mn | 1000 | 238.4 | 70.70 | 6.88 | 18.51 | 0.00 | 2.16 | 9.63 |
| 760 | High | CuZnO Ref B | Mn | 5000 | 238.3 | 68.48 | 4.91 | 19.19 | 0.00 | 5.59 | 18.12 |
| 761 | High | CuZnO Ref B | Mg | 5000 | 238.3 | 69.03 | 4.91 | 18.80 | 0.00 | 5.42 | 19.40 |
| 762 | High | CuZnO Ref B | Na | 5000 | 238.3 | 69.75 | 5.15 | 18.83 | 0.00 | 4.45 | 16.93 |
| 763 | High | CuZnO Ref A | Mg | 5000 | 230.2 | 70.19 | 5.52 | 18.64 | 0.00 | 3.85 | 15.72 |
| 764 | High | CuZnO Ref B | None | | 230.1 | 70.34 | 5.65 | 18.65 | 0.00 | 3.59 | 14.34 |
| 765 | High | CuZnO Ref B | K | 5000 | 230.1 | 71.16 | 6.42 | 18.53 | 0.00 | 2.14 | 10.46 |
| 766 | High | CuZnO Ref A | None | | 229.9 | 69.30 | 4.65 | 19.29 | 0.00 | 4.94 | 17.50 |
| 767 | High | CuZnO Ref A | None | | 229.9 | 69.38 | 4.92 | 18.94 | 0.00 | 4.93 | 18.41 |
| 768 | High | CuZnO Ref A | Mg | 5000 | 229.9 | 70.01 | 5.54 | 18.74 | 0.00 | 3.92 | 15.12 |
| 769 | High | CuZnO Ref A | K | 1000 | 229.9 | 68.87 | 5.77 | 19.72 | 0.00 | 3.89 | 8.65 |
| 770 | High | CuZnO Ref A | K | 1000 | 229.9 | 68.90 | 5.68 | 19.87 | 0.00 | 3.80 | 8.17 |
| 771 | High | CuZnO Ref B | Mg | 1000 | 229.9 | 70.58 | 5.55 | 18.49 | 0.00 | 3.60 | 15.39 |
| 772 | High | CuZnO Ref B | None | | 229.9 | 70.42 | 5.73 | 18.59 | 0.00 | 3.49 | 14.21 |
| 773 | High | CuZnO Ref B | Na | 1000 | 229.9 | 70.39 | 5.97 | 18.67 | 0.00 | 3.21 | 12.68 |

TABLE 5-continued

Activity of Promoted 1% Palladium on Copper Zinc Oxide Catalysts for Methanol Production

| Comp. Ex. No. | $CO_2$ Level | Support | Promoter | Promoter (ppm) | Temp (°C.) | $H_2$ wt % | CO wt % | $CO_2$ wt % | DME wt % | MeOH wt % | CO & $CO_2$ conv % |
|---|---|---|---|---|---|---|---|---|---|---|---|
| 774 | High | CuZnO Ref B | Ca | 5000 | 229.9 | 70.75 | 6.22 | 18.50 | 0.00 | 2.77 | 11.64 |
| 775 | High | CuZnO Ref B | Ca | 5000 | 229.9 | 70.85 | 6.24 | 18.45 | 0.00 | 2.72 | 11.83 |
| 776 | High | CuZnO Ref B | K | 5000 | 229.9 | 70.87 | 6.44 | 18.72 | 0.00 | 2.22 | 9.98 |
| 777 | High | CuZnO Ref A | Mg | 5000 | 229.8 | 70.02 | 5.56 | 18.65 | 0.00 | 3.98 | 15.49 |
| 778 | High | CuZnO Ref B | None |  | 229.8 | 70.52 | 5.65 | 18.50 | 0.00 | 3.55 | 15.02 |
| 779 | High | CuZnO Ref B | Mg | 1000 | 229.8 | 70.49 | 5.69 | 18.55 | 0.00 | 3.50 | 14.43 |
| 780 | High | CuZnO Ref B | Mg | 1000 | 229.8 | 70.46 | 5.78 | 18.52 | 0.00 | 3.47 | 14.08 |
| 781 | High | CuZnO Ref B | Na | 1000 | 229.8 | 70.70 | 5.87 | 18.57 | 0.00 | 3.09 | 13.39 |
| 782 | High | CuZnO Ref B | Ca | 5000 | 229.8 | 70.94 | 6.11 | 18.46 | 0.00 | 2.74 | 12.35 |
| 783 | High | CuZnO Ref A | K | 1000 | 229.7 | 68.72 | 5.72 | 19.85 | 0.00 | 3.96 | 8.39 |
| 784 | High | CuZnO Ref A | Na | 5000 | 228.8 | 69.81 | 5.50 | 19.71 | 0.00 | 3.25 | 8.99 |
| 785 | High | CuZnO Ref A | Na | 1000 | 228.6 | 69.32 | 5.16 | 18.81 | 0.00 | 4.89 | 17.58 |
| 786 | High | CuZnO Ref A | La | 5000 | 228.6 | 70.07 | 5.85 | 18.48 | 0.00 | 3.81 | 14.83 |
| 787 | High | CuZnO Ref B | Na | 5000 | 228.6 | 70.50 | 5.92 | 18.83 | 0.00 | 3.00 | 11.68 |
| 788 | High | CuZnO Ref A | Ba | 1000 | 228.5 | 67.60 | 4.27 | 19.95 | 0.00 | 6.36 | 16.87 |
| 789 | High | CuZnO Ref A | La | 1000 | 228.5 | 69.48 | 4.69 | 19.03 | 0.00 | 4.98 | 18.50 |
| 790 | High | CuZnO Ref B | La | 1000 | 228.5 | 69.86 | 4.84 | 18.89 | 0.00 | 4.60 | 17.88 |
| 791 | High | CuZnO Ref B | La | 1000 | 228.5 | 69.89 | 4.92 | 18.83 | 0.00 | 4.54 | 17.99 |
| 792 | High | CuZnO Ref A | Mg | 1000 | 228.5 | 69.91 | 5.17 | 18.83 | 0.00 | 4.28 | 17.03 |
| 793 | High | CuZnO Ref B | Ca | 1000 | 228.5 | 69.67 | 5.55 | 18.73 | 0.00 | 4.26 | 15.41 |
| 794 | High | CuZnO Ref A | La | 5000 | 228.5 | 70.09 | 5.80 | 18.57 | 0.00 | 3.76 | 14.61 |
| 795 | High | CuZnO Ref B | Mg | 5000 | 228.5 | 70.13 | 5.96 | 18.67 | 0.00 | 3.47 | 13.14 |
| 796 | High | CuZnO Ref B | Mg | 5000 | 228.5 | 70.08 | 6.11 | 18.63 | 0.00 | 3.40 | 12.46 |
| 797 | High | CuZnO Ref A | K | 5000 | 228.5 | 70.34 | 5.58 | 19.05 | 0.00 | 3.28 | 12.20 |
| 798 | High | CuZnO Ref A | Ca | 5000 | 228.5 | 70.88 | 6.35 | 18.40 | 0.00 | 2.61 | 12.06 |
| 799 | High | CuZnO Ref A | Ca | 5000 | 228.5 | 70.80 | 6.33 | 18.51 | 0.00 | 2.61 | 11.49 |
| 800 | High | CuZnO Ref B | Mn | 5000 | 228.5 | 70.94 | 6.52 | 18.45 | 0.00 | 2.36 | 10.23 |
| 801 | High | CuZnO Ref B | K | 1000 | 228.5 | 71.14 | 6.62 | 18.42 | 0.00 | 2.08 | 9.71 |
| 802 | High | CuZnO Ref B | K | 1000 | 228.5 | 70.82 | 6.62 | 18.77 | 0.00 | 2.06 | 7.70 |
| 803 | High | CuZnO Ref B | Ba | 1000 | 228.5 | 71.12 | 6.65 | 18.44 | 0.00 | 2.06 | 9.59 |
| 804 | High | CuZnO Ref A | Ca | 1000 | 228.5 | 72.26 | 5.74 | 18.20 | 0.00 | 2.06 | 13.88 |
| 805 | High | CuZnO Ref B | Ba | 1000 | 228.5 | 71.01 | 6.71 | 18.51 | 0.00 | 2.03 | 9.31 |
| 806 | High | CuZnO Ref A | Ba | 1000 | 228.3 | 67.61 | 4.43 | 19.94 | 0.00 | 6.19 | 16.12 |
| 807 | High | CuZnO Ref A | La | 1000 | 228.3 | 69.27 | 4.71 | 19.09 | 0.00 | 5.12 | 18.35 |
| 808 | High | CuZnO Ref A | Na | 1000 | 228.3 | 69.26 | 5.23 | 18.97 | 0.00 | 4.73 | 16.49 |
| 809 | High | CuZnO Ref A | Ca | 1000 | 228.3 | 69.82 | 5.28 | 18.73 | 0.00 | 4.36 | 16.61 |
| 810 | High | CuZnO Ref A | Mg | 1000 | 228.3 | 69.89 | 5.39 | 18.76 | 0.00 | 4.15 | 16.14 |
| 811 | High | CuZnO Ref A | Mn | 5000 | 228.3 | 69.81 | 6.06 | 18.70 | 0.00 | 3.64 | 13.00 |
| 812 | High | CuZnO Ref A | Mn | 5000 | 228.3 | 69.69 | 6.17 | 18.79 | 0.00 | 3.57 | 11.93 |
| 813 | High | CuZnO Ref A | K | 5000 | 228.3 | 70.23 | 5.40 | 19.07 | 0.00 | 3.54 | 13.08 |
| 814 | High | CuZnO Ref A | K | 5000 | 228.3 | 70.45 | 5.36 | 19.01 | 0.00 | 3.41 | 13.39 |
| 815 | High | CuZnO Ref A | Na | 5000 | 228.3 | 69.50 | 5.71 | 19.64 | 0.00 | 3.41 | 8.49 |
| 816 | High | CuZnO Ref B | Na | 5000 | 228.3 | 70.79 | 5.98 | 18.57 | 0.00 | 2.90 | 12.48 |
| 817 | High | CuZnO Ref B | Mn | 1000 | 228.3 | 70.72 | 6.57 | 18.46 | 0.00 | 2.49 | 10.76 |
| 818 | High | CuZnO Ref B | Mn | 5000 | 228.3 | 70.91 | 6.48 | 18.58 | 0.00 | 2.29 | 9.63 |
| 819 | High | CuZnO Ref A | Ca | 1000 | 228.3 | 72.12 | 5.78 | 18.33 | 0.00 | 2.03 | 13.30 |
| 820 | High | CuZnO Ref A | Mn | 1000 | 228.3 | 71.18 | 7.05 | 18.46 | 0.00 | 1.56 | 8.07 |
| 821 | High | CuZnO Ref A | Mn | 1000 | 228.3 | 78.24 | 7.81 | 10.91 | 0.00 | 1.11 | 39.00 |
| 822 | High | CuZnO Ref B | Mn | 1000 | 228.2 | 70.83 | 6.45 | 18.54 | 0.00 | 2.43 | 10.58 |
| 823 | High | CuZnO Ref B | Mn | 5000 | 228.2 | 71.05 | 6.52 | 18.38 | 0.00 | 2.31 | 10.46 |
| 824 | High | CuZnO Ref A | Ca | 1000 | 228.2 | 72.22 | 5.63 | 18.32 | 0.00 | 2.09 | 13.84 |
| 825 | High | CuZnO Ref B | K | 1000 | 228.0 | 71.18 | 6.64 | 18.37 | 0.00 | 2.07 | 9.82 |
| 826 | High | CuZnO Ref B | Ca | 5000 | 200.3 | 72.04 | 6.67 | 18.74 | 0.00 | 0.86 | 5.06 |
| 827 | High | CuZnO Ref A | None |  | 200.1 | 71.86 | 6.49 | 18.72 | 0.00 | 1.23 | 7.11 |
| 828 | High | CuZnO Ref B | None |  | 200.1 | 72.21 | 6.51 | 18.59 | 0.00 | 1.00 | 6.62 |
| 829 | High | CuZnO Ref B | Ca | 5000 | 200.1 | 72.07 | 6.73 | 18.68 | 0.00 | 0.84 | 5.24 |
| 830 | High | CuZnO Ref B | Ca | 5000 | 200.1 | 72.25 | 6.64 | 18.59 | 0.00 | 0.83 | 5.97 |
| 831 | High | CuZnO Ref B | K | 5000 | 200.1 | 71.88 | 6.82 | 18.90 | 0.00 | 0.72 | 4.37 |
| 832 | High | CuZnO Ref A | None |  | 200.0 | 71.74 | 6.68 | 18.66 | 0.00 | 1.22 | 6.55 |
| 833 | High | CuZnO Ref B | K | 1000 | 200.0 | 70.60 | 6.76 | 19.89 | 0.00 | 1.11 | −1.15 |
| 834 | High | CuZnO Ref A | Mg | 5000 | 200.0 | 72.05 | 6.63 | 18.59 | 0.00 | 1.05 | 6.55 |
| 835 | High | CuZnO Ref B | Mg | 1000 | 200.0 | 72.28 | 6.45 | 18.56 | 0.00 | 1.03 | 6.53 |
| 836 | High | CuZnO Ref B | None |  | 200.0 | 72.21 | 6.52 | 18.56 | 0.00 | 1.02 | 6.82 |
| 837 | High | CuZnO Ref A | K | 5000 | 200.0 | 72.02 | 6.50 | 18.78 | 0.00 | 1.02 | 5.68 |
| 838 | High | CuZnO Ref A | K | 5000 | 200.0 | 72.05 | 6.47 | 18.82 | 0.00 | 0.99 | 5.54 |
| 839 | High | CuZnO Ref B | Na | 1000 | 200.0 | 71.92 | 6.61 | 18.83 | 0.00 | 0.95 | 5.72 |
| 840 | High | CuZnO Ref B | Mn | 5000 | 200.0 | 72.04 | 6.73 | 18.74 | 0.00 | 0.81 | 5.28 |
| 841 | High | CuZnO Ref B | K | 5000 | 200.0 | 71.84 | 6.78 | 18.99 | 0.00 | 0.70 | 4.33 |
| 842 | High | CuZnO Ref A | Ca | 1000 | 200.0 | 73.13 | 6.47 | 18.04 | 0.00 | 0.66 | 9.01 |
| 843 | High | CuZnO Ref A | Ca | 1000 | 200.0 | 73.20 | 6.41 | 18.06 | 0.00 | 0.65 | 9.02 |
| 844 | High | CuZnO Ref A | K | 1000 | 199.8 | 70.63 | 6.76 | 19.83 | 0.00 | 1.13 | −0.36 |
| 845 | High | CuZnO Ref A | Mg | 5000 | 199.8 | 71.98 | 6.67 | 18.58 | 0.00 | 1.08 | 6.27 |
| 846 | High | CuZnO Ref B | Mg | 1000 | 199.8 | 72.21 | 6.57 | 18.54 | 0.00 | 1.00 | 6.05 |
| 847 | High | CuZnO Ref B | None |  | 199.8 | 72.12 | 6.65 | 18.57 | 0.00 | 0.99 | 6.00 |

TABLE 5-continued

Activity of Promoted 1% Palladium on Copper Zinc Oxide Catalysts for Methanol Production

| Comp. Ex. No. | $CO_2$ Level | Support | Promoter | Promoter (ppm) | Temp (° C.) | $H_2$ wt % | CO wt % | $CO_2$ wt % | DME wt % | MeOH wt % | CO & $CO_2$ conv % |
|---|---|---|---|---|---|---|---|---|---|---|---|
| 848 | High | CuZnO Ref A | K | 5000 | 199.8 | 72.03 | 6.54 | 18.78 | 0.00 | 0.98 | 5.42 |
| 849 | High | CuZnO Ref B | Na | 1000 | 199.8 | 71.91 | 6.72 | 18.70 | 0.00 | 0.98 | 5.72 |
| 850 | High | CuZnO Ref B | Mn | 5000 | 199.8 | 71.93 | 6.75 | 18.80 | 0.00 | 0.84 | 4.57 |
| 851 | High | CuZnO Ref B | Mn | 5000 | 199.8 | 72.16 | 6.79 | 18.56 | 0.00 | 0.80 | 5.68 |
| 852 | High | CuZnO Ref A | K | 1000 | 199.6 | 70.69 | 6.71 | 19.84 | 0.00 | 1.11 | −0.69 |
| 853 | High | CuZnO Ref B | Mg | 1000 | 199.6 | 72.24 | 6.58 | 18.52 | 0.00 | 0.98 | 6.29 |
| 854 | High | CuZnO Ref B | K | 1000 | 199.6 | 71.97 | 6.80 | 18.76 | 0.00 | 0.79 | 4.76 |
| 855 | High | CuZnO Ref B | K | 1000 | 199.6 | 71.56 | 6.77 | 19.24 | 0.00 | 0.77 | 2.36 |
| 856 | High | CuZnO Ref A | Ca | 1000 | 199.6 | 73.12 | 6.48 | 18.04 | 0.00 | 0.66 | 9.17 |
| 857 | High | CuZnO Ref A | Mg | 5000 | 199.5 | 72.05 | 6.68 | 18.52 | 0.00 | 1.06 | 6.61 |
| 858 | High | CuZnO Ref B | K | 1000 | 199.5 | 72.03 | 6.72 | 18.80 | 0.00 | 0.77 | 4.63 |
| 859 | High | CuZnO Ref B | Mg | 1000 | 199.0 | 71.73 | 6.67 | 18.75 | 0.00 | 1.15 | 6.09 |
| 860 | High | CuZnO Ref A | Na | 1000 | 198.7 | 71.57 | 6.80 | 18.71 | 0.00 | 1.23 | 5.45 |
| 861 | High | CuZnO Ref B | La | 1000 | 198.7 | 72.03 | 6.29 | 18.83 | 0.00 | 1.16 | 7.03 |
| 862 | High | CuZnO Ref B | Ca | 1000 | 198.7 | 71.70 | 6.69 | 18.77 | 0.00 | 1.16 | 5.35 |
| 863 | High | CuZnO Ref A | Mn | 5000 | 198.7 | 71.22 | 7.03 | 19.05 | 0.00 | 1.02 | 2.55 |
| 864 | High | CuZnO Ref A | La | 5000 | 198.7 | 71.75 | 6.88 | 18.71 | 0.00 | 0.99 | 4.60 |
| 865 | High | CuZnO Ref A | Na | 5000 | 198.7 | 70.99 | 6.56 | 19.82 | 0.00 | 0.97 | 0.37 |
| 866 | High | CuZnO Ref B | Na | 5000 | 198.7 | 71.95 | 6.61 | 18.86 | 0.00 | 0.90 | 4.98 |
| 867 | High | CuZnO Ref B | Na | 5000 | 198.7 | 71.95 | 6.59 | 18.91 | 0.00 | 0.88 | 4.89 |
| 868 | High | CuZnO Ref A | Ba | 1000 | 198.6 | 70.48 | 6.72 | 19.63 | 0.00 | 1.50 | 1.09 |
| 869 | High | CuZnO Ref A | La | 1000 | 198.6 | 71.67 | 6.54 | 18.80 | 0.00 | 1.29 | 6.43 |
| 870 | High | CuZnO Ref A | La | 1000 | 198.6 | 71.73 | 6.45 | 18.85 | 0.00 | 1.27 | 6.77 |
| 871 | High | CuZnO Ref A | Na | 1000 | 198.6 | 71.59 | 6.80 | 18.65 | 0.00 | 1.26 | 5.87 |
| 872 | High | CuZnO Ref B | Ca | 1000 | 198.6 | 71.83 | 6.65 | 18.65 | 0.00 | 1.18 | 6.20 |
| 873 | High | CuZnO Ref A | Mg | 1000 | 198.6 | 71.84 | 6.51 | 18.80 | 0.00 | 1.14 | 6.70 |
| 874 | High | CuZnO Ref A | Mn | 5000 | 198.6 | 71.36 | 7.06 | 18.85 | 0.00 | 1.04 | 3.82 |
| 875 | High | CuZnO Ref B | Mg | 5000 | 198.6 | 71.68 | 6.83 | 18.79 | 0.00 | 1.01 | 4.64 |
| 876 | High | CuZnO Ref A | Na | 5000 | 198.6 | 71.01 | 6.54 | 19.79 | 0.00 | 1.00 | 0.37 |
| 877 | High | CuZnO Ref A | La | 5000 | 198.6 | 71.73 | 6.88 | 18.74 | 0.00 | 0.98 | 4.52 |
| 878 | High | CuZnO Ref B | Mn | 1000 | 198.6 | 71.64 | 6.93 | 18.91 | 0.00 | 0.83 | 3.95 |
| 879 | High | CuZnO Ref B | Ba | 1000 | 198.6 | 71.77 | 6.74 | 19.06 | 0.00 | 0.75 | 4.08 |
| 880 | High | CuZnO Ref B | Ba | 1000 | 198.6 | 71.80 | 6.83 | 18.94 | 0.00 | 0.73 | 4.28 |
| 881 | High | CuZnO Ref A | Mn | 1000 | 198.6 | 71.74 | 7.14 | 18.84 | 0.00 | 0.58 | 4.13 |
| 882 | High | CuZnO Ref A | Ba | 1000 | 198.4 | 70.60 | 6.72 | 19.48 | 0.00 | 1.52 | 1.82 |
| 883 | High | CuZnO Ref B | La | 1000 | 198.4 | 71.81 | 6.47 | 18.85 | 0.00 | 1.18 | 6.07 |
| 884 | High | CuZnO Ref B | Mg | 5000 | 198.4 | 71.64 | 6.84 | 18.80 | 0.00 | 1.04 | 4.74 |
| 885 | High | CuZnO Ref B | Mn | 1000 | 198.4 | 71.72 | 6.88 | 18.87 | 0.00 | 0.85 | 4.43 |
| 886 | High | CuZnO Ref A | Ca | 5000 | 198.4 | 71.80 | 6.82 | 18.89 | 0.00 | 0.79 | 4.55 |
| 887 | High | CuZnO Ref A | Mn | 1000 | 198.4 | 71.70 | 7.07 | 18.96 | 0.00 | 0.59 | 3.50 |
| 888 | High | CuZnO Ref A | Ca | 5000 | 198.3 | 71.88 | 6.73 | 18.91 | 0.00 | 0.80 | 4.50 |
| 889 | High | CuZnO Ref A | Mg | 5000 | 180.3 | 72.30 | 6.63 | 18.90 | 0.00 | 0.50 | 3.71 |
| 890 | High | CuZnO Ref A | None | | 180.2 | 72.35 | 6.66 | 18.73 | 0.00 | 0.59 | 4.79 |
| 891 | High | CuZnO Ref B | None | | 180.2 | 72.34 | 6.59 | 18.89 | 0.00 | 0.52 | 3.76 |
| 892 | High | CuZnO Ref A | Mg | 5000 | 180.2 | 72.38 | 6.61 | 18.86 | 0.00 | 0.49 | 3.98 |
| 893 | High | CuZnO Ref B | None | | 180.2 | 72.35 | 6.47 | 19.04 | 0.00 | 0.48 | 3.43 |
| 894 | High | CuZnO Ref A | K | 5000 | 180.2 | 72.27 | 6.57 | 19.06 | 0.00 | 0.45 | 2.80 |
| 895 | High | CuZnO Ref B | Ca | 5000 | 180.2 | 72.32 | 6.61 | 18.97 | 0.00 | 0.44 | 3.34 |
| 896 | High | CuZnO Ref A | Ca | 1000 | 180.2 | 73.54 | 6.27 | 18.22 | 0.00 | 0.30 | 8.62 |
| 897 | High | CuZnO Ref B | Na | 1000 | 180.0 | 72.45 | 6.66 | 18.73 | 0.00 | 0.49 | 4.45 |
| 898 | High | CuZnO Ref B | Mg | 1000 | 180.0 | 72.52 | 6.48 | 18.88 | 0.00 | 0.48 | 3.53 |
| 899 | High | CuZnO Ref A | K | 5000 | 180.0 | 72.22 | 6.54 | 19.17 | 0.00 | 0.43 | 2.18 |
| 900 | High | CuZnO Ref B | Ca | 5000 | 180.0 | 72.24 | 6.61 | 19.09 | 0.00 | 0.41 | 2.65 |
| 901 | High | CuZnO Ref B | Mn | 5000 | 180.0 | 72.06 | 6.72 | 19.17 | 0.00 | 0.40 | 1.99 |
| 902 | High | CuZnO Ref B | K | 1000 | 180.0 | 72.11 | 6.66 | 19.20 | 0.00 | 0.38 | 2.32 |
| 903 | High | CuZnO Ref A | Ca | 1000 | 180.0 | 73.37 | 6.27 | 18.38 | 0.00 | 0.31 | 7.46 |
| 904 | High | CuZnO Ref A | None | | 179.9 | 72.25 | 6.65 | 18.86 | 0.00 | 0.57 | 4.32 |
| 905 | High | CuZnO Ref A | Mg | 5000 | 179.9 | 72.34 | 6.55 | 18.94 | 0.00 | 0.51 | 3.97 |
| 906 | High | CuZnO Ref B | Mg | 1000 | 179.9 | 72.47 | 6.49 | 18.91 | 0.00 | 0.49 | 2.92 |
| 907 | High | CuZnO Ref B | None | | 179.9 | 72.27 | 6.60 | 19.01 | 0.00 | 0.48 | 2.97 |
| 908 | High | CuZnO Ref B | Na | 1000 | 179.9 | 72.26 | 6.48 | 19.12 | 0.00 | 0.47 | 3.61 |
| 909 | High | CuZnO Ref A | K | 5000 | 179.9 | 72.21 | 6.57 | 19.13 | 0.00 | 0.44 | 2.24 |
| 910 | High | CuZnO Ref B | Mn | 5000 | 179.9 | 72.21 | 6.65 | 19.09 | 0.00 | 0.39 | 2.70 |
| 911 | High | CuZnO Ref B | K | 1000 | 179.9 | 72.22 | 6.69 | 19.06 | 0.00 | 0.37 | 2.69 |
| 912 | High | CuZnO Ref B | K | 5000 | 179.9 | 72.23 | 6.79 | 18.97 | 0.00 | 0.35 | 2.94 |
| 913 | High | CuZnO Ref B | K | 5000 | 179.9 | 72.15 | 6.80 | 19.05 | 0.00 | 0.34 | 2.93 |
| 914 | High | CuZnO Ref A | K | 1000 | 179.7 | 70.76 | 6.71 | 20.38 | 0.00 | 0.54 | −4.55 |
| 915 | High | CuZnO Ref B | Mg | 1000 | 179.7 | 72.66 | 6.43 | 18.74 | 0.00 | 0.53 | 3.83 |
| 916 | High | CuZnO Ref B | Ca | 5000 | 179.7 | 72.31 | 6.48 | 19.15 | 0.00 | 0.41 | 2.92 |
| 917 | High | CuZnO Ref B | K | 1000 | 179.7 | 72.32 | 6.63 | 18.99 | 0.00 | 0.40 | 3.59 |
| 918 | High | CuZnO Ref A | Ca | 1000 | 179.7 | 73.20 | 6.51 | 18.32 | 0.00 | 0.31 | 6.53 |
| 919 | High | CuZnO Ref A | K | 1000 | 179.6 | 70.84 | 6.71 | 20.30 | 0.00 | 0.53 | −4.11 |
| 920 | High | CuZnO Ref B | Mn | 5000 | 179.6 | 72.21 | 6.69 | 19.02 | 0.00 | 0.41 | 3.30 |
| 921 | High | CuZnO Ref A | K | 1000 | 179.4 | 70.93 | 6.73 | 20.17 | 0.00 | 0.54 | −3.35 |

TABLE 5-continued

Activity of Promoted 1% Palladium on Copper Zinc Oxide Catalysts for Methanol Production

| Comp. Ex. No. | $CO_2$ Level | Support | Promoter | Promoter (ppm) | Temp (° C.) | $H_2$ wt % | CO wt % | $CO_2$ wt % | DME wt % | MeOH wt % | CO & $CO_2$ conv % |
|---|---|---|---|---|---|---|---|---|---|---|---|
| 922 | High | CuZnO Ref A | Mg | 1000 | 179.2 | 72.20 | 6.59 | 19.00 | 0.00 | 0.54 | 3.76 |
| 923 | High | CuZnO Ref A | Mn | 5000 | 179.2 | 71.94 | 6.68 | 19.22 | 0.00 | 0.49 | 2.58 |
| 924 | High | CuZnO Ref A | Na | 5000 | 179.2 | 71.47 | 6.51 | 19.92 | 0.00 | 0.46 | −1.43 |
| 925 | High | CuZnO Ref A | Ba | 1000 | 179.1 | 71.11 | 6.79 | 19.77 | 0.00 | 0.69 | −1.54 |
| 926 | High | CuZnO Ref A | La | 1000 | 179.1 | 72.27 | 6.53 | 18.93 | 0.00 | 0.60 | 4.29 |
| 927 | High | CuZnO Ref A | Na | 1000 | 179.1 | 72.12 | 6.59 | 19.03 | 0.00 | 0.60 | 3.38 |
| 928 | High | CuZnO Ref A | Na | 1000 | 179.1 | 71.96 | 6.83 | 18.97 | 0.00 | 0.58 | 2.76 |
| 929 | High | CuZnO Ref B | Ca | 1000 | 179.1 | 72.15 | 6.58 | 19.04 | 0.00 | 0.57 | 3.23 |
| 930 | High | CuZnO Ref B | La | 1000 | 179.1 | 72.60 | 6.17 | 19.01 | 0.00 | 0.55 | 5.51 |
| 931 | High | CuZnO Ref B | Ca | 1000 | 179.1 | 72.18 | 6.65 | 18.96 | 0.00 | 0.55 | 3.30 |
| 932 | High | CuZnO Ref A | Mg | 1000 | 179.1 | 72.19 | 6.62 | 18.98 | 0.00 | 0.54 | 3.73 |
| 933 | High | CuZnO Ref B | Mg | 5000 | 179.1 | 72.14 | 6.71 | 18.98 | 0.00 | 0.51 | 3.16 |
| 934 | High | CuZnO Ref A | La | 5000 | 179.1 | 72.42 | 6.30 | 19.13 | 0.00 | 0.49 | 4.30 |
| 935 | High | CuZnO Ref B | Na | 5000 | 179.1 | 72.39 | 6.56 | 18.97 | 0.00 | 0.43 | 3.27 |
| 936 | High | CuZnO Ref A | Ca | 5000 | 179.1 | 72.08 | 6.73 | 19.14 | 0.00 | 0.38 | 2.31 |
| 937 | High | CuZnO Ref B | Ba | 1000 | 179.1 | 72.12 | 6.73 | 19.12 | 0.00 | 0.37 | 2.91 |
| 938 | High | CuZnO Ref A | Ba | 1000 | 178.9 | 71.14 | 6.65 | 19.87 | 0.00 | 0.71 | −1.42 |
| 939 | High | CuZnO Ref A | La | 1000 | 178.9 | 72.26 | 6.45 | 19.03 | 0.00 | 0.60 | 4.15 |
| 940 | High | CuZnO Ref B | Mg | 5000 | 178.9 | 71.97 | 6.79 | 19.10 | 0.00 | 0.49 | 2.20 |
| 941 | High | CuZnO Ref A | Na | 5000 | 178.9 | 71.48 | 6.57 | 19.85 | 0.00 | 0.46 | −1.44 |
| 942 | High | CuZnO Ref A | Ca | 5000 | 178.9 | 72.17 | 6.76 | 19.03 | 0.00 | 0.38 | 3.02 |
| 943 | High | CuZnO Ref B | La | 1000 | 178.8 | 72.41 | 6.42 | 18.94 | 0.00 | 0.56 | 4.51 |
| 944 | High | CuZnO Ref A | Mn | 5000 | 178.8 | 71.76 | 7.00 | 19.10 | 0.00 | 0.48 | 1.39 |
| 945 | High | CuZnO Ref A | La | 5000 | 178.8 | 72.19 | 6.79 | 18.91 | 0.00 | 0.45 | 2.87 |
| 946 | High | CuZnO Ref B | Na | 5000 | 178.8 | 72.35 | 6.52 | 19.06 | 0.00 | 0.42 | 3.03 |
| 947 | High | CuZnO Ref B | Ba | 1000 | 178.8 | 72.03 | 6.88 | 19.05 | 0.00 | 0.37 | 2.68 |
| 948 | High | CuZnO Ref B | Mn | 1000 | 178.5 | 72.10 | 6.79 | 19.03 | 0.00 | 0.42 | 2.81 |
| 949 | High | CuZnO Ref B | Mn | 1000 | 178.5 | 72.15 | 6.73 | 19.05 | 0.00 | 0.40 | 3.22 |
| 950 | High | CuZnO Ref A | Mn | 1000 | 178.5 | 72.17 | 7.04 | 18.84 | 0.00 | 0.28 | 3.36 |
| 951 | High | CuZnO Ref A | Mn | 1000 | 178.3 | 72.00 | 7.05 | 18.99 | 0.00 | 0.28 | 2.69 |

TABLE 6

Activity of Unmodified Copper Chromite Catalyst for Methanol Production

| Comp. Ex. No. | $CO_2$ Level | Cat | Temp (° C.) | $H_2$ wt % | CO wt % | $CO_2$ wt % | DME wt % | MeOH wt % | CO & $CO_2$ conv % |
|---|---|---|---|---|---|---|---|---|---|
| 952 | Low | CuCrOx | 293.7 | 62.33 | 26.26 | 3.24 | 0.22 | 6.11 | 16.94 |
| 953 | Low | CuCrOx | 316.8 | 62.97 | 25.98 | 3.68 | 0.51 | 5.02 | 16.50 |
| 954 | Low | CuCrOx | 274.8 | 63.57 | 26.98 | 2.96 | 0.09 | 4.62 | 13.07 |
| 955 | Low | CuCrOx | 240.1 | 65.93 | 28.15 | 2.72 | 0.01 | 1.50 | 5.37 |
| 956 | Low | CuCrOx | 239.6 | 65.92 | 28.22 | 2.71 | 0.01 | 1.45 | 5.14 |
| 957 | Low | CuCrOx | 229.8 | 66.17 | 28.28 | 2.71 | 0.00 | 1.16 | 4.32 |
| 958 | Low | CuCrOx | 230.1 | 66.17 | 28.32 | 2.71 | 0.00 | 1.11 | 4.17 |
| 959 | Low | CuCrOx | 199.8 | 66.74 | 28.54 | 2.69 | 0.00 | 0.38 | 2.31 |
| 960 | Low | CuCrOx | 200.1 | 66.73 | 28.57 | 2.69 | 0.00 | 0.36 | 2.06 |
| 961 | Low | CuCrOx | 180.3 | 66.55 | 28.96 | 2.69 | 0.00 | 0.17 | −0.05 |
| 962 | Low | CuCrOx | 179.7 | 66.87 | 28.64 | 2.68 | 0.00 | 0.16 | 1.56 |
| 963 | High | CuCrOx | 238.4 | 71.75 | 7.31 | 18.40 | 0.00 | 0.85 | 4.81 |
| 964 | High | CuCrOx | 238.4 | 71.72 | 7.28 | 18.47 | 0.00 | 0.83 | 4.85 |
| 965 | High | CuCrOx | 228.5 | 71.79 | 7.24 | 18.66 | 0.00 | 0.64 | 3.30 |
| 966 | High | CuCrOx | 228.3 | 71.78 | 7.22 | 18.70 | 0.00 | 0.61 | 3.26 |
| 967 | High | CuCrOx | 198.6 | 71.90 | 7.05 | 19.17 | 0.00 | 0.23 | 0.53 |
| 968 | High | CuCrOx | 198.4 | 71.97 | 7.09 | 19.08 | 0.00 | 0.22 | 0.60 |
| 969 | High | CuCrOx | 178.9 | 72.29 | 6.85 | 19.10 | 0.00 | 0.11 | 1.60 |
| 970 | High | CuCrOx | 179.1 | 72.13 | 6.93 | 19.19 | 0.00 | 0.11 | 0.51 |

TABLE 7

Activity of Non-La Promoted 1% Palladium on Copper Chromite Catalysts for Methanol Production

| Comp. Ex. No. | $CO_2$ Level | Promoter | Promoter (ppm) | Temp (° C.) | $H_2$ wt % | CO wt % | $CO_2$ wt % | DME wt % | MeOH wt % | CO & $CO_2$ conv % |
|---|---|---|---|---|---|---|---|---|---|---|
| 971 | Low | Ba | 1000 | 239.9 | 66.33 | 29.06 | 2.66 | 0.00 | 0.30 | 0.22 |
| 972 | Low | Ba | 1000 | 239.9 | 66.11 | 29.26 | 2.67 | 0.00 | 0.30 | 0.48 |
| 973 | Low | None | | 238.7 | 67.27 | 28.53 | 2.56 | 0.01 | 0.00 | 1.45 |
| 974 | Low | None | | 238.5 | 67.24 | 28.61 | 2.51 | 0.00 | 0.00 | 1.38 |

TABLE 7-continued

Activity of Non-La Promoted 1% Palladium on Copper Chromite Catalysts for Methanol Production

| Comp. Ex. No. | $CO_2$ Level | Promoter | Promoter (ppm) | Temp (° C.) | $H_2$ wt % | CO wt % | $CO_2$ wt % | DME wt % | MeOH wt % | CO & $CO_2$ conv % |
|---|---|---|---|---|---|---|---|---|---|---|
| 975 | Low | Ca | 5000 | 238.4 | 66.68 | 29.10 | 2.43 | 0.00 | 0.13 | 1.49 |
| 976 | Low | Ca | 5000 | 238.4 | 66.67 | 29.11 | 2.43 | 0.00 | 0.13 | 1.36 |
| 977 | Low | Ba | 1000 | 230.1 | 66.15 | 29.31 | 2.67 | 0.00 | 0.21 | −0.10 |
| 978 | Low | Ba | 1000 | 229.9 | 66.23 | 29.25 | 2.66 | 0.00 | 0.21 | −0.09 |
| 979 | Low | Ca | 5000 | 228.5 | 66.75 | 29.07 | 2.44 | 0.00 | 0.09 | 1.46 |
| 980 | Low | Ca | 5000 | 228.3 | 66.77 | 29.04 | 2.44 | 0.00 | 0.10 | 1.39 |
| 981 | Low | None | | 228.8 | 67.20 | 28.65 | 2.51 | 0.01 | 0.00 | 1.16 |
| 982 | Low | None | | 228.3 | 67.26 | 28.59 | 2.52 | 0.00 | 0.00 | 1.35 |
| 983 | Low | Ca | 1000 | 200.1 | 66.96 | 28.62 | 2.64 | 0.00 | 0.14 | 0.96 |
| 984 | Low | Ca | 5000 | 200.1 | 66.79 | 28.73 | 2.70 | 0.00 | 0.14 | 0.78 |
| 985 | Low | Ca | 5000 | 200.0 | 66.80 | 28.72 | 2.70 | 0.00 | 0.14 | 0.86 |
| 986 | Low | Ca | 1000 | 199.8 | 67.02 | 28.55 | 2.65 | 0.00 | 0.15 | 1.21 |
| 987 | Low | Ba | 1000 | 199.8 | 66.27 | 29.35 | 2.67 | 0.00 | 0.06 | −0.57 |
| 988 | Low | Ba | 1000 | 199.8 | 66.29 | 29.32 | 2.68 | 0.00 | 0.06 | −0.40 |
| 989 | Low | Ca | 5000 | 198.6 | 66.80 | 29.08 | 2.46 | 0.00 | 0.03 | 0.70 |
| 990 | Low | Ca | 5000 | 198.4 | 66.66 | 29.20 | 2.46 | 0.00 | 0.03 | 1.01 |
| 991 | Low | None | | 198.7 | 67.17 | 28.67 | 2.52 | 0.00 | 0.00 | 1.30 |
| 992 | Low | None | | 198.6 | 67.21 | 28.64 | 2.52 | 0.00 | 0.00 | 1.18 |
| 993 | Low | Ba | 1000 | 180.2 | 66.33 | 29.32 | 2.68 | 0.00 | 0.03 | −0.84 |
| 994 | Low | Ca | 1000 | 180.0 | 67.12 | 28.53 | 2.65 | 0.00 | 0.06 | 1.45 |
| 995 | Low | Ca | 5000 | 180.0 | 66.81 | 28.80 | 2.70 | 0.00 | 0.06 | 0.34 |
| 996 | Low | Ba | 1000 | 180.0 | 66.35 | 29.29 | 2.69 | 0.00 | 0.03 | −0.59 |
| 997 | Low | Ca | 5000 | 179.9 | 66.82 | 28.80 | 2.70 | 0.00 | 0.06 | −0.26 |
| 998 | Low | Ca | 5000 | 178.5 | 66.63 | 29.23 | 2.47 | 0.00 | 0.01 | 0.85 |
| 999 | Low | Ca | 5000 | 178.5 | 66.63 | 29.23 | 2.47 | 0.00 | 0.01 | 0.92 |
| 1000 | Low | Ca | 1000 | 179.7 | 67.01 | 28.64 | 2.64 | 0.00 | 0.07 | 1.21 |
| 1001 | Low | None | | 178.8 | 67.11 | 28.73 | 2.53 | 0.00 | 0.00 | 1.34 |
| 1002 | Low | None | | 178.8 | 67.10 | 28.66 | 2.60 | 0.00 | 0.00 | 1.09 |
| 1003 | High | Mg | 1000 | 240.1 | 72.05 | 7.02 | 18.72 | 0.00 | 0.54 | 3.75 |
| 1004 | High | Na | 5000 | 239.9 | 72.17 | 6.67 | 18.63 | 0.00 | 0.86 | 5.44 |
| 1005 | High | Na | 5000 | 239.9 | 72.26 | 6.69 | 18.53 | 0.00 | 0.84 | 5.87 |
| 1006 | High | | | 239.9 | 72.01 | 6.84 | 18.70 | 0.00 | 0.77 | 4.33 |
| 1007 | High | | | 239.7 | 72.08 | 6.78 | 18.67 | 0.00 | 0.79 | 5.01 |
| 1008 | High | | | 239.7 | 71.88 | 6.76 | 18.91 | 0.00 | 0.78 | 3.54 |
| 1009 | High | Mg | 1000 | 239.7 | 72.14 | 7.04 | 18.61 | 0.00 | 0.54 | 4.10 |
| 1010 | High | Na | 1000 | 238.8 | 71.94 | 6.85 | 18.86 | 0.00 | 0.67 | 3.72 |
| 1011 | High | Mn | 1000 | 238.7 | 71.84 | 7.16 | 18.49 | 0.00 | 0.83 | 4.16 |
| 1012 | High | Mg | 5000 | 238.5 | 71.94 | 7.23 | 18.44 | 0.00 | 0.70 | 3.99 |
| 1013 | High | Mg | 5000 | 238.5 | 71.99 | 7.18 | 18.46 | 0.00 | 0.69 | 4.29 |
| 1014 | High | Na | 1000 | 238.5 | 72.13 | 7.00 | 18.53 | 0.00 | 0.68 | 4.37 |
| 1015 | High | K | 1000 | 238.5 | 71.26 | 7.24 | 19.36 | 0.00 | 0.50 | −0.92 |
| 1016 | High | Ca | 5000 | 238.5 | 71.80 | 7.46 | 18.83 | 0.00 | 0.25 | 1.01 |
| 1017 | High | Ca | 5000 | 238.5 | 71.96 | 7.39 | 18.75 | 0.00 | 0.24 | 1.83 |
| 1018 | High | Mn | 1000 | 238.4 | 71.88 | 7.18 | 18.43 | 0.00 | 0.83 | 4.40 |
| 1019 | High | Ca | 1000 | 238.4 | 71.42 | 7.25 | 19.04 | 0.00 | 0.62 | 1.52 |
| 1020 | High | Ca | 1000 | 238.4 | 71.43 | 7.25 | 19.03 | 0.00 | 0.62 | 1.27 |
| 1021 | High | Mn | 5000 | 238.4 | 71.62 | 6.99 | 19.11 | 0.00 | 0.61 | 2.10 |
| 1022 | High | Mn | 5000 | 238.4 | 71.41 | 6.98 | 19.33 | 0.00 | 0.61 | 1.38 |
| 1023 | High | K | 1000 | 238.4 | 71.01 | 7.36 | 19.49 | 0.00 | 0.50 | −2.34 |
| 1024 | High | Ba | 1000 | 238.4 | 72.10 | 7.20 | 18.70 | 0.00 | 0.31 | 3.87 |
| 1025 | High | Ba | 1000 | 238.4 | 71.77 | 7.23 | 19.02 | 0.00 | 0.31 | 1.66 |
| 1026 | High | K | 5000 | 238.4 | 71.94 | 7.84 | 18.44 | 0.00 | 0.09 | 2.04 |
| 1027 | High | K | 5000 | 238.4 | 71.75 | 7.63 | 18.86 | 0.00 | 0.09 | 0.35 |
| 1028 | High | | | 230.1 | 72.22 | 6.82 | 18.73 | 0.00 | 0.56 | 3.88 |
| 1029 | High | Mg | 1000 | 230.1 | 72.25 | 6.90 | 18.79 | 0.00 | 0.40 | 3.54 |
| 1030 | High | Na | 5000 | 229.9 | 72.32 | 6.72 | 18.70 | 0.00 | 0.59 | 4.37 |
| 1031 | High | Na | 5000 | 229.9 | 72.29 | 6.73 | 18.75 | 0.00 | 0.57 | 3.87 |
| 1032 | High | Mg | 1000 | 229.9 | 72.10 | 6.89 | 18.96 | 0.00 | 0.38 | 2.70 |
| 1033 | High | | | 229.9 | 72.22 | 6.77 | 18.77 | 0.00 | 0.58 | 3.82 |
| 1034 | High | | | 229.9 | 72.16 | 6.82 | 18.81 | 0.00 | 0.55 | 3.46 |
| 1035 | High | Na | 5000 | 229.7 | 72.39 | 6.70 | 18.64 | 0.00 | 0.61 | 4.67 |
| 1036 | High | Mg | 1000 | 229.7 | 72.21 | 6.97 | 18.77 | 0.00 | 0.39 | 3.29 |
| 1037 | High | Na | 1000 | 228.8 | 72.35 | 6.75 | 18.74 | 0.00 | 0.48 | 4.54 |
| 1038 | High | Mn | 1000 | 228.6 | 72.11 | 7.05 | 18.59 | 0.00 | 0.58 | 3.61 |
| 1039 | High | Ca | 1000 | 228.6 | 71.48 | 7.19 | 19.23 | 0.00 | 0.44 | 0.06 |
| 1040 | High | Ca | 1000 | 228.6 | 71.37 | 7.23 | 19.31 | 0.00 | 0.44 | −0.60 |
| 1041 | High | Mn | 1000 | 228.5 | 72.14 | 6.93 | 18.66 | 0.00 | 0.60 | 3.98 |
| 1042 | High | Mg | 5000 | 228.5 | 72.04 | 7.14 | 18.65 | 0.00 | 0.50 | 2.89 |
| 1043 | High | K | 1000 | 228.5 | 71.13 | 7.17 | 19.71 | 0.00 | 0.35 | −2.80 |
| 1044 | High | Ca | 5000 | 228.5 | 71.98 | 7.29 | 18.88 | 0.00 | 0.18 | 1.62 |
| 1045 | High | Ca | 5000 | 228.5 | 71.98 | 7.25 | 18.94 | 0.00 | 0.18 | 1.28 |
| 1046 | High | K | 5000 | 228.5 | 71.72 | 7.53 | 19.03 | 0.00 | 0.06 | −0.26 |
| 1047 | High | K | 5000 | 228.5 | 71.79 | 7.56 | 18.92 | 0.00 | 0.06 | 0.31 |
| 1048 | High | Mg | 5000 | 228.3 | 71.95 | 7.11 | 18.79 | 0.00 | 0.49 | 2.41 |

TABLE 7-continued

Activity of Non-La Promoted 1% Palladium on Copper Chromite Catalysts for Methanol Production

| Comp. Ex. No. | CO$_2$ Level | Promoter | Promoter (ppm) | Temp (° C.) | H$_2$ wt % | CO wt % | CO$_2$ wt % | DME wt % | MeOH wt % | CO & CO$_2$ conv % |
|---|---|---|---|---|---|---|---|---|---|---|
| 1049 | High | Na | 1000 | 228.3 | 72.18 | 6.82 | 18.87 | 0.00 | 0.46 | 3.58 |
| 1050 | High | Mn | 5000 | 228.3 | 71.50 | 6.95 | 19.45 | 0.00 | 0.44 | 0.16 |
| 1051 | High | Mn | 5000 | 228.3 | 71.54 | 6.99 | 19.38 | 0.00 | 0.43 | 0.99 |
| 1052 | High | K | 1000 | 228.3 | 71.17 | 7.16 | 19.68 | 0.00 | 0.36 | −2.56 |
| 1053 | High | Ba | 1000 | 228.3 | 71.91 | 7.08 | 19.10 | 0.00 | 0.23 | 2.36 |
| 1054 | High | Ba | 1000 | 228.3 | 71.96 | 7.09 | 19.05 | 0.00 | 0.22 | 2.06 |
| 1055 | High | None | | 200.1 | 72.65 | 6.51 | 19.00 | 0.00 | 0.19 | 2.94 |
| 1056 | High | Mg | 1000 | 200.1 | 72.32 | 6.80 | 19.11 | 0.00 | 0.13 | 1.44 |
| 1057 | High | None | | 200.0 | 72.57 | 6.49 | 19.11 | 0.00 | 0.19 | 2.44 |
| 1058 | High | None | | 200.0 | 72.51 | 6.59 | 19.08 | 0.00 | 0.19 | 2.17 |
| 1059 | High | Na | 5000 | 200.0 | 72.64 | 6.62 | 18.93 | 0.00 | 0.18 | 2.32 |
| 1060 | High | Na | 5000 | 199.8 | 72.71 | 6.49 | 18.98 | 0.00 | 0.18 | 2.61 |
| 1061 | High | Na | 5000 | 199.8 | 72.57 | 6.52 | 19.10 | 0.00 | 0.17 | 1.93 |
| 1062 | High | Mg | 1000 | 199.8 | 72.44 | 6.74 | 19.04 | 0.00 | 0.14 | 2.11 |
| 1063 | High | Mg | 1000 | 199.5 | 72.35 | 6.78 | 19.09 | 0.00 | 0.13 | 1.51 |
| 1064 | High | Mn | 1000 | 198.7 | 72.34 | 6.80 | 19.02 | 0.00 | 0.19 | 1.36 |
| 1065 | High | Mg | 5000 | 198.7 | 72.07 | 6.91 | 19.22 | 0.00 | 0.17 | 0.08 |
| 1066 | High | Na | 1000 | 198.7 | 72.26 | 6.71 | 19.24 | 0.00 | 0.15 | 1.30 |
| 1067 | High | Mn | 5000 | 198.7 | 71.63 | 6.87 | 19.70 | 0.00 | 0.15 | −1.02 |
| 1068 | High | Ca | 1000 | 198.7 | 71.43 | 7.05 | 19.74 | 0.00 | 0.15 | −2.65 |
| 1069 | High | K | 1000 | 198.7 | 71.19 | 6.97 | 20.10 | 0.00 | 0.12 | −4.53 |
| 1070 | High | Ca | 5000 | 198.7 | 71.97 | 7.16 | 19.16 | 0.00 | 0.06 | 0.35 |
| 1071 | High | Mn | 1000 | 198.6 | 72.40 | 6.74 | 19.01 | 0.00 | 0.20 | 1.80 |
| 1072 | High | Mg | 5000 | 198.6 | 72.21 | 6.85 | 19.14 | 0.00 | 0.16 | 0.64 |
| 1073 | High | Ca | 1000 | 198.6 | 71.69 | 6.97 | 19.55 | 0.00 | 0.15 | −1.27 |
| 1074 | High | Mn | 5000 | 198.6 | 71.64 | 6.74 | 19.83 | 0.00 | 0.14 | −0.96 |
| 1075 | High | K | 1000 | 198.6 | 71.15 | 6.93 | 20.18 | 0.00 | 0.12 | −4.76 |
| 1076 | High | Ba | 1000 | 198.6 | 71.95 | 7.00 | 19.30 | 0.00 | 0.08 | 1.12 |
| 1077 | High | Ba | 1000 | 198.6 | 71.99 | 6.91 | 19.37 | 0.00 | 0.08 | 0.96 |
| 1078 | High | Ca | 5000 | 198.6 | 71.96 | 7.11 | 19.22 | 0.00 | 0.06 | −0.14 |
| 1079 | High | K | 5000 | 198.6 | 72.08 | 7.32 | 18.90 | 0.00 | 0.02 | 1.82 |
| 1080 | High | K | 5000 | 198.6 | 71.92 | 7.27 | 19.12 | 0.00 | 0.02 | 0.67 |
| 1081 | High | Na | 1000 | 198.4 | 72.36 | 6.60 | 19.23 | 0.00 | 0.16 | 1.78 |
| 1082 | High | None | | 180.2 | 72.60 | 6.36 | 19.31 | 0.00 | 0.09 | 1.87 |
| 1083 | High | None | | 180.0 | 72.49 | 6.58 | 19.19 | 0.00 | 0.10 | 1.21 |
| 1084 | High | None | | 180.0 | 72.56 | 6.45 | 19.28 | 0.00 | 0.08 | 1.43 |
| 1085 | High | Mg | 1000 | 180.2 | 72.31 | 6.65 | 19.34 | 0.00 | 0.06 | 0.70 |
| 1086 | High | Na | 5000 | 180.0 | 72.69 | 6.45 | 19.15 | 0.00 | 0.07 | 1.73 |
| 1087 | High | Na | 5000 | 179.9 | 72.59 | 6.33 | 19.37 | 0.00 | 0.08 | 1.23 |
| 1088 | High | Mg | 1000 | 179.9 | 72.34 | 6.75 | 19.21 | 0.00 | 0.06 | 1.08 |
| 1089 | High | Na | 5000 | 179.7 | 72.65 | 6.39 | 19.25 | 0.00 | 0.09 | 1.30 |
| 1090 | High | Mg | 1000 | 179.7 | 72.46 | 6.66 | 19.17 | 0.00 | 0.06 | 1.58 |
| 1091 | High | Mn | 1000 | 179.2 | 72.80 | 6.29 | 19.16 | 0.00 | 0.10 | 3.21 |
| 1092 | High | Mn | 5000 | 179.2 | 71.85 | 6.74 | 19.70 | 0.00 | 0.07 | −1.11 |
| 1093 | High | Ca | 1000 | 179.2 | 71.70 | 6.87 | 19.73 | 0.00 | 0.07 | −2.28 |
| 1094 | High | Ca | 5000 | 179.2 | 72.37 | 6.80 | 19.14 | 0.00 | 0.03 | 2.04 |
| 1095 | High | Mn | 1000 | 179.1 | 72.56 | 6.56 | 19.16 | 0.00 | 0.09 | 1.57 |
| 1096 | High | Mg | 5000 | 179.1 | 72.41 | 6.68 | 19.19 | 0.00 | 0.08 | 1.11 |
| 1097 | High | K | 1000 | 179.1 | 71.43 | 6.75 | 20.15 | 0.00 | 0.06 | −4.04 |
| 1098 | High | K | 1000 | 179.1 | 71.25 | 6.83 | 20.25 | 0.00 | 0.06 | −4.95 |
| 1099 | High | K | 5000 | 179.1 | 72.15 | 7.11 | 19.06 | 0.00 | 0.01 | 1.94 |
| 1100 | High | K | 5000 | 179.1 | 71.93 | 7.27 | 19.13 | 0.00 | 0.01 | 0.27 |
| 1101 | High | Mg | 5000 | 178.9 | 72.27 | 6.77 | 19.25 | 0.00 | 0.08 | 0.36 |
| 1102 | High | Mn | 5000 | 178.9 | 71.69 | 6.76 | 19.84 | 0.00 | 0.07 | −1.78 |
| 1103 | High | Ca | 5000 | 178.9 | 72.09 | 7.10 | 19.12 | 0.00 | 0.03 | 0.51 |
| 1104 | High | Na | 1000 | 178.8 | 72.45 | 6.47 | 19.37 | 0.00 | 0.07 | 1.28 |
| 1105 | High | Na | 1000 | 178.6 | 72.49 | 6.57 | 19.23 | 0.00 | 0.08 | 1.33 |
| 1106 | High | Ba | 1000 | 178.5 | 72.11 | 6.86 | 19.34 | 0.00 | 0.04 | 0.99 |
| 1107 | High | Ba | 1000 | 178.5 | 72.07 | 6.92 | 19.31 | 0.00 | 0.03 | 1.11 |
| 1108 | High | Ca | 1000 | 177.7 | 71.91 | 6.59 | 19.79 | 0.00 | 0.07 | −0.94 |

TABLE 8

Activity of Promoted Copper Chromite Catalysts without Pd for Methanol Production

| Comp. Ex. No. | CO$_2$ | Prom | Prom ppm | Temp (° C.) | H$_2$ wt % | CO wt % | CO$_2$ wt % | DME wt % | MeOH wt % | CO & CO$_2$ conv % |
|---|---|---|---|---|---|---|---|---|---|---|
| 1109 | Low | Ga | 5000 | 294.1 | 63.22 | 26.79 | 2.99 | 0.06 | 5.14 | 14.34 |
| 1110 | Low | Ga | 5000 | 316.9 | 63.12 | 26.52 | 3.27 | 0.18 | 5.10 | 15.09 |
| 1111 | Low | Ga | 5000 | 275.1 | 64.32 | 27.81 | 2.80 | 0.02 | 3.32 | 8.55 |

TABLE 8-continued

Activity of Promoted Copper Chromite Catalysts without Pd for Methanol Production

| Comp. Ex. No. | CO$_2$ | Prom | Prom ppm | Temp (° C.) | H$_2$ wt % | CO wt % | CO$_2$ wt % | DME wt % | MeOH wt % | CO & CO$_2$ conv % |
|---|---|---|---|---|---|---|---|---|---|---|
| 1112 | Low | Ga | 5000 | 239.7 | 66.39 | 28.28 | 2.69 | 0.00 | 0.97 | 4.13 |
| 1113 | Low | Ga | 5000 | 239.7 | 66.40 | 28.28 | 2.69 | 0.00 | 0.96 | 3.95 |
| 1114 | Low | Li | 1000 | 240.1 | 66.69 | 28.20 | 2.68 | 0.00 | 0.77 | 3.80 |
| 1115 | Low | Li | 1000 | 240.1 | 66.77 | 28.15 | 2.68 | 0.00 | 0.74 | 3.56 |
| 1116 | Low | Ga | 5000 | 229.5 | 66.58 | 28.35 | 2.68 | 0.00 | 0.72 | 3.29 |
| 1117 | Low | Ga | 5000 | 229.8 | 66.64 | 28.32 | 2.69 | 0.00 | 0.69 | 3.35 |
| 1118 | Low | Sr | 1000 | 239.9 | 66.59 | 28.44 | 2.67 | 0.00 | 0.65 | 2.61 |
| 1119 | Low | La | 1000 | 238.4 | 66.40 | 28.74 | 2.57 | 0.00 | 0.63 | 2.01 |
| 1120 | Low | Sr | 1000 | 239.6 | 66.71 | 28.33 | 2.67 | 0.00 | 0.63 | 3.44 |
| 1121 | Low | La | 1000 | 238.5 | 66.09 | 29.08 | 2.57 | 0.00 | 0.61 | 0.96 |
| 1122 | Low | Ba | 1000 | 240.0 | 66.92 | 28.34 | 2.48 | 0.00 | 0.60 | 3.70 |
| 1123 | Low | Ba | 1000 | 239.7 | 66.89 | 28.39 | 2.48 | 0.00 | 0.59 | 3.54 |
| 1124 | Low | Na | 1000 | 238.7 | 66.39 | 28.74 | 2.65 | 0.00 | 0.57 | 1.33 |
| 1125 | Low | Na | 1000 | 238.5 | 66.39 | 28.76 | 2.65 | 0.00 | 0.55 | 1.25 |
| 1126 | Low | Li | 1000 | 229.9 | 66.75 | 28.42 | 2.67 | 0.00 | 0.52 | 2.21 |
| 1127 | Low | K | 1000 | 238.5 | 66.40 | 28.78 | 2.66 | 0.00 | 0.52 | 1.12 |
| 1128 | Low | K | 1000 | 238.5 | 66.31 | 28.88 | 2.66 | 0.00 | 0.50 | 0.60 |
| 1129 | Low | Li | 1000 | 229.9 | 66.85 | 28.36 | 2.67 | 0.00 | 0.49 | 2.32 |
| 1130 | Low | Sr | 1000 | 229.9 | 66.84 | 28.40 | 2.67 | 0.00 | 0.43 | 2.29 |
| 1131 | Low | La | 1000 | 228.3 | 67.64 | 27.84 | 2.43 | 0.00 | 0.42 | 6.00 |
| 1132 | Low | Sr | 1000 | 229.8 | 66.78 | 28.50 | 2.67 | 0.00 | 0.41 | 1.82 |
| 1133 | Low | La | 1000 | 228.2 | 66.32 | 29.04 | 2.59 | 0.00 | 0.41 | 0.39 |
| 1134 | Low | Ba | 1000 | 229.9 | 66.94 | 28.53 | 2.48 | 0.00 | 0.40 | 2.64 |
| 1135 | Low | Na | 1000 | 228.8 | 66.72 | 28.62 | 2.64 | 0.00 | 0.38 | 1.16 |
| 1136 | Low | Ba | 1000 | 230.2 | 67.09 | 28.41 | 2.48 | 0.00 | 0.38 | 3.15 |
| 1137 | Low | Rb | 1000 | 238.5 | 66.92 | 28.38 | 2.68 | 0.00 | 0.37 | 2.39 |
| 1138 | Low | Rb | 1000 | 238.7 | 66.89 | 28.42 | 2.68 | 0.00 | 0.36 | 2.44 |
| 1139 | Low | Na | 1000 | 228.3 | 66.71 | 28.64 | 2.65 | 0.00 | 0.36 | 1.50 |
| 1140 | Low | K | 1000 | 228.6 | 66.62 | 28.75 | 2.65 | 0.00 | 0.34 | 1.09 |
| 1141 | Low | K | 1000 | 228.3 | 66.80 | 28.58 | 2.65 | 0.00 | 0.32 | 1.85 |
| 1142 | Low | Rb | 1000 | 228.5 | 66.86 | 28.57 | 2.68 | 0.00 | 0.25 | 1.16 |
| 1143 | Low | Rb | 1000 | 228.3 | 66.99 | 28.45 | 2.68 | 0.00 | 0.24 | 1.74 |
| 1144 | Low | Ga | 5000 | 200.1 | 66.98 | 28.47 | 2.68 | 0.00 | 0.23 | 2.05 |
| 1145 | Low | Ga | 5000 | 199.6 | 67.01 | 28.44 | 2.68 | 0.00 | 0.22 | 2.26 |
| 1146 | Low | Li | 1000 | 200.1 | 67.02 | 28.53 | 2.67 | 0.00 | 0.14 | 1.17 |
| 1147 | Low | Li | 1000 | 200.3 | 67.09 | 28.47 | 2.67 | 0.00 | 0.13 | 1.33 |
| 1148 | Low | Sr | 1000 | 200.0 | 66.96 | 28.61 | 2.67 | 0.00 | 0.12 | 1.03 |
| 1149 | Low | La | 1000 | 198.4 | 67.38 | 28.36 | 2.48 | 0.00 | 0.12 | 3.61 |
| 1150 | Low | Ba | 1000 | 199.8 | 67.11 | 28.63 | 2.49 | 0.00 | 0.12 | 2.11 |
| 1151 | Low | Na | 1000 | 198.6 | 66.96 | 28.64 | 2.64 | 0.00 | 0.11 | 1.33 |
| 1152 | Low | Sr | 1000 | 200.1 | 67.01 | 28.56 | 2.68 | 0.00 | 0.11 | 1.16 |
| 1153 | Low | La | 1000 | 198.6 | 67.32 | 28.42 | 2.50 | 0.00 | 0.11 | 3.11 |
| 1154 | Low | Ba | 1000 | 200.1 | 67.18 | 28.57 | 2.49 | 0.00 | 0.10 | 2.96 |
| 1155 | Low | Na | 1000 | 198.9 | 66.96 | 28.66 | 2.65 | 0.00 | 0.10 | 0.95 |
| 1156 | Low | K | 1000 | 198.6 | 66.92 | 28.70 | 2.65 | 0.00 | 0.10 | 1.00 |
| 1157 | Low | Ga | 5000 | 180.3 | 66.87 | 28.70 | 2.69 | 0.00 | 0.10 | 0.93 |
| 1158 | Low | Ga | 5000 | 179.6 | 67.09 | 28.49 | 2.68 | 0.00 | 0.09 | 1.80 |
| 1159 | Low | K | 1000 | 198.6 | 67.09 | 28.52 | 2.66 | 0.00 | 0.09 | 1.52 |
| 1160 | Low | Rb | 1000 | 198.6 | 66.98 | 28.63 | 2.68 | 0.00 | 0.08 | 0.65 |
| 1161 | Low | Li | 1000 | 180.0 | 67.15 | 28.47 | 2.67 | 0.00 | 0.07 | 1.34 |
| 1162 | Low | Rb | 1000 | 198.7 | 67.04 | 28.57 | 2.69 | 0.00 | 0.07 | 0.87 |
| 1163 | Low | Ba | 1000 | 180.0 | 67.30 | 28.49 | 2.50 | 0.00 | 0.06 | 2.41 |
| 1164 | Low | Sr | 1000 | 180.0 | 67.03 | 28.59 | 2.68 | 0.00 | 0.06 | 0.91 |
| 1165 | Low | La | 1000 | 178.5 | 68.16 | 27.68 | 2.43 | 0.00 | 0.06 | 6.11 |
| 1166 | Low | Li | 1000 | 180.0 | 67.08 | 28.56 | 2.67 | 0.00 | 0.06 | 0.75 |
| 1167 | Low | Na | 1000 | 178.8 | 67.12 | 28.54 | 2.65 | 0.00 | 0.06 | 1.42 |
| 1168 | Low | Sr | 1000 | 180.0 | 67.09 | 28.53 | 2.69 | 0.00 | 0.05 | 1.15 |
| 1169 | Low | La | 1000 | 178.5 | 66.71 | 29.03 | 2.57 | 0.00 | 0.05 | 0.08 |
| 1170 | Low | Ba | 1000 | 179.9 | 67.19 | 28.62 | 2.50 | 0.00 | 0.05 | 2.04 |
| 1171 | Low | Na | 1000 | 178.8 | 67.00 | 28.67 | 2.65 | 0.00 | 0.05 | 0.65 |
| 1172 | Low | K | 1000 | 179.2 | 67.16 | 28.50 | 2.66 | 0.00 | 0.05 | 1.29 |
| 1173 | Low | K | 1000 | 178.9 | 67.14 | 28.53 | 2.66 | 0.00 | 0.04 | 1.32 |
| 1174 | Low | Rb | 1000 | 179.2 | 66.99 | 28.65 | 2.69 | 0.00 | 0.04 | 0.29 |
| 1175 | Low | Rb | 1000 | 179.2 | 67.07 | 28.58 | 2.69 | 0.00 | 0.03 | 0.70 |
| 1176 | High | Rb | 1000 | 239.9 | 72.15 | 4.79 | 19.15 | 0.00 | 2.19 | 12.39 |
| 1177 | High | Rb | 1000 | 240.0 | 71.98 | 5.03 | 19.13 | 0.00 | 2.16 | 10.99 |
| 1178 | High | Rb | 1000 | 239.9 | 72.08 | 5.08 | 19.02 | 0.00 | 2.12 | 11.32 |
| 1179 | High | Rb | 1000 | 228.3 | 72.54 | 5.30 | 19.11 | 0.00 | 1.37 | 8.64 |
| 1180 | High | Rb | 1000 | 228.3 | 72.66 | 5.29 | 19.03 | 0.00 | 1.34 | 9.20 |
| 1181 | High | Rb | 1000 | 228.3 | 72.53 | 5.38 | 19.12 | 0.00 | 1.29 | 8.17 |
| 1182 | High | Sr | 1000 | 238.3 | 71.99 | 6.99 | 18.57 | 0.00 | 0.78 | 4.54 |
| 1183 | High | Sr | 1000 | 238.4 | 72.06 | 7.12 | 18.37 | 0.00 | 0.77 | 4.95 |
| 1184 | High | Ba | 1000 | 239.9 | 72.11 | 6.81 | 18.68 | 0.00 | 0.72 | 4.76 |
| 1185 | High | Ba | 1000 | 239.9 | 72.02 | 6.82 | 18.78 | 0.00 | 0.71 | 4.21 |

TABLE 8-continued

Activity of Promoted Copper Chromite Catalysts without Pd for Methanol Production

| Comp. Ex. No. | $CO_2$ | Prom | Prom ppm | Temp (° C.) | $H_2$ wt % | CO wt % | $CO_2$ wt % | DME wt % | MeOH wt % | CO & $CO_2$ conv % |
|---|---|---|---|---|---|---|---|---|---|---|
| 1186 | High | Ba | 1000 | 240.0 | 72.15 | 6.81 | 18.67 | 0.00 | 0.70 | 4.66 |
| 1187 | High | Na | 1000 | 238.5 | 71.76 | 6.86 | 19.05 | 0.00 | 0.66 | 2.89 |
| 1188 | High | Na | 1000 | 238.3 | 71.73 | 6.84 | 19.10 | 0.00 | 0.66 | 2.67 |
| 1189 | High | Li | 1000 | 238.4 | 71.96 | 7.23 | 18.48 | 0.00 | 0.65 | 4.30 |
| 1190 | High | Li | 1000 | 238.3 | 72.04 | 7.22 | 18.42 | 0.00 | 0.64 | 4.53 |
| 1191 | High | Ga | 5000 | 238.4 | 71.95 | 6.98 | 18.75 | 0.00 | 0.64 | 4.11 |
| 1192 | High | Ga | 5000 | 238.4 | 71.86 | 7.17 | 18.66 | 0.00 | 0.63 | 3.81 |
| 1193 | High | K | 1000 | 238.7 | 72.29 | 6.78 | 18.70 | 0.00 | 0.56 | 4.24 |
| 1194 | High | Sr | 1000 | 228.5 | 72.06 | 6.98 | 18.74 | 0.00 | 0.55 | 3.20 |
| 1195 | High | K | 1000 | 238.4 | 72.13 | 6.88 | 18.77 | 0.00 | 0.55 | 3.64 |
| 1196 | High | Sr | 1000 | 228.5 | 72.10 | 7.00 | 18.69 | 0.00 | 0.55 | 3.53 |
| 1197 | High | Ba | 1000 | 229.9 | 72.31 | 6.77 | 18.74 | 0.00 | 0.52 | 4.15 |
| 1198 | High | La | 1000 | 240.0 | 71.98 | 6.93 | 18.90 | 0.00 | 0.51 | 2.82 |
| 1199 | High | Ba | 1000 | 229.7 | 72.18 | 6.82 | 18.83 | 0.00 | 0.51 | 3.45 |
| 1200 | High | Ba | 1000 | 230.1 | 72.26 | 6.71 | 18.86 | 0.00 | 0.50 | 3.71 |
| 1201 | High | La | 1000 | 239.7 | 72.05 | 6.81 | 18.97 | 0.00 | 0.50 | 2.98 |
| 1202 | High | La | 1000 | 240.0 | 72.02 | 6.90 | 18.92 | 0.00 | 0.49 | 2.76 |
| 1203 | High | Na | 1000 | 228.5 | 72.01 | 6.72 | 19.14 | 0.00 | 0.48 | 2.64 |
| 1204 | High | Ga | 5000 | 228.2 | 71.91 | 7.16 | 18.80 | 0.00 | 0.47 | 2.54 |
| 1205 | High | Na | 1000 | 228.5 | 72.00 | 6.74 | 19.12 | 0.00 | 0.47 | 2.74 |
| 1206 | High | Li | 1000 | 228.3 | 71.86 | 7.15 | 18.86 | 0.00 | 0.47 | 1.96 |
| 1207 | High | Li | 1000 | 228.5 | 71.87 | 7.18 | 18.83 | 0.00 | 0.46 | 1.86 |
| 1208 | High | Ga | 5000 | 228.3 | 71.81 | 7.09 | 18.97 | 0.00 | 0.46 | 2.12 |
| 1209 | High | K | 1000 | 228.2 | 72.19 | 6.71 | 19.04 | 0.00 | 0.40 | 3.14 |
| 1210 | High | K | 1000 | 228.2 | 72.27 | 6.67 | 19.01 | 0.00 | 0.39 | 2.97 |
| 1211 | High | Rb | 1000 | 199.6 | 73.36 | 5.48 | 19.15 | 0.00 | 0.37 | 5.58 |
| 1212 | High | Rb | 1000 | 199.6 | 73.22 | 5.64 | 19.15 | 0.00 | 0.36 | 4.98 |
| 1213 | High | Rb | 1000 | 199.6 | 73.29 | 5.59 | 19.14 | 0.00 | 0.35 | 5.09 |
| 1214 | High | La | 1000 | 228.3 | 72.16 | 6.79 | 19.06 | 0.00 | 0.33 | 2.21 |
| 1215 | High | La | 1000 | 228.5 | 72.12 | 6.80 | 19.09 | 0.00 | 0.33 | 1.88 |
| 1216 | High | La | 1000 | 228.3 | 72.07 | 6.81 | 19.13 | 0.00 | 0.33 | 1.96 |
| 1217 | High | Sr | 1000 | 198.3 | 72.28 | 6.70 | 19.19 | 0.00 | 0.19 | 1.30 |
| 1218 | High | Sr | 1000 | 198.6 | 72.20 | 6.91 | 19.07 | 0.00 | 0.18 | 0.82 |
| 1219 | High | Ba | 1000 | 200.0 | 72.45 | 6.58 | 19.17 | 0.00 | 0.17 | 1.78 |
| 1220 | High | Ba | 1000 | 200.1 | 72.56 | 6.52 | 19.11 | 0.00 | 0.17 | 2.28 |
| 1221 | High | Ga | 5000 | 198.6 | 72.06 | 6.91 | 19.21 | 0.00 | 0.17 | 1.01 |
| 1222 | High | Ba | 1000 | 200.1 | 72.57 | 6.65 | 18.97 | 0.00 | 0.16 | 2.48 |
| 1223 | High | Ga | 5000 | 198.4 | 72.02 | 6.90 | 19.27 | 0.00 | 0.16 | 0.68 |
| 1224 | High | Na | 1000 | 198.4 | 71.96 | 6.59 | 19.64 | 0.00 | 0.16 | −0.12 |
| 1225 | High | Li | 1000 | 198.6 | 72.09 | 6.86 | 19.24 | 0.00 | 0.16 | 0.66 |
| 1226 | High | Li | 1000 | 198.7 | 72.22 | 6.93 | 19.05 | 0.00 | 0.16 | 1.20 |
| 1227 | High | Na | 1000 | 198.7 | 71.92 | 6.57 | 19.72 | 0.00 | 0.15 | −0.61 |
| 1228 | High | Rb | 1000 | 179.9 | 73.38 | 5.61 | 19.23 | 0.00 | 0.15 | 4.23 |
| 1229 | High | Rb | 1000 | 180.2 | 73.10 | 5.69 | 19.45 | 0.00 | 0.14 | 2.52 |
| 1230 | High | Rb | 1000 | 180.0 | 73.25 | 5.64 | 19.35 | 0.00 | 0.14 | 3.47 |
| 1231 | High | K | 1000 | 198.9 | 72.31 | 6.68 | 19.24 | 0.00 | 0.13 | 1.18 |
| 1232 | High | K | 1000 | 198.7 | 72.28 | 6.62 | 19.34 | 0.00 | 0.13 | 0.94 |
| 1233 | High | La | 1000 | 199.8 | 72.32 | 6.73 | 19.19 | 0.00 | 0.11 | 1.22 |
| 1234 | High | La | 1000 | 199.6 | 72.20 | 6.77 | 19.28 | 0.00 | 0.11 | 0.67 |
| 1235 | High | La | 1000 | 199.6 | 72.32 | 6.77 | 19.16 | 0.00 | 0.11 | 1.11 |
| 1236 | High | Sr | 1000 | 179.2 | 72.72 | 6.25 | 19.30 | 0.00 | 0.09 | 2.62 |
| 1237 | High | Ba | 1000 | 180.0 | 72.58 | 6.60 | 19.10 | 0.00 | 0.08 | 1.68 |
| 1238 | High | Sr | 1000 | 179.2 | 72.49 | 6.62 | 19.17 | 0.00 | 0.08 | 1.19 |
| 1239 | High | Ga | 5000 | 178.3 | 72.24 | 6.83 | 19.21 | 0.00 | 0.08 | 0.81 |
| 1240 | High | Ga | 5000 | 178.5 | 72.12 | 6.83 | 19.33 | 0.00 | 0.07 | 0.46 |
| 1241 | High | Ba | 1000 | 180.0 | 72.49 | 6.61 | 19.19 | 0.00 | 0.07 | 1.16 |
| 1242 | High | Na | 1000 | 179.4 | 72.12 | 6.55 | 19.62 | 0.00 | 0.07 | −0.43 |
| 1243 | High | Ba | 1000 | 180.0 | 72.48 | 6.55 | 19.27 | 0.00 | 0.07 | 1.02 |
| 1244 | High | Li | 1000 | 179.1 | 72.36 | 6.77 | 19.16 | 0.00 | 0.07 | 1.21 |
| 1245 | High | Li | 1000 | 179.1 | 72.20 | 6.87 | 19.22 | 0.00 | 0.07 | 0.24 |
| 1246 | High | Na | 1000 | 179.1 | 72.12 | 6.58 | 19.59 | 0.00 | 0.07 | −0.23 |
| 1247 | High | K | 1000 | 178.8 | 72.46 | 6.64 | 19.21 | 0.00 | 0.06 | 0.95 |
| 1248 | High | La | 1000 | 180.2 | 72.29 | 6.61 | 19.41 | 0.00 | 0.05 | 0.42 |
| 1249 | High | K | 1000 | 179.2 | 72.47 | 6.61 | 19.23 | 0.00 | 0.05 | 1.20 |
| 1250 | High | La | 1000 | 179.7 | 72.36 | 6.59 | 19.36 | 0.00 | 0.05 | 0.87 |
| 1251 | High | La | 1000 | 180.0 | 72.16 | 6.72 | 19.44 | 0.00 | 0.05 | −0.43 |

We claim:

1. A catalyst, comprising: copper chromite, palladium, and lanthanum, wherein said palladium and lanthanum are deposited on said copper chromite.

2. The catalyst according to claim 1 which comprises about 0.1 to about 10 weight percent palladium, based on the total weight of said catalyst.

3. The catalyst according to claim 2 which comprises about 0.5 to about 5 weight percent palladium.

4. The catalyst according to claim 3 which comprises about 0.5 to about 2 weight percent palladium.

5. The catalyst according to claim 1 which comprises about 500 to about 8000 parts per million of said lanthanum, based on the total weight of said catalyst.

6. The catalyst according to claim 5 which comprises about 1000 to about 5000 parts per million of said lanthanum.

7. The catalyst according to claim 1 which comprises at least 60 weight percent weight percent of said copper chromite, based on the total weight of the catalyst.

8. The catalyst according to claim 1 wherein said copper chromite comprises about 15 to 60 weight percent copper and about 15 to 60 weight percent chromium, based on the weight of said copper chromite.

9. The catalyst according to claim 1 wherein said copper chromite comprises a gram-atom ratio of copper to chromium of about 1:10 to about 10:1.

10. The catalyst according to claim 9 wherein said copper chromite comprises a gram-atom ratio of copper to chromium of about 1:5 to about 5:1.

11. The catalyst according to claim 10 wherein said copper chromite comprises a gram-atom ratio of copper to chromium of about 1:2 to about 2:1.

12. A catalyst, comprising: copper chromite having a gram-atom ratio of copper to chromium of about 1:2 to about 2:1, about 0.5 to about 1.5 weight percent palladium, and about 4000 to about 6000 ppm lanthanum, wherein said palladium and said lanthanum are deposited on said copper chromite.

13. A catalyst, consisting essentially of: copper chromite having a gram-atom ratio of copper to chromium of about 1:2 to about 2, about 0.5 to about 1.5 weight percent palladium, and about 4000 to about 6000 ppm lanthanum, wherein palladium and said lanthanum are deposited on said copper chromite.

14. A process for the preparation of a catalyst, comprising: contacting copper chromite with a solution of a palladium compound and a solution of a lanthanum compound; drying said copper chromite, and calcining said dried copper chromite.

15. The process according to claim 14 wherein said catalyst comprises about 0.1 to about 10 weight percent palladium and about 500 to about 8000 parts per million of lanthanum deposited on said copper chromite, wherein said weight percentage and parts per million are based on the total weight of said hydrogenation catalyst.

16. The process according to claim 15 further comprising, (i) contacting copper chromite with a solution of a palladium compound; (ii) drying said copper chromite; (iii) calcining said dried copper chromite from step (ii); (iv) contacting said calcined copper chromite from step (iii) with a solution of a lanthanum compound; (v) drying said copper chromite from step (iv); and (vi) calcining said dried copper chromite from step (v).

17. The process according to claim 16 wherein said drying steps (ii) and (v) independently are carried out at a temperature of about 40 to about 150° C. and said calcination steps (iii) and (vi) independently are carried out at a temperature of about 400 to about 600° C.

18. The process according to claim 16 wherein said catalyst comprises about 0.5 to about 2 weight percent palladium and about 1000 to about 5000 parts per million of lanthanum.

19. A process for the preparation of methanol, comprising: contacting a gaseous feed comprising hydrogen, carbon monoxide, and optionally carbon dioxide, with a catalyst, comprising: copper chromite, palladium, and lanthanum, wherein said palladium and lanthanum are deposited on said copper chromite.

20. The process according to claim 19 wherein said catalyst comprises about 0.1 to about 10 weight percent palladium, based on the total weight of said catalyst.

21. The process according to claim 20 wherein said catalyst comprises about 0.5 to about 5 weight percent palladium.

22. The process according to claim 19 wherein said catalyst comprises about 500 to about 8000 parts per million of said lanthanum, based on the total weight of said catalyst.

23. The process according to claim 22 wherein said catalyst comprises about 1000 to about 5000 parts per million of said lanthanum.

24. The process according to claim 19 wherein said copper chromite comprises a gram-atom ratio of copper to chromium of about 1:2 to about 2:1.

25. The process according to claim 19 wherein said catalyst comprises about 0.5 to about 1.5 weight percent palladium, about 4000 to about 6000 ppm lanthanum, and wherein said copper chromite comprises a gram-atom ratio of copper to chromium of about 1:2 to about 2:1.

26. The process according to claim 19 wherein said catalyst comprises about 85 to about 99.85 weight percent said copper chromite.

27. The process according to claim 19 wherein said copper chromite comprises about 15 to 60 weight percent copper and about 15 to 60 weight percent chromium, based on the weight of said copper chromite.

28. The process according to claim 19 wherein said contacting is at temperature of about 150 to about 350° C. and at a pressure of about 10 to about 100 bara.

29. The process according to claim 28 wherein said contacting is at a temperature of about 180 to about 250° C. and at a pressure of about 30 to about 70 bara.

30. The process according to claim 19 wherein said gaseous feed comprises about 1 to about 25 weight % carbon dioxide, based on the total volume of said gaseous feed.

31. The process according to claim 30 wherein said gaseous feed comprises about 1 to about 5 weight percent carbon dioxide.

32. The process according to claim 30 wherein said gaseous feed comprises about 10 to about 20 weight percent carbon dioxide.

33. The process according to claim 19 which comprises contacting said gaseous feed and said catalyst in a fixed bed or a liquid slurry phase reactor.

34. A process for hydrogenating an carbonyl compound to an alcohol, comprising contacting at least one carbonyl compound with hydrogen in the presence of a catalyst, comprising: copper chromite, palladium, and lanthanum are, wherein said palladium and lanthanum deposited on said copper chromite.

35. The process according to claim 34 wherein said carbonyl compound comprises at least one aldehyde, ketone, carboxylic acid ester, or combinations thereof.

36. The process according to claim 35 wherein said carboxylic acid ester comprises at least one alkyl carboxylate comprising the residue of at least one hydroxy compound containing from 1 to about 40 carbon atoms.

37. The process according to claim 36 wherein said hydroxy compound is selected from methanol, ethanol, propanol, 1-butanol, 2-butanol, 2-ethylhexanol, 2,2-dimethyl-1, 3-propanediol, ethylene glycol, propylene glycol, 1,4-butanediol, 1,6-hexanediol, 1,10-decanediol, cyclohexanol, 4-methylcyclohexanemethanol, diethylene glycol, glycerin, and trimethylol propane.

38. The process according to claim 36 wherein said alkyl carboxylate comprises the residue of at least one aliphatic, cycloaliphatic, aryl, or aralkyl carboxylic acid having from 1 to about 40 carbon atoms.

39. The process according to claim 38 wherein said alkyl carboxylate comprises an alkyl glycolate.

40. The process according to claim 39 wherein said alkyl glycolate comprises methyl glycolate.

41. The process according to claim 38 wherein said cycloaliphatic carboxylic acid is selected from 1,2-cyclohexanedicarboxylic acid, 1,3-cyclo-hexanedicarboxylic acid, 1,4-cyclohexanedicarboxylic acid, and combinations thereof.

42. A process for the preparation of a cyclohexanedimethanol comprising contacting at least one dialkyl cyclohexanedicarboxylate with hydrogen in the presence of a catalyst, comprising: copper chromite, palladium, and lanthanum are, wherein said palladium and lanthanum deposited on said copper chromite.

43. The process according to claim 42 wherein said dialkyl cyclohexane-dicarboxylate is a dialkyl 1,4-cyclohexane dicarboxylate comprising residues of at least one hydroxy compound containing from 1 to about 20 carbon atoms.

44. The process according to claim 43 wherein said dialkyl 1,4-cyclohexane-dicarboxylate has a cis:trans molar ratio of about 1:1 to about 2:1 and said 1,4-cyclohexanedimethanol has a cis:trans molar ratio of 0.7:1 to about 2:1.

45. The process according to claim 43 wherein said hydroxy compound is selected from methanol, ethanol, propanol, 1-butanol, 2-butanol, 2-ethylhexanol, 2,2-dimethyl-1, 3-propanediol, ethylene glycol, propylene glycol, 1,4-butanediol, 1,6-hexanediol, 1,10-decanediol, cyclohexanol, 4-methylcyclohexanemethanol, diethylene glycol, glycerin, and trimethylolpropane.

46. The process according to claim 42 which is a continuous process.

47. The process according to claim 46 which is conducted in the liquid phase, vapor phase, or a combination of liquid and vapor phase.

48. The process according to claim 47 which is at a temperature of about 150° C. to about 350° C. and at a pressure is about 40 to about 450 bara.

49. The process according to claim 48 wherein said dialkyl cyclohexane-dicarboxylate comprises dimethyl 1,4-cyclohexanedicarboxylate.

50. The process according to claim 49 wherein said contacting is at a temperature of about 180 to about 250° C. and at a pressure of about 200 to about 350 bara.

51. The process according to claim 50 which comprises contacting said hydrogen said catalyst in a fixed bed or a liquid slurry phase reactor.

* * * * *

UNITED STATES PATENT AND TRADEMARK OFFICE
CERTIFICATE OF CORRECTION

PATENT NO. : 7,538,060 B2
APPLICATION NO. : 11/674831
DATED : May 26, 2009
INVENTOR(S) : Barnicki et al.

It is certified that error appears in the above-identified patent and that said Letters Patent is hereby corrected as shown below:

Column 53, Line 19:

least 60 weight percent weight percent of said copper
should read
least 60 weight percent of said copper Column 54, Line 40:

tacting is at temperature of about 150 to about 350°C. and at
should read
tacting is at a temperature of about 150 to about 350°C. and at Column 54, Line 57

A process for hydrogenating an carbonyl compound to
should read
A process for hydrogenating a carbonyl compound to Column 54, Line 60:

ing: copper chromite, palladium, and lanthanum are, wherein
should read
ing: copper chromite, palladium, and lanthanum, wherein Column 54, Line 61:

said palladium and lanthanum deposited on said copper
should read
said palladium and lanthanum are deposited on said copper Column 55, line 25:

prising: copper chromite, palladium, and lanthanum are,
should read
prising: copper chromite, palladium, and lanthanum,

CERTIFICATE OF CORRECTION (continued)
U.S. Pat. No. 7,538,060 B2

Column 55, Line 26:

wherein said palladium and lanthanum deposited on said
should read
wherein said palladium and lanthanum are deposited on said Column 56, Line 18:

perature of about 150°C. to about 350°C. and at a pressure is
should read
perature of about 150°C. to about 350°C. and at a pressure of Column 56, Line 28:

contacting said hydrogen said catalyst in a fixed bed or a
should read
contacting said hydrogen and said catalyst in a fixed bed or a Signed and Sealed this Twenty-third Day of February, 2010

David J. Kappos
*Director of the United States Patent and Trademark Office*